(12) United States Patent
Lang et al.

(10) Patent No.: US 9,872,773 B2
(45) Date of Patent: *Jan. 23, 2018

(54) STANDARD OR CUSTOMIZED TIBIAL IMPLANT WITH MULTIPLE CONVEXITIES AND CONCAVITIES, AND VARIABLE SLOPE

(71) Applicant: ConforMIS, Inc., Bedford, MA (US)

(72) Inventors: Philipp Lang, Lexington, MA (US); Daniel Steines, Lexington, MA (US); Hacene Bouadi, Palo Alto, CA (US); David Miller, Cupertino, CA (US)

(73) Assignee: ConforMIS, Inc., Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/259,548

(22) Filed: Apr. 23, 2014

(65) Prior Publication Data

US 2014/0250676 A1    Sep. 11, 2014

Related U.S. Application Data

(63) Continuation of application No. 12/772,683, filed on May 3, 2010, now Pat. No. 8,709,089, which is a
(Continued)

(51) Int. Cl.
*A61F 2/30* (2006.01)
*A61F 2/32* (2006.01)
(Continued)

(52) U.S. Cl.
CPC ...... *A61F 2/30942* (2013.01); *A61F 2/30756* (2013.01); *A61F 2/32* (2013.01);
(Continued)

(58) Field of Classification Search
CPC .... A61F 2/30756; A61F 2/30942; A61F 2/32; A61F 2/3606; A61F 2/38; A61F 2/3804;
(Continued)

(56) References Cited

U.S. PATENT DOCUMENTS 3,816,855 A    6/1974 Saleh ..................................... 3/1
4,000,525 A    1/1977 Klawitter et al. ............. 3/1.911
(Continued)

FOREIGN PATENT DOCUMENTS

DE    8909091 U1    11/1989    ............... A61F 2/38
EP    0626156 B1    11/1994    ............... A61F 2/38
(Continued)

OTHER PUBLICATIONS

European Patent Office, Extended European Search Report—European Application No. 09717686.1-2310 dated Mar. 6, 2012, 7 pages.
(Continued)

*Primary Examiner* — Pedro Philogene
(74) *Attorney, Agent, or Firm* — Sunstein Kann Murphy & Timbers LLP

(57) ABSTRACT

This invention is directed to orthopedic implants and systems. The invention also relates to methods of implant design, manufacture, modeling and implantation as well as to surgical tools and kits used therewith. The implants are designed by analyzing the articular surface to be corrected and creating a device with an anatomic or near anatomic fit; or selecting a pre-designed implant having characteristics that give the implant the best fit to the existing defect.

26 Claims, 38 Drawing Sheets

Related U.S. Application Data continuation of application No. 10/681,749, filed on Oct. 7, 2003, now Pat. No. 7,799,077.

(60) Provisional application No. 60/416,601, filed on Oct. 7, 2002, provisional application No. 60/467,686, filed on May 2, 2003.

(51) Int. Cl.
| | | |
|---|---|---|
| *A61F 2/36* | (2006.01) | |
| *A61F 2/38* | (2006.01) | |
| *A61F 2/40* | (2006.01) | |
| *A61F 2/42* | (2006.01) | |
| *B33Y 80/00* | (2015.01) | |
| *A61B 17/00* | (2006.01) | |
| *A61F 2/34* | (2006.01) | |
| *A61F 2/46* | (2006.01) | |

(52) U.S. Cl.
CPC .............. *A61F 2/3603* (2013.01); *A61F 2/38* (2013.01); *A61F 2/3804* (2013.01); *A61F 2/40* (2013.01); *A61F 2/42* (2013.01); *A61F 2/4202* (2013.01); *A61F 2/4261* (2013.01); *A61F 2/4657* (2013.01); *A61B 17/00234* (2013.01); *A61F 2/30767* (2013.01); *A61F 2/34* (2013.01); *A61F 2/4081* (2013.01); *A61F 2/4603* (2013.01); *A61F 2002/3007* (2013.01); *A61F 2002/30016* (2013.01); *A61F 2002/30062* (2013.01); *A61F 2002/30092* (2013.01); *A61F 2002/30113* (2013.01); *A61F 2002/30125* (2013.01); *A61F 2002/30133* (2013.01); *A61F 2002/30179* (2013.01); *A61F 2002/30242* (2013.01); *A61F 2002/30247* (2013.01); *A61F 2002/30253* (2013.01); *A61F 2002/30324* (2013.01); *A61F 2002/30604* (2013.01); *A61F 2002/30616* (2013.01); *A61F 2002/30822* (2013.01); *A61F 2002/30841* (2013.01); *A61F 2002/30843* (2013.01); *A61F 2002/30878* (2013.01); *A61F 2002/30884* (2013.01); *A61F 2002/30892* (2013.01); *A61F 2002/30894* (2013.01); *A61F 2002/30948* (2013.01); *A61F 2002/30952* (2013.01); *A61F 2002/30957* (2013.01); *A61F 2002/30962* (2013.01); *A61F 2002/3208* (2013.01); *A61F 2002/3216* (2013.01); *A61F 2002/3412* (2013.01); *A61F 2002/3414* (2013.01); *A61F 2002/4007* (2013.01); *A61F 2002/4233* (2013.01); *A61F 2002/4251* (2013.01); *A61F 2002/4631* (2013.01); *A61F 2002/4635* (2013.01); *A61F 2210/0004* (2013.01); *A61F 2210/0014* (2013.01); *A61F 2230/0006* (2013.01); *A61F 2230/0008* (2013.01); *A61F 2230/0015* (2013.01); *A61F 2230/0058* (2013.01); *A61F 2230/0071* (2013.01); *A61F 2230/0076* (2013.01); *A61F 2250/0019* (2013.01); *A61F 2250/0036* (2013.01); *A61F 2310/00011* (2013.01); *A61F 2310/00179* (2013.01); *A61F 2310/00293* (2013.01); *A61F 2310/00365* (2013.01); *A61F 2310/00383* (2013.01); *A61F 2310/00395* (2013.01); *A61F 2310/00592* (2013.01); *B33Y 80/00* (2014.12); *Y10S 264/30* (2013.01); *Y10T 29/49* (2015.01)

(58) Field of Classification Search
CPC .. A61F 2/40; A61F 2/42; A61F 2/4202; A61F 2/4265; A61F 2/4657; A61F 2/30767; A61F 2/34; A61F 2/4081; A61F 2/4603; A61F 2002/30016; A61F 2002/30062; A61F 2002/3007; A61F 2002/30092; A61F 2002/30113; A61F 2002/30125; A61F 2002/30133; A61F 2002/30179; A61F 2002/30242; A61F 2002/30247; A61F 2002/30253; A61F 2002/30324; A61F 2002/30604; A61F 2002/30616; A61F 2002/30822; A61F 2002/30841; A61F 2002/30843; A61F 2002/30878; A61F 2002/30884; A61F 2002/30892; A61F 2002/30894; A61F 2002/30948; A61F 2002/30952; A61F 2002/30957; A61F 2002/30962; A61F 2002/3208; A61F 2002/3216; A61F 2002/3412; A61F 2002/3414; A61F 2002/4007; A61F 2002/4233; A61F 2002/4251; A61F 2002/4631; A61F 2002/4635; A61F 2210/0004; A61F 2210/0014; A61F 2230/0006; A61F 2230/0008; A61F 2230/0015; A61F 2230/0058; A61F 2230/0071; A61F 2230/0076; A61F 2250/0019; A61F 2250/0036; A61F 2310/00011; A61F 2310/00179; A61F 2310/00293; A61F 2310/00365; A61F 2310/00383; A61F 2310/00395; A61F 2310/00592; A61B 17/00234; Y10S 264/30; Y10T 29/49

USPC .... 606/80, 85, 86 R, 87–89, 96, 99; 29/592; 623/18.11, 20.14, 14.12, 22.11, 19.11, 623/20.35, 20.32, 17.11, 23.61, 23.42; 600/587, 407

See application file for complete search history.

(56) References Cited

U.S. PATENT DOCUMENTS

| | | | |
|---|---|---|---|
| 4,178,641 A | 12/1979 | Grundei et al. | 3/1.911 |
| 4,207,627 A | 6/1980 | Cloutier | 3/1.911 |
| 4,211,228 A | 7/1980 | Cloutier | 128/303 R |
| 4,436,684 A | 3/1984 | White | 264/138 |
| 4,714,474 A | 12/1987 | Brooks, Jr. et al. | 623/20 |
| 4,883,488 A | 11/1989 | Bloebaum et al. | |
| 4,936,853 A | 6/1990 | Fabian et al. | 623/20 |
| 4,944,757 A | 7/1990 | Martinez et al. | 623/20 |
| 5,019,103 A | 5/1991 | Van Zile et al. | 623/20 |
| 5,047,057 A | 9/1991 | Lawes | 623/20 |
| 5,152,797 A | 10/1992 | Luckman et al. | 623/20 |
| 5,171,244 A | 12/1992 | Caspari et al. | 606/88 |
| 5,282,868 A | 2/1994 | Bahler | 623/20 |
| 5,326,363 A | 7/1994 | Aikins | 623/20 |
| 5,387,240 A * | 2/1995 | Pottenger | A61F 2/3886 623/20.29 |
| 5,507,820 A * | 4/1996 | Pappas | A61F 2/38 623/20.19 |
| 5,702,463 A * | 12/1997 | Pothier | A61F 2/389 606/99 |
| 5,702,464 A | 12/1997 | Lackey et al. | 623/20 |
| 5,743,918 A * | 4/1998 | Calandruccio | A61B 17/1615 128/898 |
| 5,762,125 A * | 6/1998 | Mastrorio | A61F 2/30942 164/34 |
| 5,824,102 A | 10/1998 | Buscayret | 623/20 |
| 5,957,979 A | 9/1999 | Beckman et al. | 623/20 |
| 5,964,808 A | 10/1999 | Blaha et al. | 623/20 |
| 5,968,099 A | 10/1999 | Badorf et al. | 623/20 |
| 6,013,103 A | 1/2000 | Kaufman et al. | 623/20 |
| 6,190,415 B1 | 2/2001 | Cooke et al. | 623/20.33 |
| 6,205,411 B1 | 3/2001 | DiGioia, III et al. | 703/11 |
| 6,224,632 B1 | 5/2001 | Pappas et al. | 623/20.34 |
| 6,299,645 B1 | 10/2001 | Ogden | 623/20.21 |
| 6,379,388 B1 | 4/2002 | Ensign et al. | 623/20.34 |

(56) References Cited

U.S. PATENT DOCUMENTS

| | | | | |
|---|---|---|---|---|
| 6,623,526 | B1 | 9/2003 | Lloyd | 623/20.28 |
| 6,706,068 | B2* | 3/2004 | Ferree | A61F 2/4425 |
| | | | | 623/17.11 |
| 6,712,856 | B1 | 3/2004 | Carignan et al. | 623/20.35 |
| 7,048,741 | B2 | 5/2006 | Swanson | 606/88 |
| 7,060,101 | B2 | 6/2006 | O'Connor et al. | 623/20.32 |
| 7,105,026 | B2 | 9/2006 | Johnson et al. | 623/20.14 |
| 7,172,596 | B2 | 2/2007 | Coon et al. | 606/87 |
| 7,264,635 | B2 | 9/2007 | Suguro et al. | 623/20.14 |
| 7,799,077 | B2* | 9/2010 | Lang | A61F 2/30756 |
| | | | | 264/DIG. 30 |
| 8,265,730 | B2 | 9/2012 | Alexander et al. | 600/410 |
| 8,306,601 | B2 | 11/2012 | Lang et al. | 600/407 |
| 8,337,501 | B2 | 12/2012 | Fitz et al. | 606/86 R |
| 8,337,507 | B2 | 12/2012 | Lang et al. | 606/102 |
| 8,343,218 | B2 | 1/2013 | Lang et al. | 623/16.11 |
| 8,366,771 | B2 | 2/2013 | Burdulis, Jr. et al. | 623/14.12 |
| 8,369,926 | B2 | 2/2013 | Lang et al. | 600/407 |
| 8,377,129 | B2 | 2/2013 | Fitz et al. | 623/14.12 |
| 8,480,754 | B2 | 7/2013 | Bojarski et al. | 623/20.35 |
| 8,556,983 | B2 | 10/2013 | Bojarski et al. | 623/20.35 |
| 8,634,617 | B2 | 1/2014 | Tsougarakis et al. | 382/128 |
| 8,771,365 | B2 | 7/2014 | Bojarski et al. | 623/20.32 |
| 9,603,711 | B2 | 3/2017 | Bojarski et al. | |
| 9,642,711 | B2* | 5/2017 | Carson | A61F 2/3886 |
| 2002/0055783 | A1* | 5/2002 | Tallarida et al. | 623/20.14 |
| 2002/0082741 | A1* | 6/2002 | Mazumder | A61F 2/30767 |
| | | | | 700/123 |
| 2003/0014122 | A1 | 1/2003 | Whiteside | 623/20.32 |
| 2003/0055502 | A1 | 3/2003 | Lang et al. | 623/16.11 |
| 2003/0060885 | A1* | 3/2003 | Fell et al. | 623/14.12 |
| 2003/0236473 | A1* | 12/2003 | Dore | A61B 5/1077 |
| | | | | 600/587 |
| 2004/0117023 | A1* | 6/2004 | Gerbec | A61F 2/30734 |
| | | | | 623/18.11 |
| 2004/0138755 | A1* | 7/2004 | O'Connor | A61F 2/389 |
| | | | | 623/20.32 |
| 2004/0199249 | A1* | 10/2004 | Fell | 623/14.12 |
| 2004/0204766 | A1* | 10/2004 | Siebel | A61F 2/38 |
| | | | | 623/20.31 |
| 2005/0107884 | A1 | 5/2005 | Johnson et al. | 623/20.15 |
| 2005/0197710 | A1* | 9/2005 | Naegerl | A61F 2/389 |
| | | | | 623/20.32 |
| 2005/0267584 | A1 | 12/2005 | Burdulis, Jr. et al. | 623/20.19 |
| 2006/0058884 | A1 | 3/2006 | Aram et al. | 623/20.15 |
| 2007/0198022 | A1 | 8/2007 | Lang et al. | 606/88 |
| 2008/0119940 | A1 | 5/2008 | Otto et al. | 623/20.31 |
| 2008/0172125 | A1 | 7/2008 | Ek | 623/14.12 |
| 2008/0195216 | A1 | 8/2008 | Lang | 623/18.11 |
| 2010/0274534 | A1 | 10/2010 | Steines et al. | 703/1 |
| 2011/0029093 | A1 | 2/2011 | Bojarski et al. | 623/20.35 |
| 2011/0087332 | A1 | 4/2011 | Bojarski et al. | 623/20.32 |
| 2012/0191205 | A1 | 7/2012 | Bojarski et al. | 623/20.32 |
| 2014/0005792 | A1 | 1/2014 | Lang et al. | 623/20.32 |

FOREIGN PATENT DOCUMENTS

| | | | | |
|---|---|---|---|---|
| EP | 0672397 | A1 | 9/1995 | A61F 2/338 |
| EP | 0809987 | A2 | 12/1997 | A61F 2/38 |
| EP | 1329205 | A1 | 7/2003 | A61F 2/38 |
| GB | 2304051 | A | 3/1997 | A61F 2/38 |
| JP | 11-19104 | A | 1/1999 | A61F 2/28 |
| WO | 00/76428 | A1 | 12/2000 | A61F 2/38 |
| WO | 01/66021 | A1 | 9/2001 | A61B 17/14 |
| WO | 05/002473 | A1 | 1/2005 | A61F 2/38 |

OTHER PUBLICATIONS

European Patent Office, Extended European Search Report—Application No. 10792589.3-2310, dated Feb. 7, 2013, 9 pages.
European Patent Office, European Search Report—Application No. 10829105.5-1654 dated Nov. 5, 2013, 3 pages.
European Patent Office, Extended European Search Report—Application No. 10838327.4-1654 dated Nov. 14, 2013, 6 pages.
European Patent Office, European Search Report pertaining to European Application No. 15189568.7-1654 dated Feb. 9, 2016, 7 pages.
European Patent Office, Partial Supplementary European Search Report—Application No. 13771863.1-1654, dated Apr. 26, 2016, 7 pages.
International Searching Authority, Great Britain Search and Examination Report—Application No. GB1201112.8 dated Feb. 3, 2014, 4 pages.
International Searching Authority, International Search Report International Application No. PCT/US2009/036218, dated Apr. 28, 2009, together with the Written Opinion of the International Searching Authority, 10 pages.
International Searching Authority, International Search Report—International Application No. PCT/US2010/039587, dated Aug. 19, 2010, together with the Written Opinion of the International Searching Authority, 15 pages.
International Searching Authority, International Search Report—International Application No. PCT/US2010/055483, dated Jul. 28, 2011, together with the Written Opinion of the International Searching Authority, 9 pages.
International Searching Authority, International Search Report—International Application No. PCT/US2010/061141, dated Aug. 31, 2011, together with the Written Opinion of the International Searching Authority, 8 pages.
International Searching Authority, International Search Report—International Application No. PCT/US2013/025117 dated Apr. 12, 2013, together with the Written Opinion of the International Searching Authority, 9 pages.
International Searching Authority, International Search Report—International Application No. PCT/US2013/028762 dated Jun. 21, 2013, together with the Written Opinion of the International Searching Authority, 13 pages.
International Searching Authority, International Search Report—International Application No. PCT/US2013/035536 dated Jul. 18, 2013, together with the Written Opinion of the International Searching Authority, 9 pages.
Intellectual Property Office of Singapore, Search Report and Written Opinion dated Jun. 10, 2015, pertaining to Singapore Application No. 11201405753X, 33 pages.
Intellectual Property Office of Singapore, Written Opinion pertaining to Singapore Patent Application No. 11201405753X, dated Jan. 20, 2016, 12 pages.
U.S. Appl. No. 12/398,880, filed Mar. 5, 2009.
U.S. Appl. No. 12/799,641, filed Apr. 28, 2010.
U.S. Appl. No. 13/294,617, filed Nov. 11, 2011.
U.S. Appl. No. 14/017,176, filed Sep. 3, 2013.
U.S. Appl. No. 14/169,093, filed Jan. 30, 2014.
U.S. Appl. No. 14/315,714, filed Jun. 26, 2014.
U.S. Appl. No. 14/373,555, filed Feb. 7, 2013.
U.S. Appl. No. 14/380,212, filed Mar. 2, 2013.
U.S. Appl. No. 14/389,987, filed Apr. 6, 2013.
U.S. Appl. No. 14/656,247, filed Mar. 12, 2015.
Whiteside, MD et al., "The Effect of Posterior Tibial Slope on Knee Stability After Ortholoc Total Knee Arthroplasty," The Journal of Arthroplasty, pp. S51-S57, Oct. 1988 Supplement.
Sunstein Kann Murphy & Timbers LLP, Request for Continued Examination and Response filed Oct. 21, 2016, pertaining to U.S. Appl. No. 13/294,617, 18 pages.
United States Patent & Trademark Office, Office Action dated Nov. 17, 2016, pertaining to U.S. Appl. No. 13/294,617, 7 pages.
Sunstein Kann Murphy & Timbers LLP, Request for Continued Examination and Response filed Aug. 3, 2016, pertaining to U.S. Appl. No. 14/315,714, 18 pages.
United States Patent & Trademark Office, Office Action dated Sep. 20, 2016, pertaining to U.S. Appl. No. 14/315,714, 7 pages.
European Patent Office, Extended European Search Report—Application No. 13755572.8-1654, dated Sep. 23, 2015, 6 pages.
European Patent Office, Extended European Search Report—Application No. 14191052.1-1654, dated Apr. 29, 2015, 7 pages.

(56) References Cited

OTHER PUBLICATIONS

Sunstein Kann Murphy & Timbers LLP, Response to Office Action dated Nov. 17, 2016, pertaining to U.S. Appl. No. 13/294,617, 12 pages.
United States Patent & Trademark Office, Office Action dated Mar. 29, 2017, pertaining to U.S. Appl. No. 13/294,617, 8 pages.
Sunstein Kann Murphy & Timbers LLP, Amendment to Office Action dated Sep. 20, 2016, pertaining to U.S. Appl. No. 14/315,714, 12 pages.
United States Patent & Trademark Office, Office Action dated Feb. 28, 2017, pertaining to U.S. Appl. No. 14/315,714, 8 pages.
Sunstein Kann Murphy & Timbers LLP, Request for Continued Examination, Amendment and Interview Summary dated Aug. 29, 2017, pertaining to U.S. Appl. No. 13/294,617, 13 pages.
United States Patent & Trademark Office, Office Action dated Jul. 19, 2017, pertaining to U.S. Appl. No. 14/315,714, 12 pages.
"Notice of Allowability dated Oct. 2, 2017, pertaining to U.S. Appl. No. 13/294,617, 2 pages".
"Notice of Allowance dated Sep. 21, 2017, pertaining to U.S. Appl. No. 13/294,617, 5 pages".

* cited by examiner

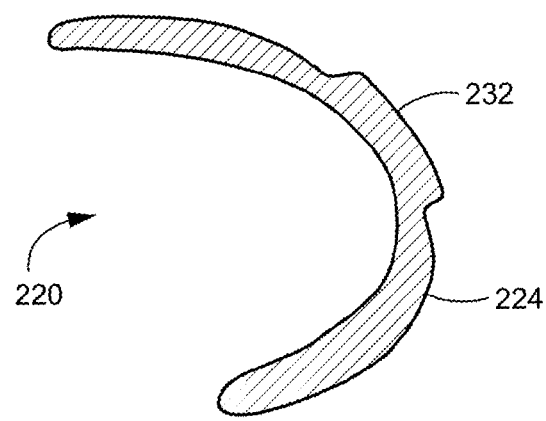
FIG. 12A
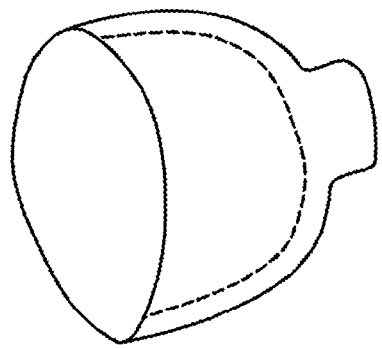 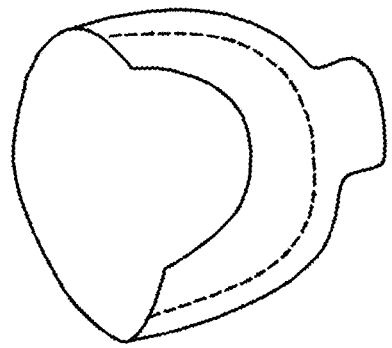
FIG. 12B   FIG. 12C
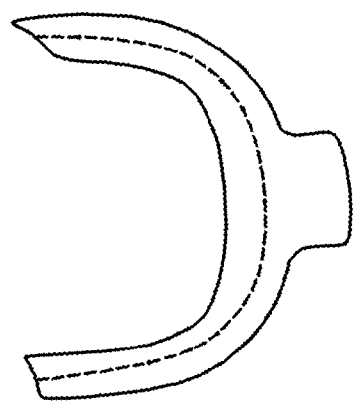 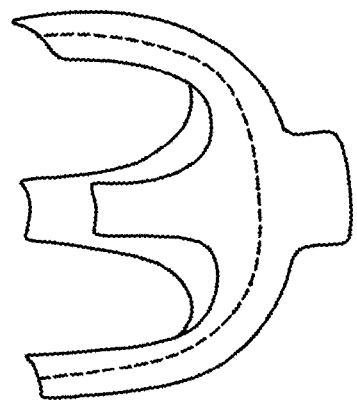
FIG. 12D   FIG. 12E

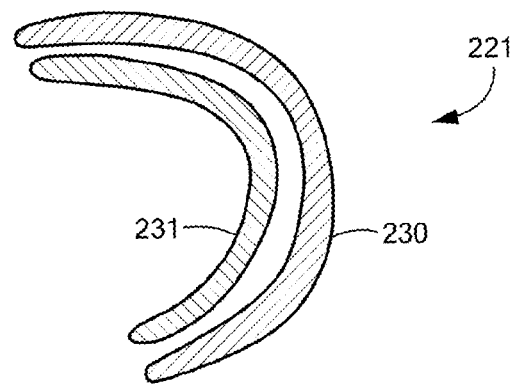
*FIG. 13A*
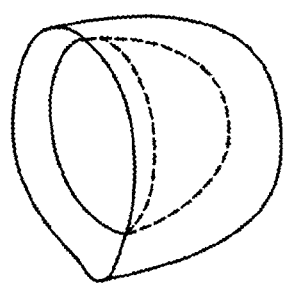 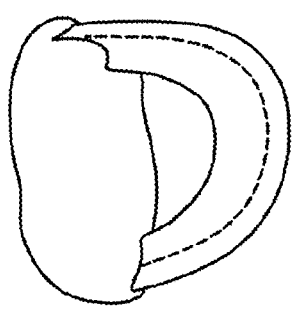 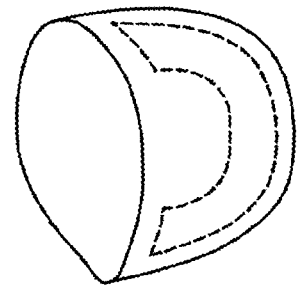
*FIG. 13B*    *FIG. 13C*    *FIG. 13D*
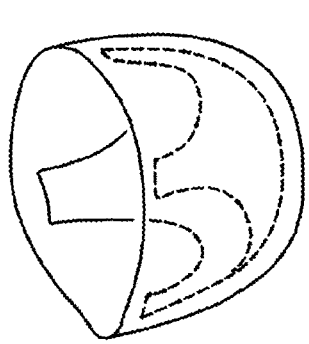 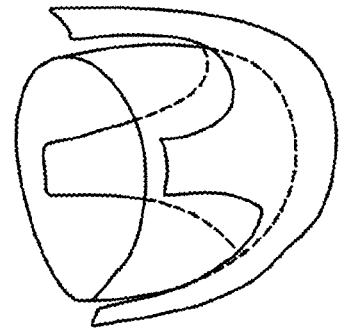
*FIG. 13E*    *FIG. 13F*

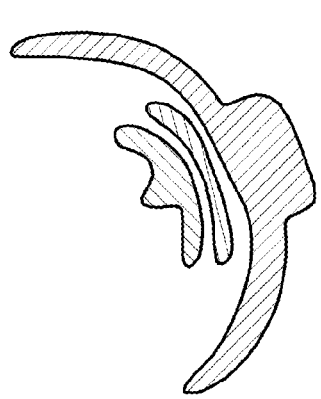
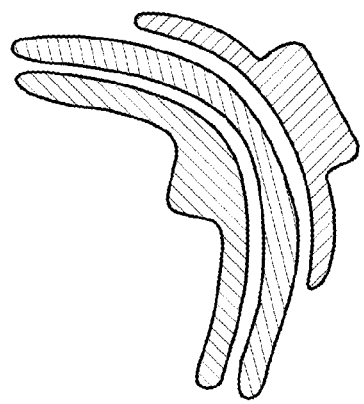
FIG. 16C  FIG. 16D
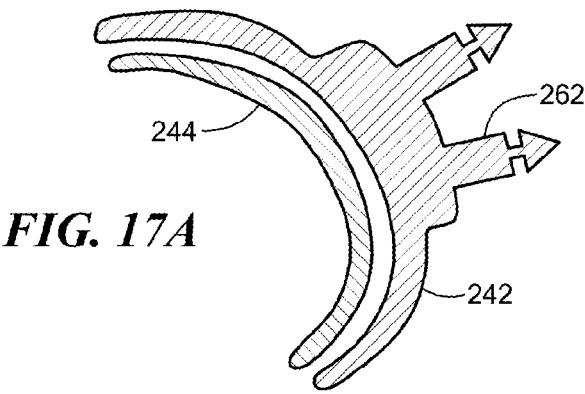
FIG. 17A
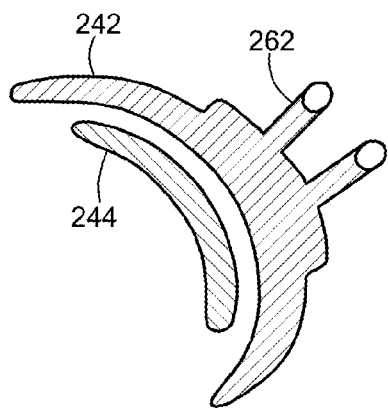
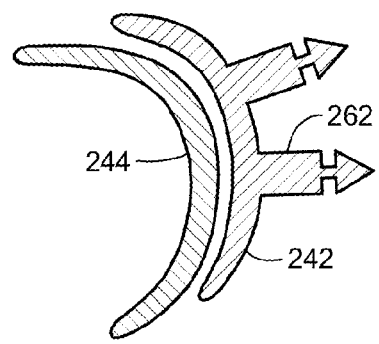
FIG. 17B  FIG. 17C

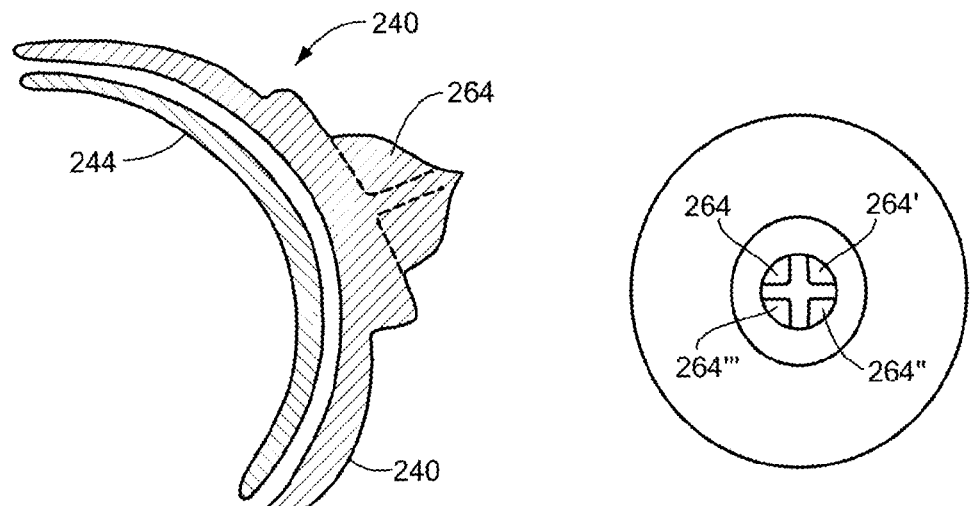
FIG. 18A
FIG. 18B
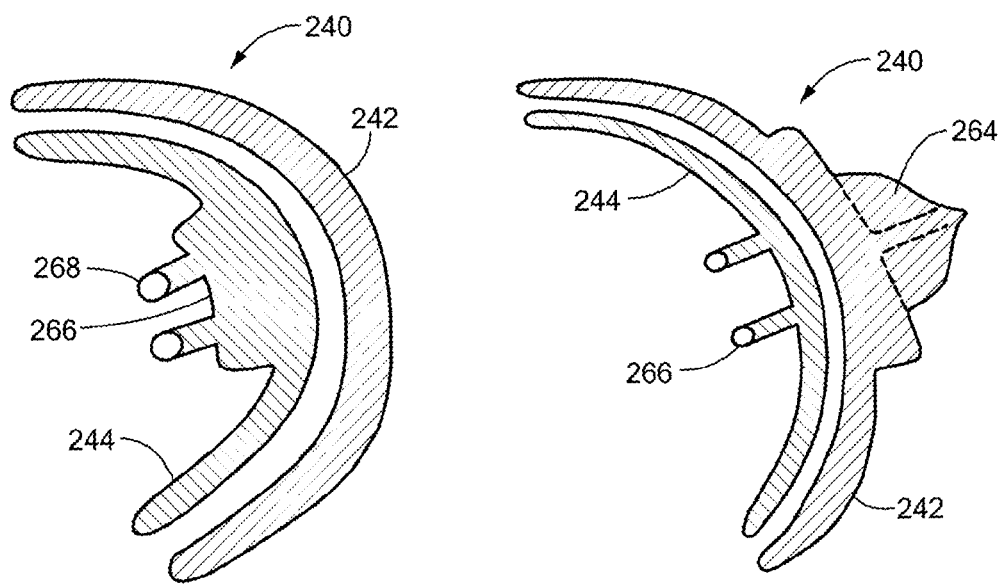
FIG. 19A
FIG. 19B

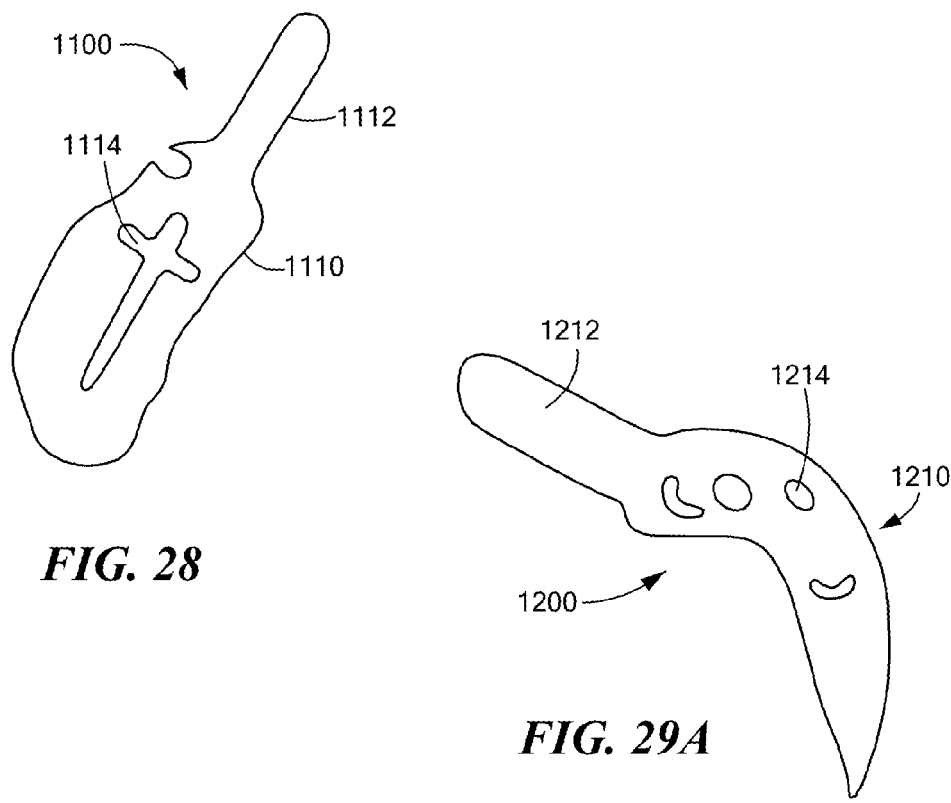
FIG. 28
FIG. 29A
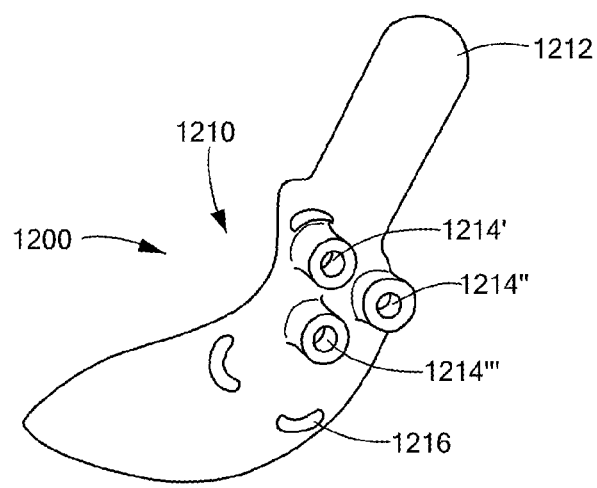
FIG. 29B

STANDARD OR CUSTOMIZED TIBIAL IMPLANT WITH MULTIPLE CONVEXITIES AND CONCAVITIES, AND VARIABLE SLOPE

CROSS-REFERENCE TO RELATED APPLICATIONS

This application is a continuation of U.S. patent application Ser. No. 12/772,683, filed May 3, 2010, entitled "Minimally Invasive Joint Implant with 3-Dimensional Geometry Matching the Articular Surfaces," which in turn is a continuation of U.S. patent application Ser. No. 10/681,749, filed Oct. 7, 2003, entitled "Minimally Invasive Joint Implant with 3-Dimensional Geometry Matching the Articular Surfaces," which in turn claims priority to U.S. Provisional Patent Application 60/416,601 filed Oct. 7, 2002, entitled "Minimally Invasive Joint Implant with 3-Dimensional Geometry Matching the Articular Surfaces," and U.S. Provisional Patent Application 60/467,686, filed May 2, 2003, entitled "Joint Implants" on May 2, 2003. Each of the above-described applications is hereby incorporated herein by reference in its entirety.

FIELD OF THE INVENTION

This invention is directed to orthopedic implants and systems. The implants can be joint implants and/or interpositional joint implants. The invention also relates to methods of implant design, manufacture, modeling and implantation as well as to surgical tools and kits used therewith. This invention also relates to a self-expandable orthopedic implant amendable to arthroscopic insertion and profile alteration. Finally, this invention is related to joint implants that are shaped such that the implants re-establish normal, or near normal, 3D articular geometry or alignment and facilitate joint movement that exceeds from 60 to 99.9% of the normal range of motion for the joint and which are capable of withstanding up to 100% of the normal shear force exerted on the joint during motion.

BACKGROUND OF THE INVENTION

There are various types of cartilage, e.g., hyaline cartilage and fibrocartilage. Hyaline cartilage is found at the articular surfaces of bones, e.g., in the joints, and is responsible for providing the smooth gliding motion characteristic of moveable joints. Articular cartilage is firmly attached to the underlying bones and measures typically less than 5 mm in thickness in human joints, with considerable variation depending on the joint and more particularly the site within the joint. In addition, articular cartilage is aneural, avascular, and alymphatic. In adult humans, this cartilage derives its nutrition by a double diffusion system through the synovial membrane and through the dense matrix of the cartilage to reach the chondrocyte, the cells that are found in the connective tissue of cartilage.

Adult cartilage has a limited ability of repair; thus, damage to cartilage produced by disease, such as rheumatoid arthritis and/or osteoarthritis, or trauma can lead to serious physical deformity and debilitation. Furthermore, as human articular cartilage ages, its tensile properties change. Thus, the tensile stiffness and strength of adult cartilage decreases markedly over time as a result of the aging process.

For example, the superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

Usually, severe damage or loss of cartilage is treated by replacement of the joint with a prosthetic material, for example, silicone, e.g. for cosmetic repairs, or suitable metal alloys. See, e.g., U.S. Pat. No. 6,383,228 to Schmotzer, issued May 7, 2002; U.S. Pat. No. 6,203,576 to Afriat, et al., issued Mar. 20, 2001; U.S. Pat. No. 6,126,690 to Ateshian et al., issued Oct. 3, 2000. Implantation of these prosthetic devices is usually associated with loss of underlying tissue and bone without recovery of the full function allowed by the original cartilage and, with some devices, serious long-term complications associated with the loss of significant amount of tissue and bone can include infection, osteolysis and also loosening of the implant.

As can be appreciated, joint arthroplasties are highly invasive and require surgical resection of the entire, or a majority of the, articular surface of one or more bones involved in the repair. Typically with these procedures, the marrow space is fairly extensively reamed in order to fit the stem of the prosthesis within the bone. Reaming results in a loss of the patient's bone stock and over time osteolysis will frequently lead to loosening of the prosthesis. Further, the area where the implant and the bone mate degrades over time requiring the prosthesis to eventually be replaced. Since the patient's bone stock is limited, the number of possible replacement surgeries is also limited for joint arthroplasty. In short, over the course of 15 to 20 years, and in some cases even shorter time periods, the patient can run out of therapeutic options ultimately resulting in a painful, non-functional joint.

The use of matrices, tissue scaffolds or other carriers implanted with cells (e.g., chondrocyte, chondrocyte progenitors, stromal cells, mesenchymal stem cells, etc.) has also been described as a potential treatment for cartilage repair. See, also, International Publications WO 99/51719 to Fofonoff published Oct. 14, 1999; WO 01/91672 to Simon et al., published Dec. 6, 2001; and WO 01/17463 to Mansmann, published Mar. 15, 2001; and U.S. Pat. No. 6,283,980 B1 to Vibe-Hansen, et al., issued Sep. 4, 2001; U.S. Pat. No. 5,842,477 to Naughton, et al., issued Dec. 1, 1998; U.S. Pat. No. 5,769,899 to Schwartz, issued Jun. 23, 1998; U.S. Pat. No. 4,609,551 to Caplan et al., issued Sep. 2, 1986; U.S. Pat. No. 5,041,138 to Vacanti et al., issued Aug. 20, 1991; U.S. Pat. No. 5,197,985 to Caplan et al., issued Mar. 30, 1993; U.S. Pat. No. 5,226,914 to Caplan, et al., issued Jul. 13, 1993; U.S. Pat. No. 6,328,765 to Hardwick et al., issued Dec. 11, 2001; U.S. Pat. No. 6,281,195 to Rueger et al., issued Aug. 28, 2001; and U.S. Pat. No. 4,846,835 to Grande, issued Jul. 11, 1989. However, clinical outcomes with biologic replacement materials such as allograft and autograft systems and tissue scaffolds have been uncertain since most of these materials cannot achieve a morphologic arrangement or structure similar to or identical to that of the normal, disease-free human tissue it is intended to replace. Moreover, the mechanical durability of these biologic replacement materials remains uncertain.

U.S. Pat. No. 6,206,927 to Fell, et al., issued Mar. 21, 2001, and U.S. Pat. No. 6,558,421 to Fell, et al., issued May 6, 2003, disclose a surgically implantable knee prosthesis that does not require bone resection. This prosthesis is described as substantially elliptical in shape with one or more straight edges. Accordingly, these devices are not designed to substantially conform to the actual shape (contour) of the remaining cartilage in vivo and/or the underlying bone. Thus, integration of the implant can be extremely difficult due to differences in thickness and curvature between the patient's surrounding cartilage and/or the underlying subchondral bone and the prosthesis.

Thus, there remains a need for a system and method for replicating the natural geography of a joint using one or more implant parts that can be implanted using minimally invasive techniques and tools for making those repairs and implants and methods that recreate natural or near natural three-dimensional geometric relationships between two articular surfaces of the joint.

SUMMARY OF THE INVENTION

The present invention provides methods and compositions for repairing joints, particularly devices and implants useful for repairing articular cartilage and for facilitating the integration of a wide variety of cartilage and bone repair materials into a subject. Among other things, the techniques described herein allow for the production of devices that substantially or completely conform to the contour of a particular subject's underlying cartilage and/or bone and/or other articular structures. In addition, the devices also preferably substantially or completely conform to the shape (size) of the cartilage. When the shape (e.g., size, thickness and/or curvature) of the articular cartilage surface is an anatomic or near anatomic fit with the non-damaged cartilage, with the subject's original cartilage, and/or with the underlying bone, the success of repair is enhanced.

The repair material can be shaped prior to implantation and such shaping can be based, for example, on electronic images that provide information regarding curvature or thickness of any "normal" cartilage surrounding a defect or area of diseased cartilage and/or on curvature of the bone underlying or surrounding the defect or area of diseased cartilage, as well as bone and/or cartilage comprising the opposing mating surface for the joint.

The current invention provides, among other things, for minimally invasive methods for partial joint replacement. The methods can result in little or no loss in bone stock resulting from the procedure. Additionally, the methods described herein help to restore the integrity of the articular surface by achieving an anatomic or near anatomic fit between the implant and the surrounding or adjacent cartilage and/or subchondral bone.

In most cases, joint mobility for the repaired joint will range from 60 to 99.9% of normal mobility. The range of motion is improved to 85-99.9%, more preferably between 90-99.9%, most preferably between 95-99.9% and ideally between 98-99.9%.

Further, the incisions required to implant the devices of the invention typically are less than 50% of the incision required to implant currently available implants. For example, a total knee replacement typically employs an incision of from 6-12 inches (15-30 cm) while a unicompartmental knee replacement requires an incision of 3 inches (7 cm). An implant according to this invention designed to repair the tibial surface requires only a 3 cm incision (approximately 1.5 inches), while a combination of implants for repairing both the tibial surface and the femoral condyles requires an incision of 3 inches (7 cm). In another example, a traditional hip replacement surgery requires a single incision of between 6 and 12 inches (15-30 cm), or in the less invasive technique two incisions of 1.5-4 inches (3-9.5 cm). An implant according to this invention designed to repair the acetabulum requires a single incision of from 1.5 inches (3 cm) to 6 inches (30 cm), depending upon whether single or dual surface correction is desired.

Advantages of the present invention can include, but are not limited to, (i) customization of joint repair to an individual patient (e.g. patient specific design or solution), thereby enhancing the efficacy and comfort level following the repair procedure; (ii) eliminating the need for a surgeon to measure the defect to be repaired intraoperatively in some embodiments; (iii) eliminating the need for a surgeon to shape the material during the implantation procedure; (iv) providing methods of evaluating curvature or shape of the repair material based on bone, cartilage or tissue images or based on intraoperative probing techniques; (v) providing methods of repairing joints with only minimal or, in some instances, no loss in bone stock; and (vi) improving postoperative joint congruity.

Thus, the design and use of joint repair material that more precisely fits the defect (e.g., site of implantation) and, accordingly, provides improved repair of the joint is described herein.

As can be appreciated by those of skill in the art an implant is described that is an interpositional articular implant, cartilage defect conforming implant, cartilage projected implant, and/or subchondral bone conforming implant. The implant has a superior surface and an inferior surface. The superior surface opposes a first articular surface of a joint and the inferior surface opposes a second articular surface of the joint and further wherein at least one of the superior or inferior surfaces has a three-dimensional shape that substantially matches the shape of one of the first and second articular surfaces. The implant is suitable for placement within any joint, including the knee, hip, shoulder, elbow, wrist, finger, toe, and ankle. The superior surface and the inferior surface of the implant typically have a three dimensional shape that substantially matches the shape of at least one of the articular surface that the superior surface of the implant abuts and the inferior surface of the articular surface that the implant abuts. The implant is designed to have a thickness of the cartilage defect in a patient, or a fraction thereof, typically between 65% and 99.9%.

The implant can be manufactured from a variety of suitable materials, including biocompatible materials, metals, metal alloys, biologically active materials, polymers, and the like. Additionally, the implant can be manufactured from a plurality of materials, including coatings.

The implant can further have a mechanism for attachment to a joint. Suitable attachment mechanisms include ridges, pegs, pins, cross-members, teeth and protrusions. Additional mechanisms for stabilization of the joint can be provided such as ridges, lips, and thickening along all or a portion of a peripheral surface.

The implant can also be designed such that it has two or more components. These components can be integrally formed, indivisibly formed, interconnectedly formed, and interdependently formed, depending on the desired functionality. In the multiple component scenario, the joint contacting components can be designed to engage the joint slideably or rotatably, or a combination thereof. Alternatively, either or both of the joint contacting components can be fixed to the joint. Any additional components can be integrally formed, indivisibly formed, interconnectedly formed or interdependently formed with any other component that it engages.

Each component of the implant, or the implant itself can have a shape formed along its periphery or perimeter that is circular, elliptical, ovoid, kidney shaped, substantially circular, substantially elliptical, substantially ovoid, and substantially kidney shaped. Additionally, each component of the implant, or the implant itself can have a cross-sectional shape that is spherical, hemispherical, aspherical, convex, concave, substantially convex, and substantially concave.

The design of the implant is such that it is conducive for implantation using an incision of 10 cm or less. Further, the implant is designed to restore the range of motion of the joint to between 80-99.9% of normal joint motion.

The implant, or any component thereof, can have a variety of shapes such that the periphery of the implant can be of greater thickness than a central portion of the implant. Alternatively, the implant, or any component thereof, can be designed so that the central portion of the implant is of greater thickness than a periphery. Looking at the implant from a plurality of directions, such as an anterior portion, posterior portion, lateral portion and medial portion, the implant, or any component thereof, can have a thickness along the posterior portion of the device that is equal to or greater than a thickness of at least one of the lateral, medial and anterior portion of the implant. Alternatively, the implant, or any component thereof, can have a thickness along a posterior portion of the device that is equal to or less than a thickness of at least one of the lateral, medial and anterior portion of the implant. In yet another alternative, the implant, or any component thereof, can have a thickness along a medial portion of the device that is equal to or less than a thickness of at least one of an anterior portion, posterior portion, and lateral portion. In another alternative, the implant can have a thickness along a medial portion of the device that is equal to or greater than a thickness of at least one of an anterior portion, posterior portion, and lateral portion.

Procedures for repairing a joint using the implant described below includes the step of arthroscopically implanting an implant having a superior and inferior surface wherein at least one of the superior or inferior surfaces has a three-dimensional shape that substantially matches the shape of an articular surface. The image can be analyzed prior to implantation. Typically the image is an MRI, CT, x-ray, or a combinations thereof.

The method of making an implant according to this invention includes: determining three-dimensional shapes of one or more articular surface of the joint; and producing an implant having a superior surface and an inferior surface, wherein the superior surface and inferior surface oppose a first and second articular surface of the joint and further wherein at least one of the superior or inferior surfaces substantially matches the three-dimensional shape of the articular surface.

Further, the present invention provides novel devices and methods for replacing a portion (e.g., diseased area and/or area slightly larger than the diseased area) of a joint (e.g., cartilage and/or bone) with an implant material, where the implant achieves an anatomic or near anatomic fit with at least one surface of the surrounding structures and tissues and restores joint mobility to between 60-99.9% of the normal range of motion for the joint. Further, the implants can withstand up to 100% of the shear force exerted on the joint during motion. In cases where the devices and/or methods include an element associated with the underlying articular bone, the invention also provides that the bone-associated element can achieve an anatomic or near anatomic alignment with the subchondral bone. The invention also enables the preparation of an implantation site with a single cut. These devices can be interpositional. The devices can be single component, dual component, or have a plurality of components.

A method of the invention comprises the steps of (a) measuring one or more dimensions (e.g., thickness and/or curvature and/or size) of the intended implantation site or the dimensions of the area surrounding the intended implantation site; and (b) providing cartilage replacement or material that conforms to the measurements obtained in step (a). In certain aspects, step (a) comprises measuring the thickness of the cartilage surrounding the intended implantation site and measuring the curvature of the cartilage surrounding the intended implantation site. Alternatively, step (a) can comprise measuring the size of the intended implantation site and measuring the curvature of the cartilage surrounding the intended implantation site; or measuring the thickness of the cartilage surrounding the intended implantation site, measuring the size of the intended implantation site, and measuring the curvature of the cartilage surrounding the intended implantation site; or reconstructing the shape of healthy cartilage surface at the intended implantation site; or measuring the size of the intended implantation site and/or measuring the curvature or geometry of the subchondral bone at the or surrounding the intended implantation site. In addition, the thickness, curvature or surface geometry of the remaining cartilage at the implantation site can be measured and can, for example, be compared with the thickness, curvature or surface geometry of the surrounding cartilage. This comparison can be used to derive the shape of a cartilage replacement or material more accurately.

The dimensions of the replacement material can be selected following intraoperative measurements, for example measurements made using imaging techniques such as ultrasound, MRI, CT scan, x-ray imaging obtained with x-ray dye and fluoroscopic imaging. A mechanical probe (with or without imaging capabilities) can also be used to selected dimensions, for example an ultrasound probe, a laser, an optical probe, an indentation probe, and a deformable material.

One or more implantable device(s) includes a three-dimensional body. In a knee, the implant can be used in one (unicompartmental) or more (multicompartmental) compartments. In the knee, the implant is not elliptical in shape, but follows the 3D geometry of the articular cartilage, subchondral bone and/or intra-articular structures. The implant has a pair of opposed faces. The contours of one face of the implant matches or substantially match the underlying cartilage and/or bone contour; while the contour of the opposing face of the implant creates a surface for a mating joint surface to interface with. For example, the surface of the opposing face can be projected using modeling to optimize the surface for mating with the joint. In addition, the opposed faces can be connected using a rounded interface. The interface can also extend beyond the articular surface. The implants of the invention can also be self-expandable and amendable to arthroscopic insertion.

Each face of the device is not necessarily uniform in dimension. The length D across one axis taken at any given point is variable along that axis. Similarly the length 2D across the second axis (perpendicular to the first axis) is also variable along that axis as well. The ratio between any D length along a first axis and any D length along a second axis can have any ratio that is suitable for the physical anatomy being corrected and would be appreciated by those of skill in the art.

As will be appreciated by those of skill in the art, any of the implantable joint prostheses described herein can comprise multiple (e.g., two or more pieces) body components that are engageable (e.g., slideably) and/or separable without departing from the scope of the invention. For example, a two-piece component can be provided where each component has a face whose contour conforms, partially or substantially, to the underlying cartilage and/or bone. In certain embodiments, the opposing surfaces of the components that are engageable are curved. The curvature can be selected to be similar to that or mirror that of at least one articular surface for that joint. In other embodiments, the opposing surfaces of the components that are engageable are flat. In other embodiments, the opposing surfaces of the components that are engageable are a combination of flat and curved. The opposing surfaces of the components that are engageable can also be irregular. In this case, they are preferably designed to mate with each other in at least one or more positions.

In any of the methods described herein, the replacement material can be selected (for example, from a pre-existing library of repair systems). Thus, the replacement material can be produced pre-, intra- or post-operatively. Furthermore, in any of the methods described herein the replacement material can also be shaped using appropriate techniques known in the art; either pre-operatively, intra-operatively, or post-operatively. Techniques include: manually, automatically or by machine; using mechanical abrasion including polishing, laser ablation, radiofrequency ablation, extrusion, injection, molding, compression molding and/or machining techniques, or the like. Finally, the implants can comprise one or more biologically active materials such as drug(s), cells, acellular material, pharmacological agents, biological agents, and the like.

The invention includes a method of repairing cartilage in a subject, the method comprising the step of implanting cartilage repair material prepared according to any of the methods described herein. Implantation is typically arthroscopic and can be accomplished via a relatively small incision.

The invention also provides a method of determining the curvature of an articular surface, the method comprising the step of intraoperatively measuring the curvature of the articular surface using a mechanical probe or a surgical mechanical navigation system. The articular surface can comprise cartilage and/or subchondral bone. The mechanical probe (with or without imaging capabilities) can include, for example an ultrasound probe, a laser, a mechanical arm (such as the Titanium FARO arm) an optical probe and/or a deformable material or device.

A variety of tools can be used to facilitate the implantation of the devices. The tools are guides that assist in optimally positioning the device relative to the articular surface. The design of tools and guides for use with the devices is derived from the design of the device suitable for a particular joint. The tools can include trial implants or surgical tools that partially or substantially conform to the implantation site or joint cavity.

Any of the repair systems or prostheses described herein (e.g., the external surface) can comprise a polymeric material or liquid metal. The polymeric material can be attached to a metal or metal alloy. The polymeric material can be injected and, for example, be self hardening or hardening when exposed to a chemical, energy beam, light source, ultrasound and others. Further, any of the systems or prostheses described herein can be adapted to receive injections, for example, through an opening in the external surface of the cartilage replacement material (e.g., an opening in the external surface terminates in a plurality of openings on the bone surface). Bone cement, therapeutics, and/or other bioactive substances can be injected through the opening(s). In certain embodiments, it can be desirable to inject bone cement under pressure onto the articular surface or subchondral bone or bone marrow in order to achieve permeation of portions of the implantation site with bone cement. In addition, any of the repair systems or prostheses described herein can be anchored in bone marrow or in the subchondral bone itself. One or more anchoring extensions (e.g., pegs, etc.) can extend through the bone and/or bone marrow.

In some embodiments, the cartilage replacement system can be implanted without breaching the subchondral bone or with only few pegs or anchors extending into or through the subchondral bone. This technique has the advantage of avoiding future implant "settling" and osteolysis with resultant articular incongruity or implant loosening or other complications.

As will be appreciated by those of skill in the art, suitable joints include knee, shoulder, hip, vertebrae, intervertebral disks, elbow, ankle, wrist, fingers, carpometacarpal, midfoot, and forefoot joints, to name a few. The techniques described likewise are not limited to joints found in humans but can be extended to joints in any mammal.

These and other embodiments of the subject invention will be apparent to those of skill in the art in light of the disclosure herein.

BRIEF DESCRIPTION OF THE DRAWINGS

FIG. 12A is a cross-sectional view of an implant with a member extending into the acetabular fossa. FIGS. 12B-E illustrate a variety of perspective views wherein the implant is hemispherical, partially hemispherical, a rail and a spoke.

FIG. 13A is a cross-sectional view of a dual component "mobile bearing" implant showing a two piece construction and smooth mating surfaces. Plan views are also shown showing dual components with two hemispheres, single hemisphere with a rail or rail-like exterior component (i.e., hemispherical in one dimension, but not in the remaining dimensions), single hemisphere with rail interior structure, single hemisphere with spoke interior component, and single hemisphere with spoke exterior component.

FIGS. 13B-J are alternative embodiments of a dual component implant where the interior surface of the exterior component has a nub that engages with in indent on the exterior surface of the interior component. Additional variations are also shown.

FIGS. 16B-D are cross-sectional views of a triple component "mobile bearing" implant that have one or more components forming a hemisphere while at least one other component does not.

FIG. 17A is a cross-sectional view of a dual component "mobile bearing" implant with a member extending into the acetabular fossa. FIG. 17B and FIG. 17C show cross-sectional embodiments, where one of the components forms a hemisphere while the second component does not.

FIG. 18A is a cross-sectional view of a dual component "mobile bearing" implant with a member extending into the acetabular fossa. FIG. 18B is a view from the top showing four fins on top of the member shown in FIG. 18A extending into the acetabular fossa on top of the acetabular component.

FIG. 19A is a cross-sectional view of a dual component "mobile bearing" implant with a member extending into the fovea capitis of the femoral head. FIG. 19B is a cross-sectional view of a dual component fixed implant.

arthroplasty device with the humeral surface conforming substantially to the shape of the humeral head and the glenoid surface conforming substantially to the shape of the glenoid.

Figure 21A:
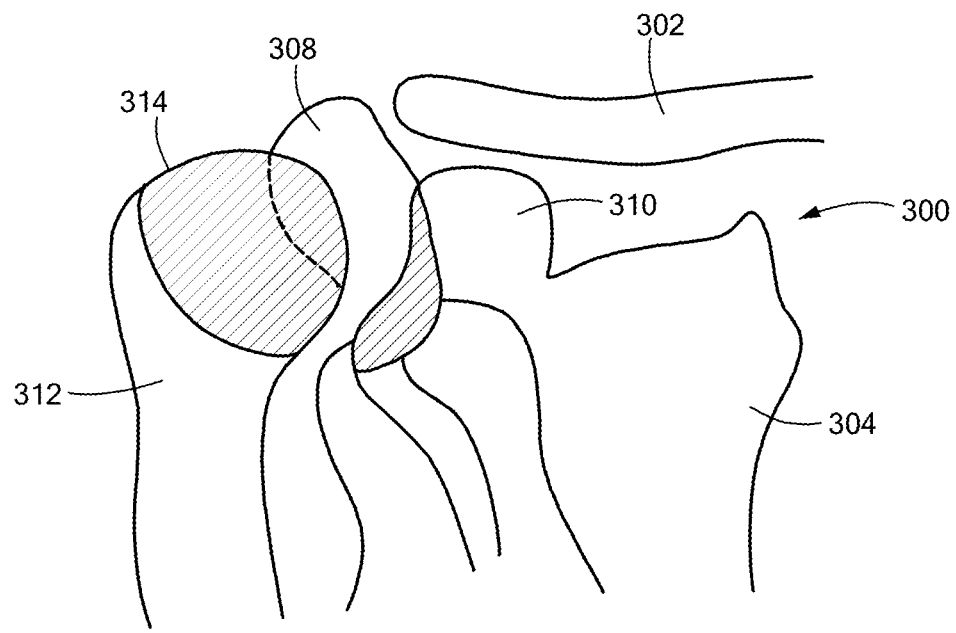
FIG. 21A is a frontal view of the osseous structures in the shoulder joint such as the clavicle, scapula, glenoid fossa, acromion, coracoid process and humerus.
Figure 21B:
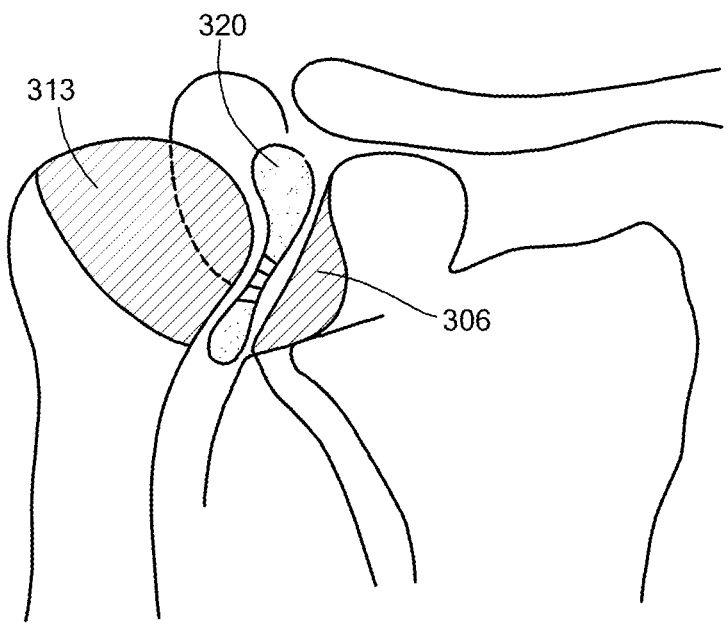
FIG. 21B is a view of an arthroplasty device placed between the humeral head and the glenoid fossa.
Figure 21C:
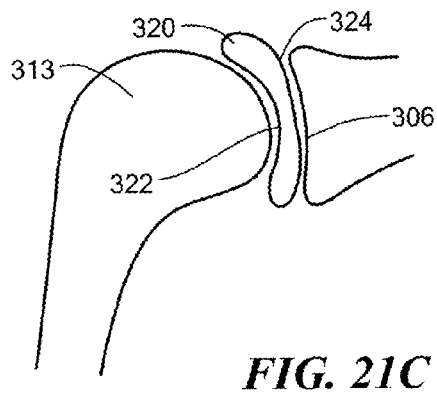
FIG. 21C is an oblique frontal cross-sectional view of an arthroplasty device with the humeral surface conforming substantially to the shape of the humeral head and the glenoid surface conforming substantially to the shape of the glenoid.
Figure 21D:
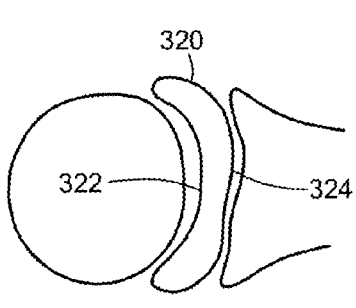
FIG. 21D is an axial cross-sectional view of an arthroplasty device with the humeral surface conforming substantially to the shape of the humeral head and the glenoid surface conforming substantially to the shape of the glenoid.
Figure 21E:
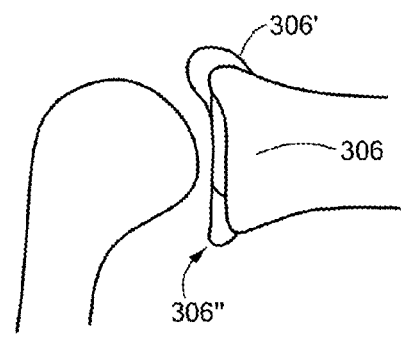
FIG. 21E is an oblique frontal view of the shoulder demonstrating the articular cartilage and the superior and inferior glenoid labrum.
Figure 21F:
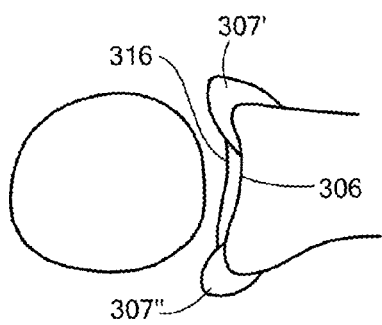
FIG. 21F is an axial view of the shoulder demonstrating the articular cartilage and the anterior and posterior glenoid labrum.
Figure 21G:
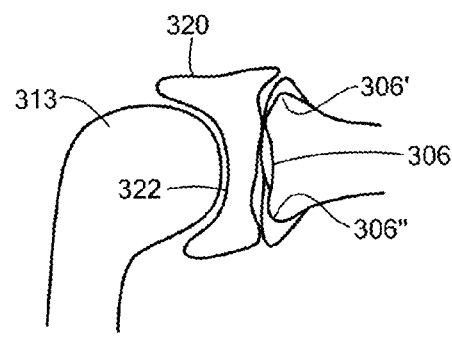
FIG. 21G is an oblique frontal cross-sectional view of an arthroplasty device with the humeral surface conforming substantially to the shape of the humeral head and the glenoid surface conforming substantially to the shape of the glenoid and the glenoid labrum.
Figure 21H:
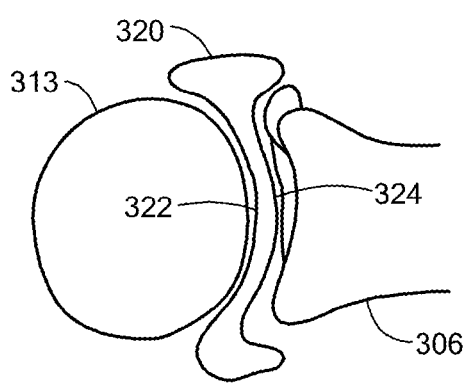
FIG. 21H is an axial cross-sectional view of an arthroplasty with the humeral surface conforming substantially to the shape of the humeral head and the glenoid surface conforming substantially to the shape of the glenoid and the glenoid labrum.
Figure 21I:
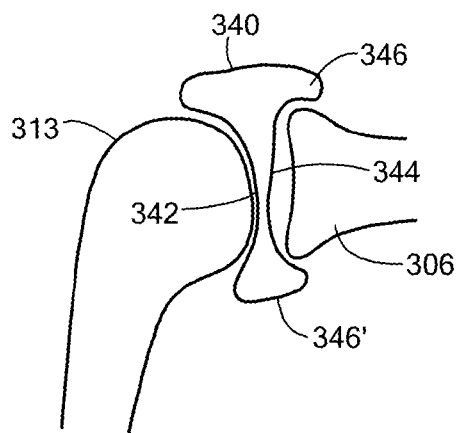
FIG. 21I is an oblique frontal cross-sectional view of an arthroplasty device with the humeral surface conforming substantially to the shape of the humeral head and the glenoid surface conforming substantially to the shape of the glenoid. A lip is shown extending superiorly and/or inferiorly which provides stabilization over the glenoid.
Figure 21J:
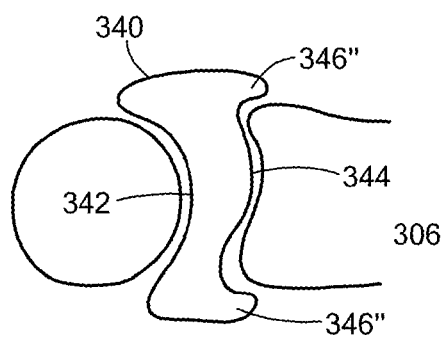
FIG. 21J is an axial cross-sectional view of an arthroplasty device with the humeral surface conforming substantially to the shape of the humeral head and the glenoid surface conforming substantially to the shape of the glenoid. A lip is shown extending anteriorly and/or posteriorly which provides stabilization over the glenoid.
Figure 21K:
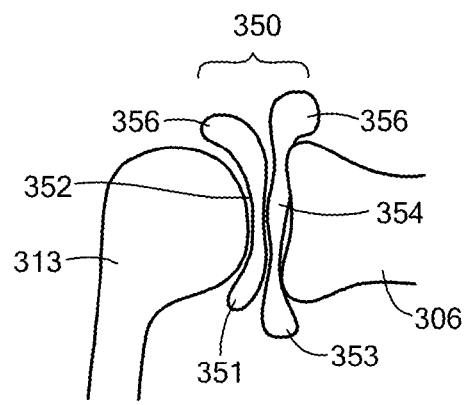
FIG. 21K is an oblique frontal cross-sectional view of a dual component, "mobile-bearing"
Figure 21L:
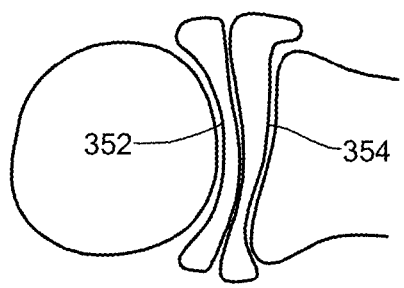
Figure 21M:
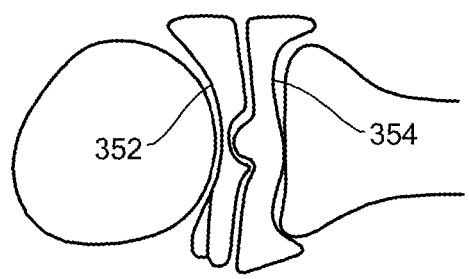

FIG. 21L is an axial cross-sectional view of a dual component, "mobile-bearing" arthroplasty device with a humeral conforming surface that conforms to the shape of the humeral head and a glenoid conforming surface that conforms to the shape of the glenoid. FIG. 21M is an alternate view of a dual component, "mobile-bearing" arthroplasty device with a humeral conforming surface that conforms to the shape of the humeral head and a glenoid conforming surface that conforms to the shape of the glenoid. The device has a nub on the surface of the first component that mates with an indent on the surface of the second component to enhance joint movement.

Figure 21N:
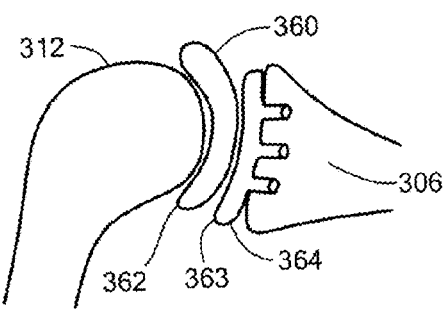
Figure 21O:
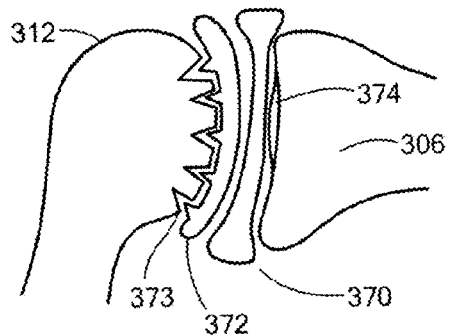
Figure 21P:
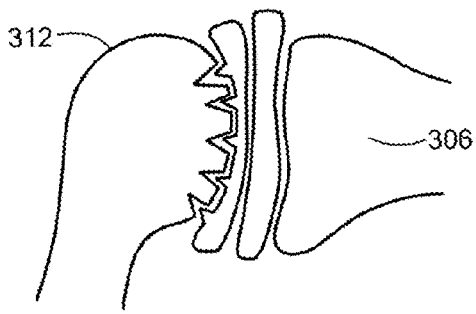

FIG. 21N is an oblique frontal cross-sectional view of a dual component, "mobile-bearing" arthroplasty device. FIG. 21O is an oblique frontal cross-sectional view of a dual component, "mobile-bearing" arthroplasty device. FIGS. 21P and Q are cross-sectional views of alternate embodiments of the dual mobile bearing device shown in FIG. 21O.

Figure 22:
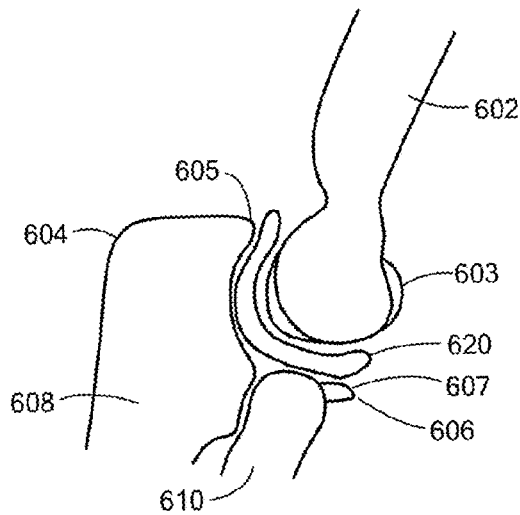

FIG. 22 is an oblique longitudinal view through the elbow joint demonstrating the distal humerus, the olecranon and the radial head. The cartilaginous surfaces are also shown.

Figure 23A:
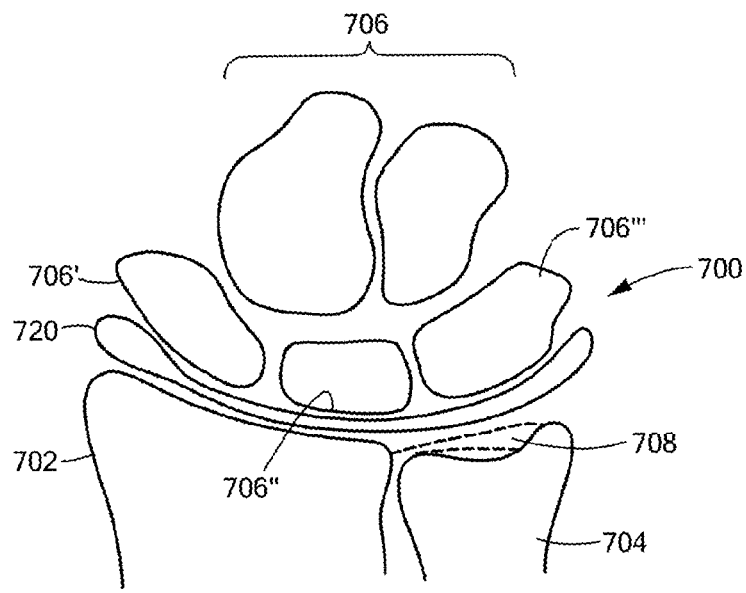
Figure 23B:
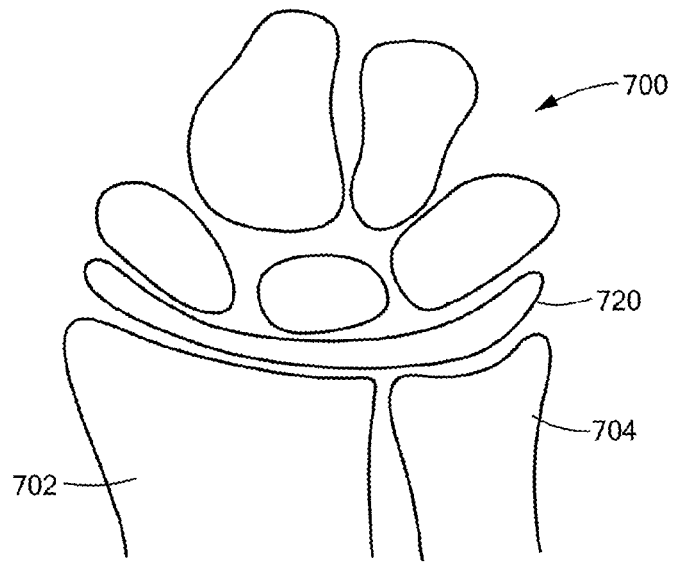
Figure 23C:
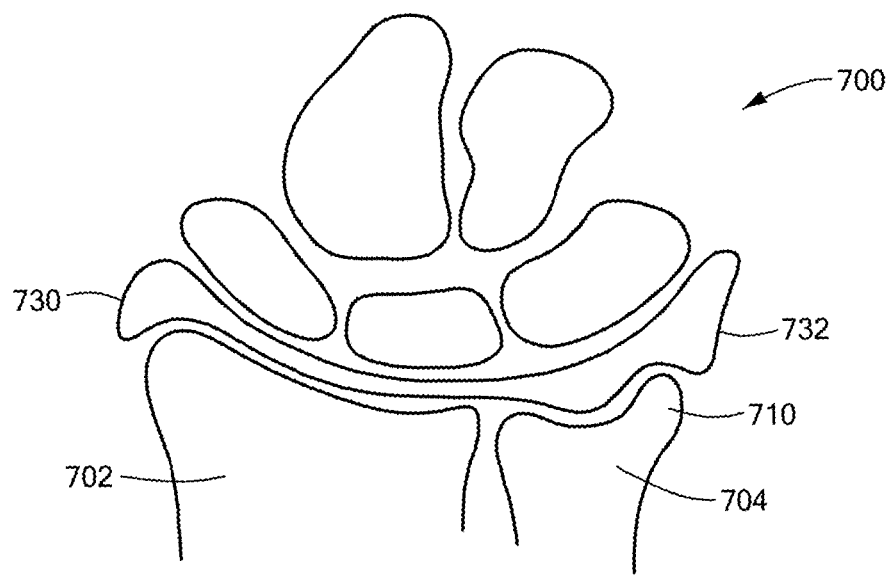
Figure 23D:
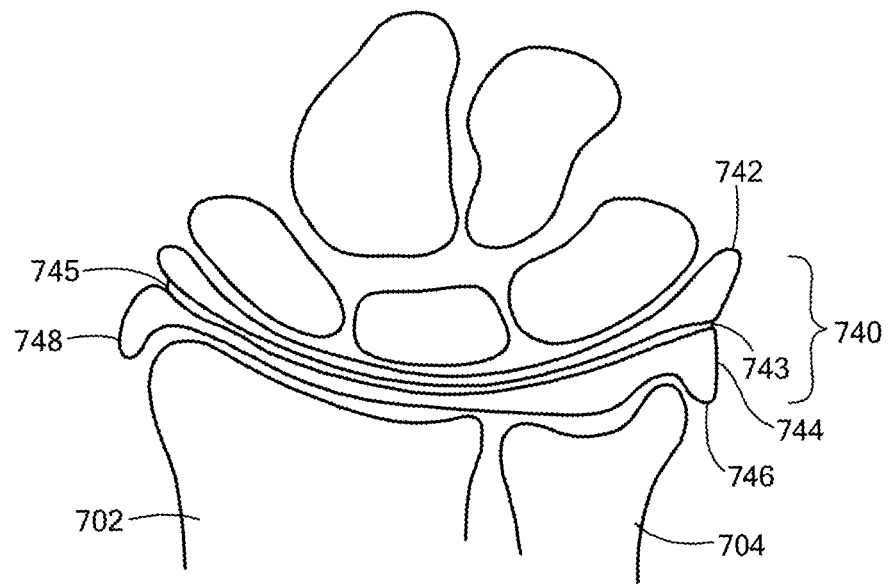
Figure 23E:
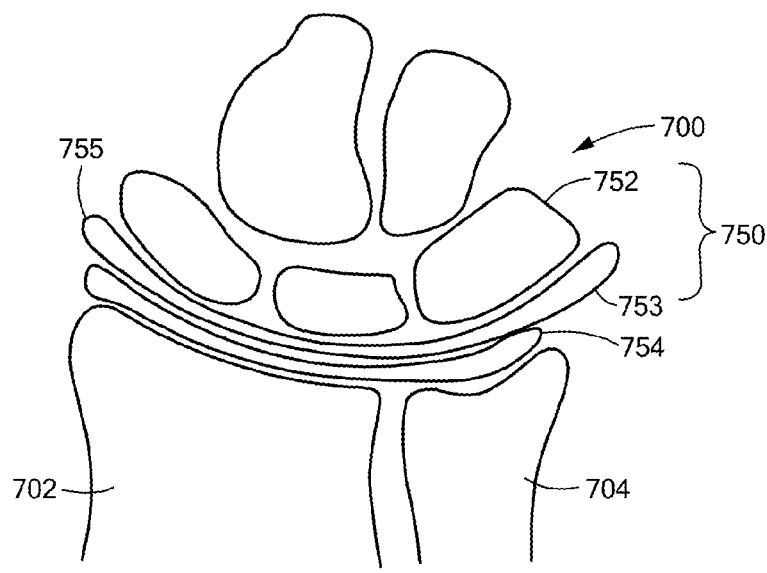
Figure 23F:
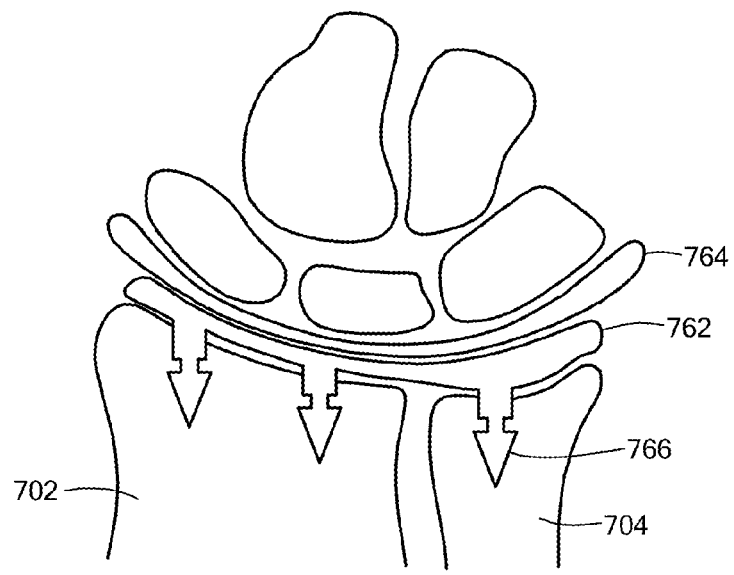

FIG. 23A is a longitudinal view through the wrist joint demonstrating the distal radius, the ulna and several of the carpal bones with an arthroplasty system in place. FIG. 23B is a longitudinal view through the wrist joint demonstrating the distal radius, the ulna and several of the carpal bones with an arthroplasty system in place. FIG. 23C is a longitudinal view through the wrist joint demonstrating the distal radius, the ulna and several of the carpal bones with an arthroplasty system in place. FIG. 23D is a longitudinal view of a dual component, "mobile-bearing" arthroplasty device suitable for the wrist. FIG. 23E is a longitudinal view of another dual component arthroplasty device, in this case without lips. FIG. 23F is a longitudinal view of a dual component, "mobile-bearing" arthroplasty device.

Figure 24:
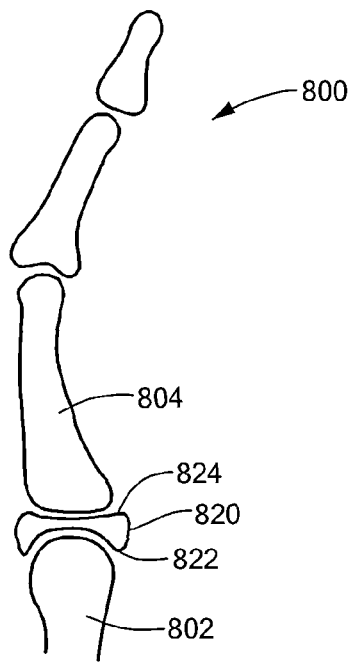

FIG. 24 is a sagittal view through a finger. An arthroplasty device is shown interposed between the metacarpal head and the base of the proximal phalanx.

FIG. 25 A is a sagittal view through the ankle joint demonstrating the distal tibia, the talus and calcaneus and the other bones with an arthroplasty system in place. FIG. 25 B is a coronal view through the ankle joint demonstrating the distal tibia, the distal fibula and the talus. An arthroplasty device is shown interposed between the distal tibia and the talar dome. FIG. 25C is a sagittal view through the ankle joint demonstrating the distal tibia, the talus and calcaneus and the other bones. The cartilaginous surfaces are also shown. An arthroplasty device is shown interposed between the distal tibia and the talar dome. FIG. 25D is a coronal view through the ankle joint demonstrating the distal tibia, the distal fibula and the talus. An arthroplasty device is shown interposed between the distal tibia and the talar dome.

Figure 26:
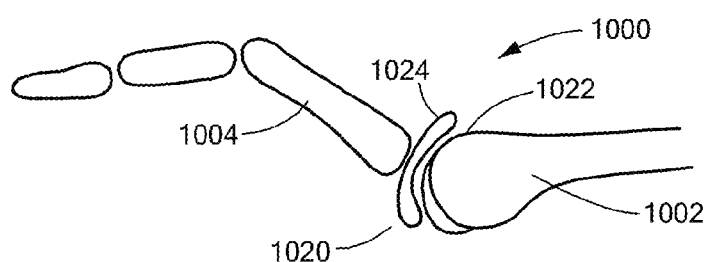

FIG. 26 is a sagittal view through a toe. An arthroplasty device is shown interposed between the metatarsal head and the base of the proximal phalanx.

FIGS. 27 A-D are block diagrams of method steps employed while implanting an device of the invention into a target joint.

Figure 8A:
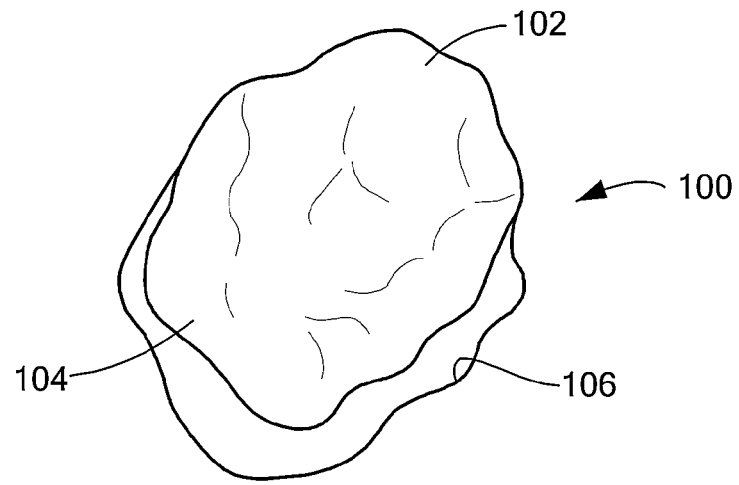
FIG. 8 A is a perspective view of a joint implant of the invention suitable for implantation at the tibial plateau of the knee joint.
FIG. 8B is a top view of the implant of FIG. 8A.
FIG. 8C is a cross-sectional view of the implant of FIG. 8B along the lines C-C shown in FIG. 8B.
FIG. 8D is a cross-sectional view along the lines D-D shown in FIG. 8 B.
FIG. 8E is a cross-sectional view along the lines E-E shown in FIG. 8 B.
FIG. 8F is a side view of the implant of FIG. 8A.
FIG. 8G is a cross-sectional view of the implant of FIG. 8A shown implanted taken along a plane parallel to the sagittal plane.
FIG. 8H is a cross-sectional view of the implant of FIG. 8A shown implanted taken along a plane parallel to the coronal plane.
FIG. 8I is a cross-sectional view of the implant of FIG. 8A shown implanted taken along a plane parallel to the axial plane.
FIG. 8J shows a slightly larger implant that extends closer to the bone medially (towards the edge of the tibial plateau) and anteriorly and posteriorly.
FIG. 8K is a side view of an alternate embodiment of the joint implant of FIG. 8A showing an anchor.
FIG. 8L is a bottom view of an alternate embodiment of the joint implant of FIG. 8 A showing an anchor.
FIGS. 8M and N illustrate alternate embodiments of a two piece implant from a front view and a side view.
Figure 8B:
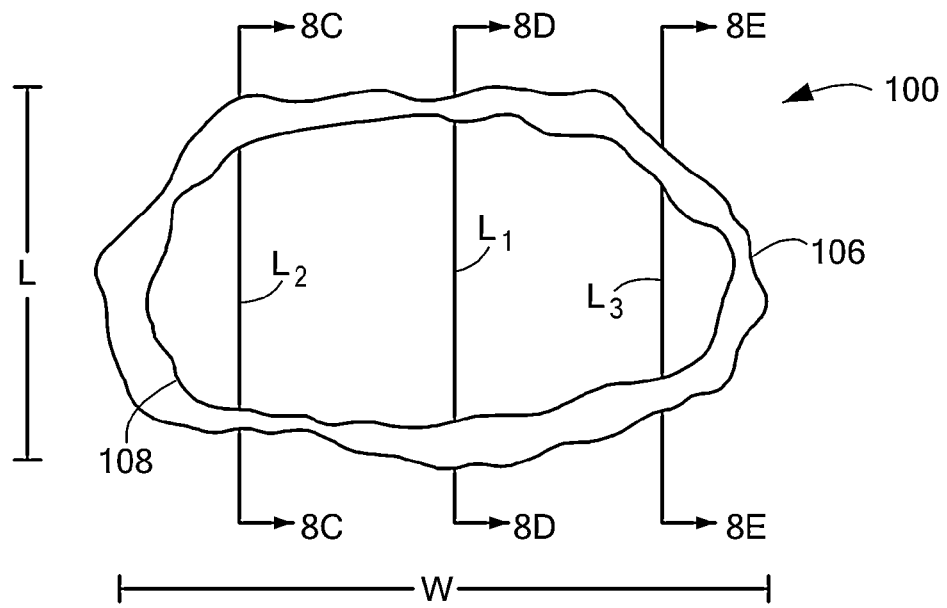
Figure 8E:
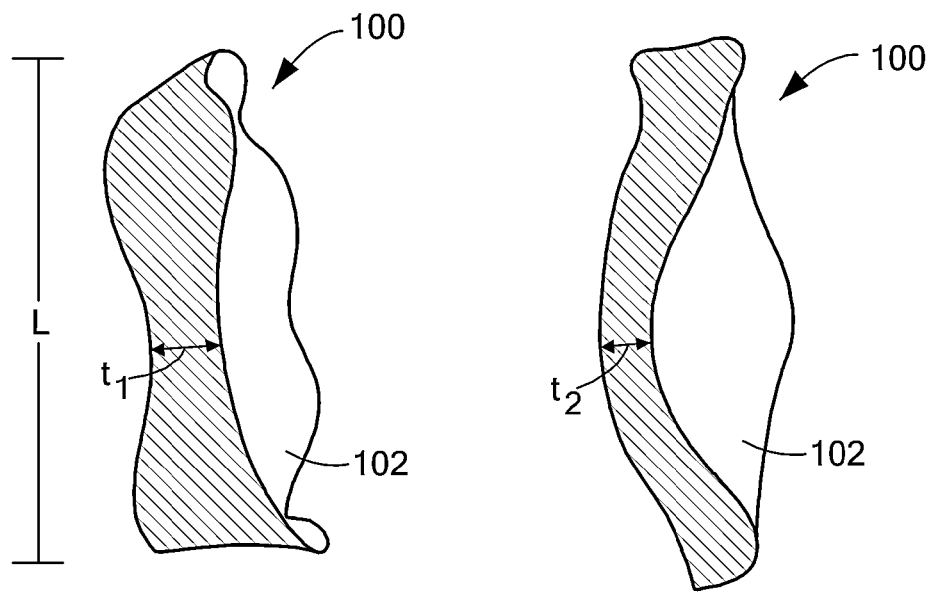
Figure 8E:
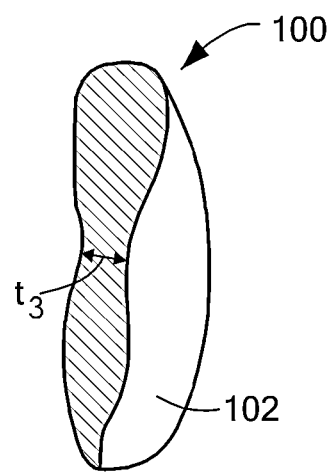
Figure 8F:
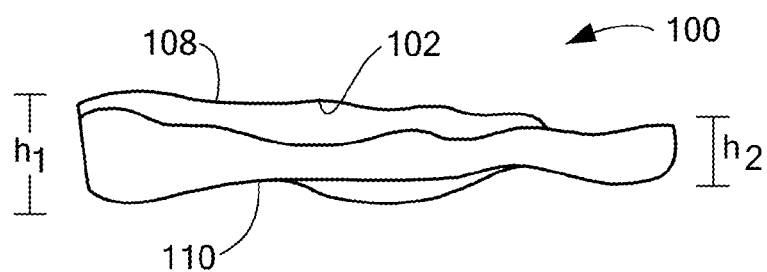
Figure 8G:
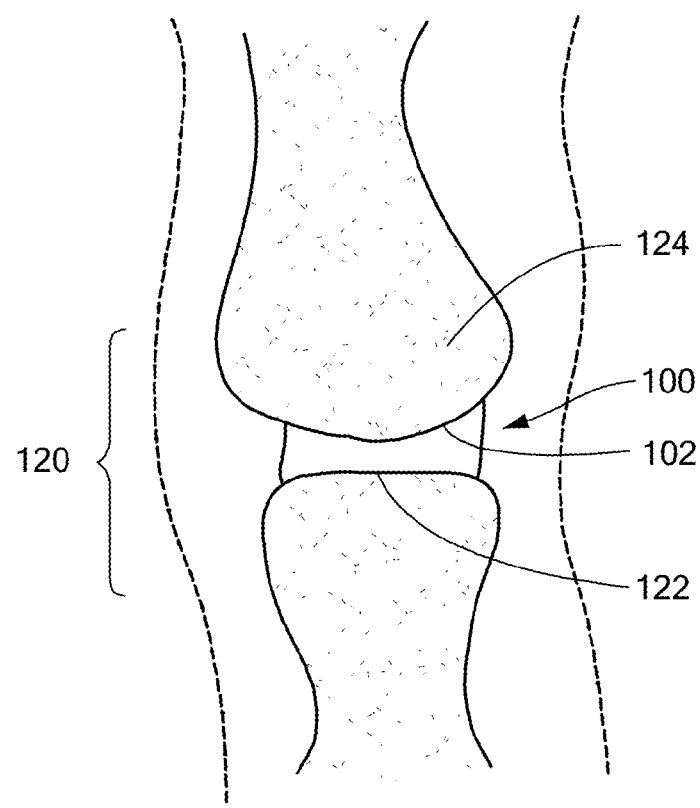
Figure 8H:
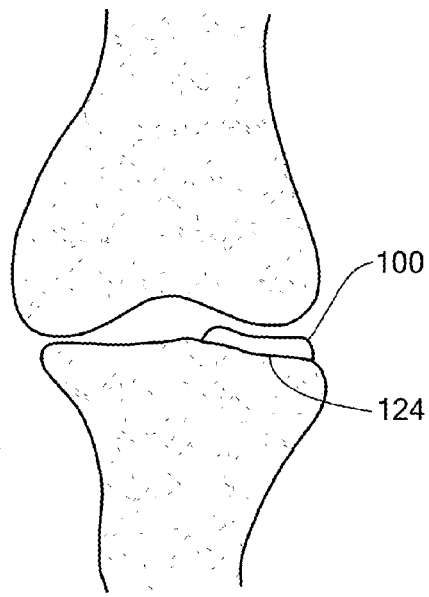
Figure 8I:
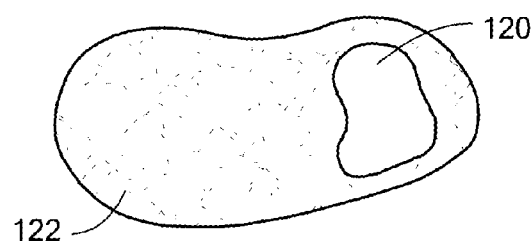
Figure 8J:
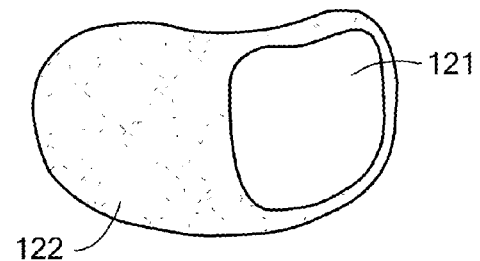
Figure 8K:
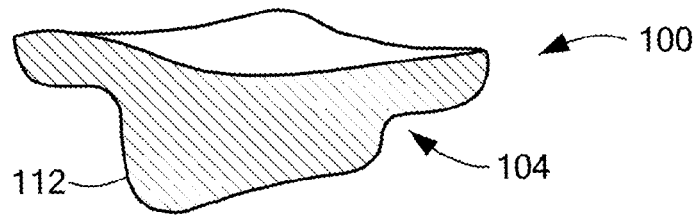
Figure 8L:
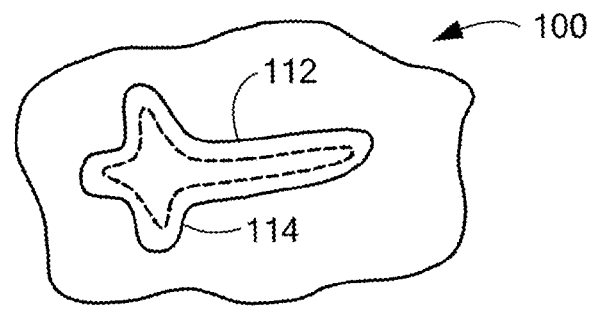
Figure 9A:
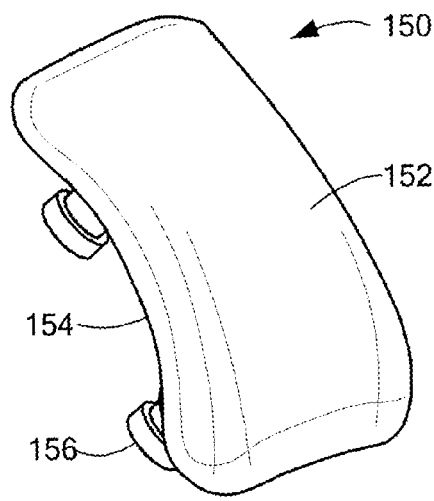
FIGS. 9A and B are perspective views of a joint implant suitable for use on a condyle of the femur from the inferior and superior surface viewpoints, respectively.
Figure 9B:
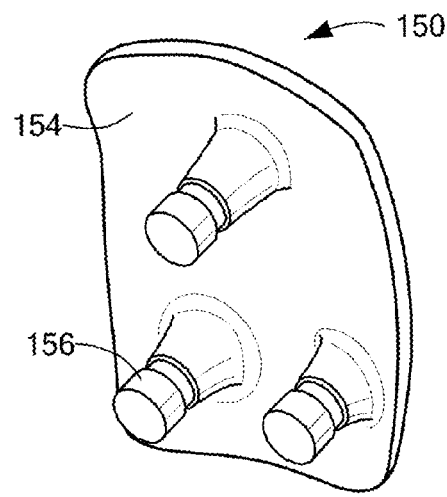
FIG. 9C is a side view of the implant of FIG. 9A.
FIG. 9D is a view of the inferior surface of the implant.
FIG. 9E is a view of the superior surface of the implant and FIG. 9F is a cross-section of the implant.
FIG. 9G is a view of the superior surface of a joint implant suitable for use on both condyles of the femur.
FIG. 9H is a perspective side view of the implant of FIG. 9G.

FIG. 28 is a plan view of an implant guide tool suitable for use implanting the device shown in FIG. 8L FIGS. 29A and B are a plan views of an implant guide tool suitable for use implanting the device shown in FIG. 9B.

DETAILED DESCRIPTION OF THE INVENTION

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference.

As will be appreciated by those of skill in the art, the practice of the present invention employs, unless otherwise indicated, conventional methods of x-ray imaging and processing, x-ray tomosynthesis, ultrasound including A-scan, B-scan and C-scan, computed tomography (CT scan), magnetic resonance imaging (MRI), optical coherence tomography, single photon emission tomography (SPECT) and positron emission tomography (PET) within the skill of the art. Such techniques are explained fully in the literature and need not be described herein. See, e.g., X-Ray Structure Determination: A Practical Guide, 2nd Edition, editors Stout and Jensen, 1989, John Wiley & Sons, publisher; Body CT: A Practical Approach, editor Slone, 1999, McGraw-Hill publisher; X-ray Diagnosis: A Physician's Approach, editor Lam, 1998 Springer-Verlag, publisher; and Dental Radiology: Understanding the X-Ray Image, editor Laetitia Brocklebank 1997, Oxford University Press publisher.

I. Dual or Multiple Surface Assessment of the Joint

The invention allows, among other things, a practitioner to evaluate and treat defects to joints resulting from, for example, joint disease, cartilage degeneration, osteoarthritis, seropositive and seronegative arthritides, bone damages, cartilage damage, trauma, and/or degeneration due to overuse or age. The size, volume and shape of the area of interest can include only the region of cartilage that has the defect, but preferably can also include contiguous parts of the cartilage surrounding the cartilage defect. Moreover, the size, volume and shape of the area of interest can include subchondral bone, bone marrow and other articular structures, e.g. menisci, ligaments and tendons.

Figure 1A:
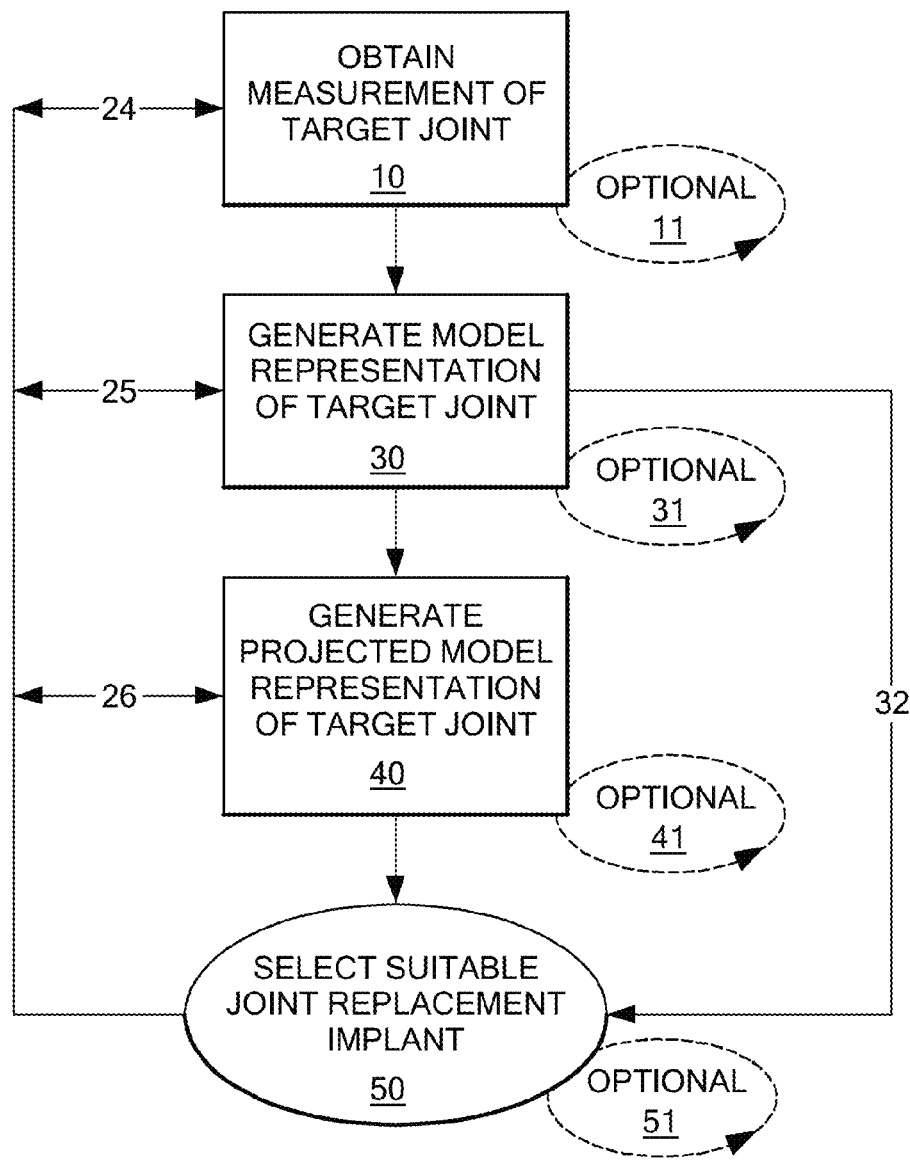
FIG. 1A is a block diagram of a method for assessing a joint in need of repair according to the invention wherein the existing joint surface is unaltered, or substantially unaltered, prior to receiving the selected implant.

FIG. 1A is a flow chart showing steps taken by a practitioner in assessing a joint. First, a practitioner obtains a measurement of a target joint 10. The step of obtaining a measurement can be accomplished by taking an image of the joint. This step can be repeated, as necessary, 11 to obtain a plurality of images in order to further refine the joint assessment process. Once the practitioner has obtained the necessary measurements, the information is used to generate a model representation of the target joint being assessed 30. This model representation can be in the form of a topographical map or image. The model representation of the joint can be in one, two, or three dimensions. It can include a physical model. More than one model can be created 31, if desired. Either the original model, or a subsequently created model, or both can be used. After the model representation of the joint is generated 30, the practitioner can optionally generate a projected model representation of the target joint in a corrected condition 40. Again, this step can be repeated 41, as necessary or desired. Using the difference between the topographical condition of the joint and the projected image of the joint, the practitioner can then select a joint implant 50 that is suitable to achieve the corrected joint anatomy. As will be appreciated by those of skill in the art, the selection process 50 can be repeated 51 as often as desired to achieve the desired result.

As will be appreciated by those of skill in the art, the practitioner can proceed directly from the step of generating a model representation of the target joint 30 to the step of selecting a suitable joint replacement implant 50 as shown by the arrow 32. Additionally, following selection of suitable joint replacement implant 50, the steps of obtaining measurement of target joint 10, generating model representation of target joint 30 and generating projected model 40, can be repeated in series or parallel as shown by the flow 24, 25, 26.

Figure 1B:
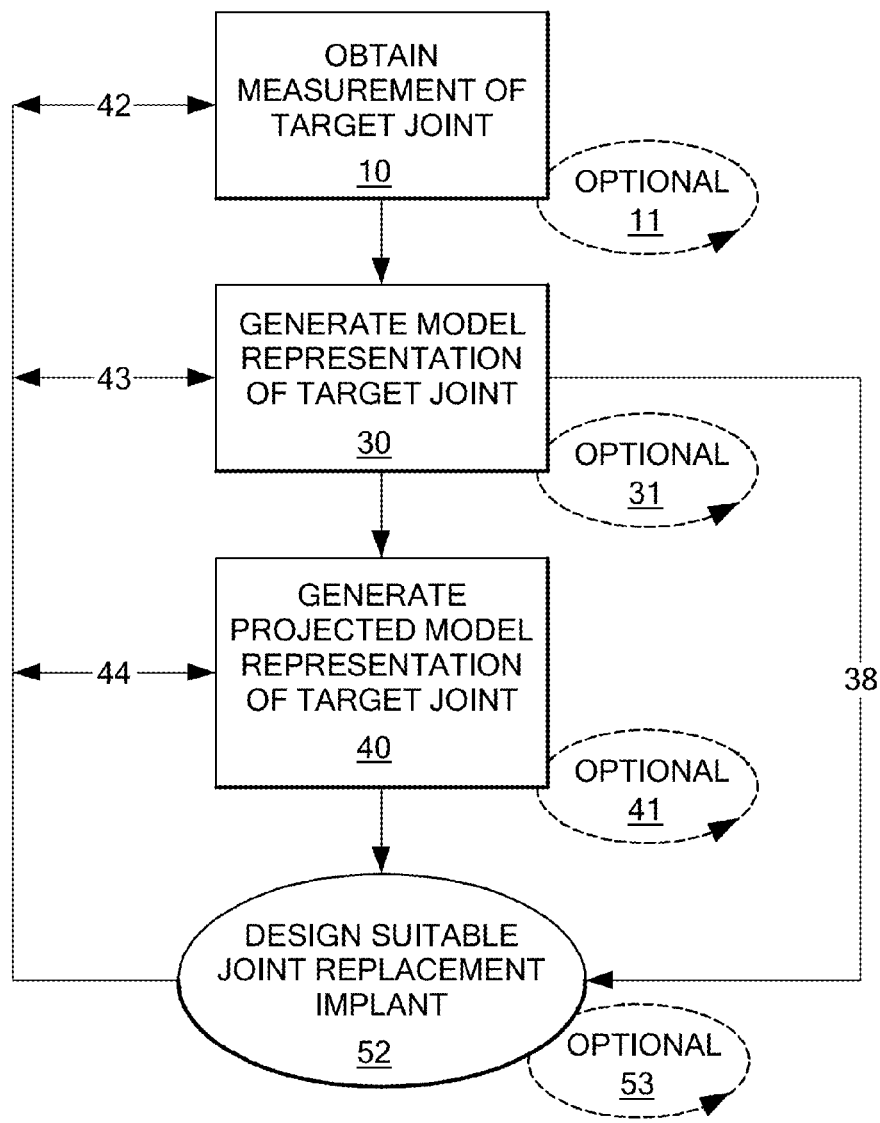
FIG. 1B is a block diagram of a method for assessing a joint in need of repair according to the invention wherein the existing joint surface is unaltered, or substantially unaltered, prior to designing an implant suitable to achieve the repair.

FIG. 1B is an alternate flow chart showing steps taken by a practitioner in assessing a joint. First, a practitioner obtains a measurement of a target joint 10. The step of obtaining a measurement can be accomplished by taking an image of the joint. This step can be repeated, as necessary, 11 to obtain a plurality of images in order to further refine the joint assessment process. Once the practitioner has obtained the necessary measurements, the information is used to generate a model representation of the target joint being assessed 30. This model representation can be in the form of a topographical map or image. The model representation of the joint can be in one, two, or three dimensions. The process can be repeated 31 as necessary or desired. It can include a physical model. After the model representation of the joint is assessed 30, the practitioner can optionally generate a projected model representation of the target joint of the joint in a corrected condition 40. This step can be repeated 41 as necessary or desired. Using the difference between the topographical condition of the joint and the projected image of the joint, the practitioner can then design a joint implant 52 that is suitable to achieve the corrected joint anatomy, repeating the design process 53 as often as necessary to achieve the desired implant design. The practitioner can also assess whether providing additional features, such as lips, pegs, or anchors, will enhance the implants' performance in the target joint.

As will be appreciated by those of skill in the art, the practitioner can proceed directly from the step of generating a model representation of the target joint 30 to the step of designing a suitable joint replacement implant 52 as shown by the arrow 38. Similar to the flow shown above, following the design of a suitable joint replacement implant 52, the steps of obtaining measurement of target joint 10, generating model representation of target joint 30 and generating projected model 40, can be repeated in series or parallel as shown by the flow 42, 43, 44.

The joint implant selected or designed achieves anatomic or near anatomic fit with the existing surface of the joint while presenting a mating surface for the opposing joint surface that replicates the natural joint anatomy. In this instance, both the existing surface of the joint can be assessed as well as the desired resulting surface of the joint. This technique is particularly useful for implants that are not anchored into the bone.

Figure 2:
FIG. 2 is a reproduction of a three-dimensional thickness map of the articular cartilage of the distal femur. Three-dimensional thickness maps can be generated, for example, from ultrasound, CT or MRI data. Dark holes within the substances of the cartilage indicate areas of full thickness cartilage loss.

FIG. 2 illustrates a reproduction of a 3-dimensional thickness map of the articular cartilage of the distal femur. Three-dimensional thickness maps can be generated, for example, from ultrasound, CT, or MRI data. Dark holes within the substance of the cartilage indicate areas of full thickness cartilage loss. From the 3-dimensional thickness map a determination can be made of the size and shape of cartilage damage.

As will be appreciated by those of skill in the art, size, curvature and/or thickness measurements can be obtained using any suitable technique. For example, one dimensional, two dimensional, and/or in three dimensional measurements can be obtained using suitable mechanical means, laser devices, electromagnetic or optical tracking systems, molds, materials applied to the articular surface that harden and "memorize the surface contour," and/or one or more imaging techniques known in the art. Measurements can be obtained non-invasively and/or intraoperatively (e.g., using a probe or other surgical device). As will be appreciated by those of skill in the art, the thickness of the repair device can vary at any given point depending upon the depth of the damage to the cartilage and/or bone to be corrected at any particular location on an articular surface.

A. Imaging Techniques

As will be appreciated by those of skill in the art, imaging techniques suitable for measuring thickness and/or curvature (e.g., of cartilage and/or bone) or size of areas of diseased cartilage or cartilage loss include the use of x-rays, magnetic resonance imaging (MRI), computed tomography scanning (CT, also known as computerized axial tomography or CAT), optical coherence tomography, SPECT, PET, ultrasound imaging techniques, and optical imaging techniques. (See, also, International Patent Publication WO 02/22014 to Alexander, et al., published Mar. 21, 2002; U.S. Pat. No. 6,373,250 to Tsoref et al., issued Apr. 16, 2002; and Vandeberg et al. (2002) Radiology 222:430-436). Contrast or other enhancing agents can be used using any route of administration, e.g. intravenous, intra-articular, etc.

In certain embodiments, CT or MRI is used to assess tissue, bone, cartilage and any defects therein, for example cartilage lesions or areas of diseased cartilage, to obtain information on subchondral bone or cartilage degeneration and to provide morphologic or biochemical or biomechanical information about the area of damage. Specifically, changes such as fissuring, partial or full thickness cartilage loss, and signal changes within residual cartilage can be detected using one or more of these methods. For discussions of the basic NMR principles and techniques, see MRI Basic Principles and Applications, Second Edition, Mark A. Brown and Richard C. Semelka, Wiley-Liss, Inc. (1999). For a discussion of MRI including conventional T1 and T2-weighted spin-echo imaging, gradient recalled echo (GRE) imaging, magnetization transfer contrast (MTC) imaging, fast spin-echo (FSE) imaging, contrast enhanced imaging, rapid acquisition relaxation enhancement, (RARE) imaging, gradient echo acquisition in the steady state, (GRASS), and driven equilibrium Fourier transform (DEFT) imaging, to obtain information on cartilage, see Alexander, et al., WO 02/22014. Thus, in preferred embodiments, the measurements obtained are based on three-dimensional images obtained of the joint as described in Alexander, et al., WO 02/22014 or sets of two-dimensional images ultimately yielding 3D information. Two-dimensional, three-dimensional images, or maps, of the cartilage alone or in combination with a movement pattern of the joint, e.g. flexion-extension, translation and/or rotation, can be obtained. Three-dimensional images can include information on movement patterns, contact points, contact zone of two or more opposing articular surfaces, and movement of the contact point or zone during joint motion. Two and three-dimensional images can include information on biochemical composition of the articular cartilage. In addition, imaging techniques can be compared over time, for example to provide up-to-date information on the shape and type of repair material needed.

Any of the imaging devices described herein can also be used intra-operatively (see, also below), for example using a hand-held ultrasound and/or optical probe to image the articular surface intra-operatively.

B. Intraoperative Measurements

Alternatively, or in addition to, non-invasive imaging techniques described above, measurements of the size of an area of diseased cartilage or an area of cartilage loss, measurements of cartilage thickness and/or curvature of cartilage or bone can be obtained intraoperatively during arthroscopy or open arthrotomy. Intraoperative measurements may or may not involve actual contact with one or more areas of the articular surfaces.

Devices suitable for obtaining intraoperative measurements of cartilage or bone or other articular structures, and to generate a topographical map of the surface include but are not limited to, Placido disks and laser interferometers, and/or deformable materials or devices. (See, for example, U.S. Pat. No. 6,382,028 to Wooh et al., issued May 17, 2002; U.S. Pat. No. 6,057,927 to Levesque et al., issued May 2, 2000; U.S. Pat. No. 5,523,843 to Yamane et al. issued Jun. 4, 1996; U.S. Pat. No. 5,847,804 to Sarver et al. issued Dec. 8, 1998; and U.S. Pat. No. 5,684,562 to Fujeda, issued Nov. 4, 1997).

Figure 3A:
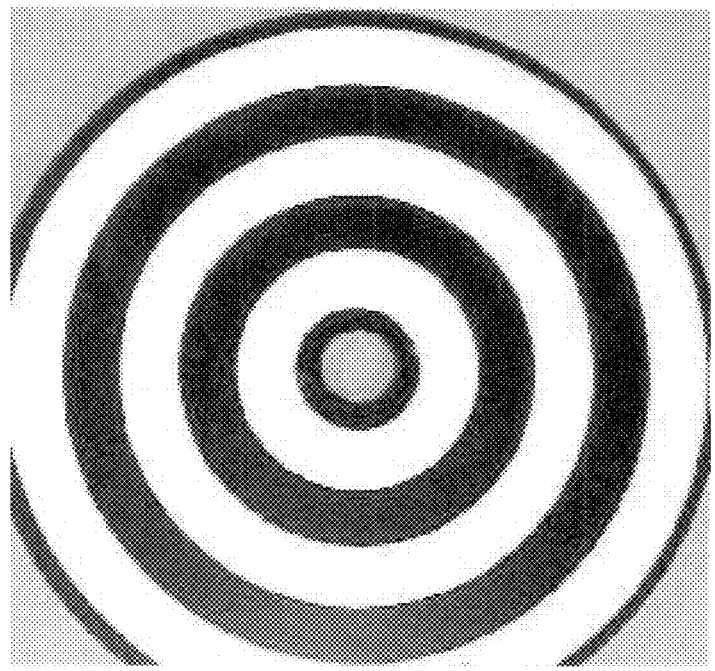
FIG. 3A illustrates an example of a Placido disk of concentrically arranged circles of light.
Figure 3B:
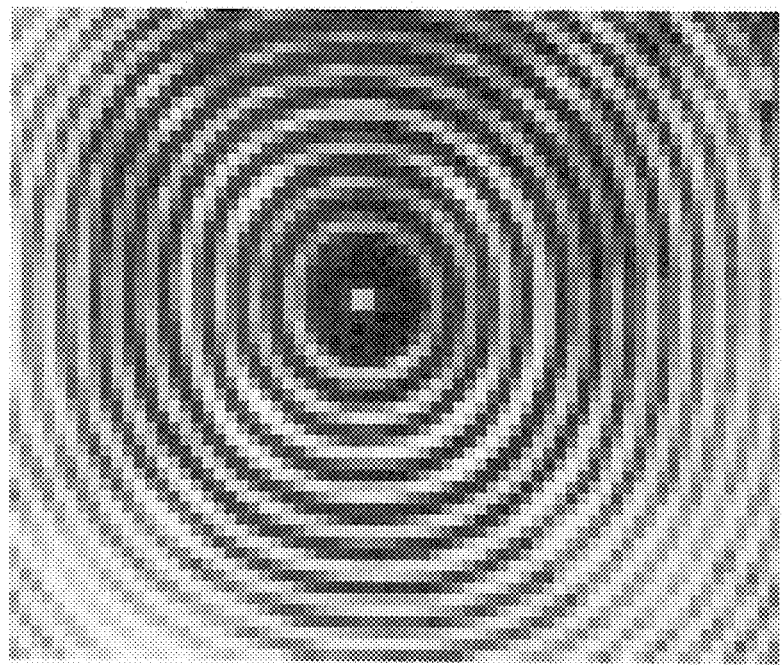
FIG. 3B illustrates an example of a projected Placido disk on a surface of fixed curvature.

FIG. 3A illustrates a Placido disk of concentrically arranged circles of light. The concentric arrays of the Placido disk project well-defined circles of light of varying radii, generated either with laser or white light transported via optical fiber. The Placido disk can be attached to the end of an endoscopic device (or to any probe, for example a hand-held probe) so that the circles of light are projected onto the cartilage surface. FIG. 3B illustrates an example of a Placido disk projected onto the surface of a fixed curvature. One or more imaging cameras can be used (e.g., attached to the device) to capture the reflection of the circles. Mathematical analysis is used to determine the surface curvature. The curvature can then, for example, be visualized on a monitor as a color-coded, topographical map of the cartilage surface. Additionally, a mathematical model of the topographical map can be used to determine the ideal surface topography to replace any cartilage defects in the area analyzed. This computed, ideal surface can then also be visualized on the monitor such as the 3-dimensional thickness map shown in FIG. 2, and can be used to select the curvature of the surfaces of the replacement material or regenerating material.

Figure 4:
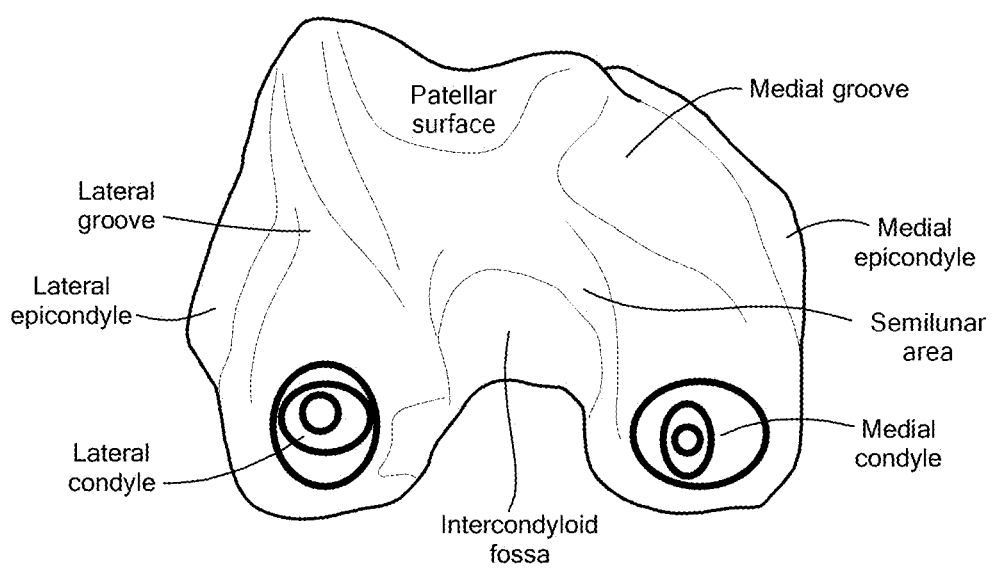
FIG. 4 shows a reflection resulting from a projection of concentric circles of light (Placido Disk) on each femoral condyle, demonstrating the effect of variation in surface contour on the reflected circles.

FIG. 4 shows a reflection resulting from the projection of concentric circles of light (Placido disk) on each femoral condyle, demonstrating the effect of variation in surface contour on reflected circles.

Similarly a laser interferometer can also be attached to the end of an endoscopic device. In addition, a small sensor can be attached to the device in order to determine the cartilage surface or bone curvature using phase shift interferometry, producing a fringe pattern analysis phase map (wave front) visualization of the cartilage surface. The curvature can then be visualized on a monitor as a color coded, topographical map of the cartilage surface. Additionally, a mathematical model of the topographical map can be used to determine the ideal surface topography to replace any cartilage or bone defects in the area analyzed. This computed, ideal surface, or surfaces, can then be visualized on the monitor, and can be used to select the curvature, or curvatures, of the replacement cartilage.

Figure 5:
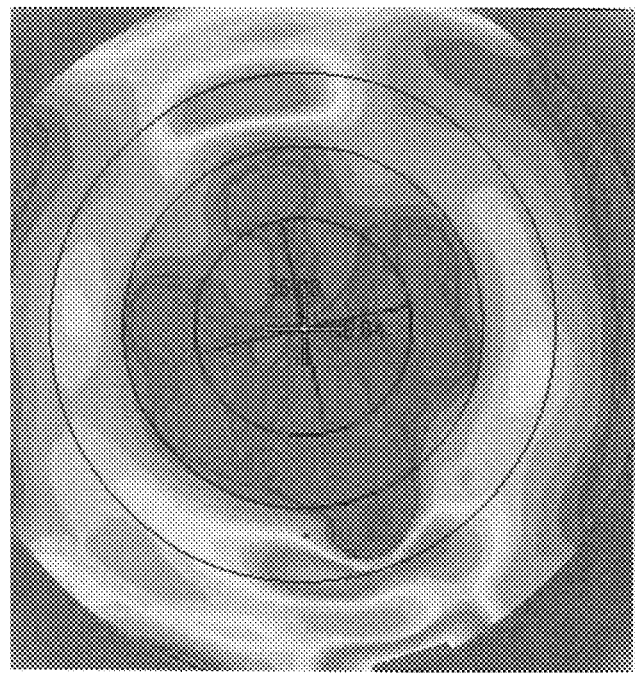
FIG. 5 illustrates an example of a 2D topographical map of an irregularly curved surface.
Figure 6:
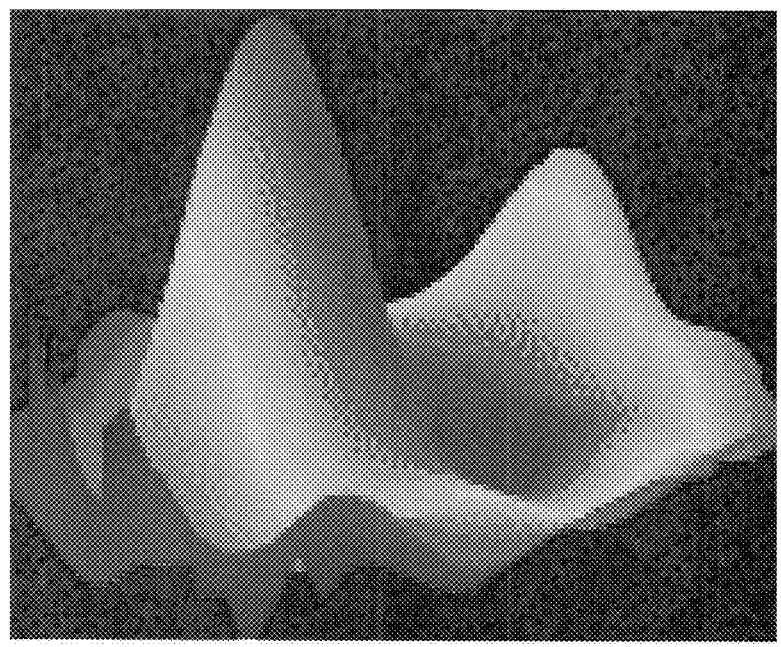
FIG. 6 illustrates an example of a 3D topographical map of an irregularly curved surface.

One skilled in the art will readily recognize that other techniques for optical measurements of the cartilage surface curvature can be employed without departing from the scope of the invention. For example, a 2-dimensional or 3-dimensional map, such as that shown in FIG. 5 and FIG. 6 can be generated.

Mechanical devices (e.g., probes) can also be used for intraoperative measurements, for example, deformable materials such as gels, molds, any hardening materials (e.g., materials that remain deformable until they are heated, cooled, or otherwise manipulated). See, e.g., WO 02/34310 to Dickson et al., published May 2, 2002. For example, a deformable gel can be applied to a femoral condyle. The side of the gel pointing towards the condyle can yield a negative impression of the surface contour of the condyle. The negative impression can then be used to determine the size of a defect, the depth of a defect and the curvature of the articular surface in and adjacent to a defect. This information can be used to select a therapy, e.g. an articular surface repair system. In another example, a hardening material can be applied to an articular surface, e.g. a femoral condyle or a tibial plateau. The hardening material can remain on the articular surface until hardening has occurred. The hardening material can then be removed from the articular surface. The side of the hardening material pointing towards the articular surface can yield a negative impression of the articular surface. The negative impression can then be used to determine the size of a defect, the depth of a defect and the curvature of the articular surface in and adjacent to the defect. This information can then be used to select a therapy, e.g. an articular surface repair system. In some embodiments, the hardening system can remain in place and form the actual articular surface repair system.

In certain embodiments, the deformable material comprises a plurality of individually moveable mechanical elements. When pressed against the surface of interest, each element can be pushed in the opposing direction and the extent to which it is pushed (deformed) can correspond to the curvature of the surface of interest. The device can include a brake mechanism so that the elements are maintained in the position that conforms to the surface of the cartilage and/or bone. The device can then be removed from the patient and analyzed for curvature. Alternatively, each individual moveable element can include markers indicating the amount and/or degree it is deformed at a given spot. A camera can be used to intra-operatively image the device and the image can be saved and analyzed for curvature information. Suitable markers include, but are not limited to, actual linear measurements (metric or imperial), different colors corresponding to different amounts of deformation and/or different shades or hues of the same color(s). Displacement of the moveable elements can also be measured using electronic means.

Other devices to measure cartilage and subchondral bone intraoperatively include, for example, ultrasound probes. An ultrasound probe, preferably handheld, can be applied to the cartilage and the curvature of the cartilage and/or the subchondral bone can be measured. Moreover, the size of a cartilage defect can be assessed and the thickness of the articular cartilage can be determined. Such ultrasound measurements can be obtained in A-mode, B-mode, or C-mode. If A-mode measurements are obtained, an operator can typically repeat the measurements with several different probe orientations, e.g. mediolateral and anteroposterior, in order to derive a three-dimensional assessment of size, curvature and thickness.

One skilled in the art will easily recognize that different probe designs are possible using the optical, laser interferometry, mechanical and ultrasound probes. The probes are preferably handheld. In certain embodiments, the probes or at least a portion of the probe, typically the portion that is in contact with the tissue, can be sterile. Sterility can be achieved with use of sterile covers, for example similar to those disclosed in WO 99/08598A1 to Lang, published Feb. 25, 1999.

Analysis on the curvature of the articular cartilage or subchondral bone using imaging tests and/or intraoperative measurements can be used to determine the size of an area of diseased cartilage or cartilage loss. For example, the curvature can change abruptly in areas of cartilage loss. Such abrupt or sudden changes in curvature can be used to detect the boundaries of diseased cartilage or cartilage defects.

II. Single Surface Assessment of a Joint

Figure 7A:
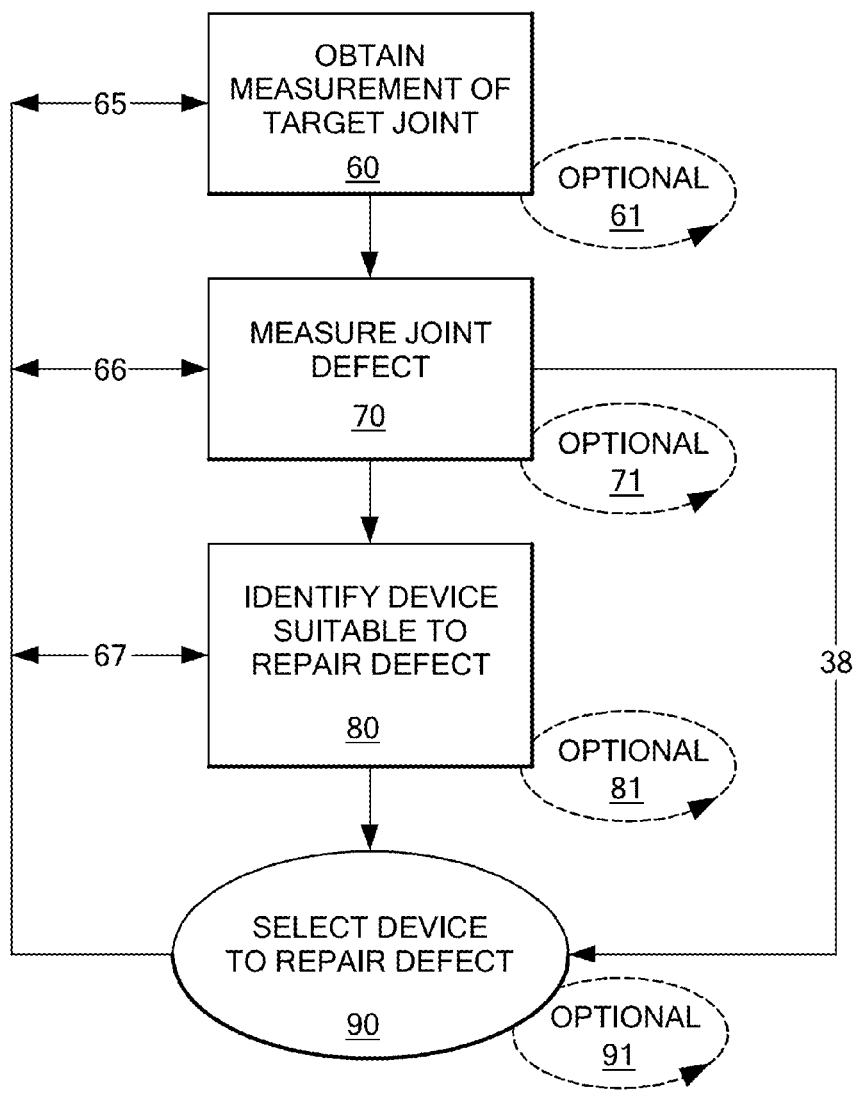
FIGS. 7A-B are block diagrams of a method for assessing a joint in need of repair according to the invention wherein the existing joint surface is altered prior to receiving implant.

Turning now to FIG. 7A, a block diagram is provided showing steps for performing a single surface assessment of the joint. As with FIGS. 1A and B an image or measurement is obtained of the target joint 60. Thereafter a measurement is taken to assist in selecting an appropriate device to correct the defect 70. The measuring or imaging steps can be repeated as desired to facilitate identifying the most appropriate device 80 to repair the defect. Once the measurement or measurements have been taken, a device is selected for correcting the defect 90. In this instance, only one surface of the joint is replicated. This technique is particularly useful for implants that include mechanisms for anchoring the implant into the bone. Thus, the implant has at least one surface that replicates a joint surface with at least a second surface that communicates with some or all of the articular surface or bone of the damaged joint to be repaired.

As will be appreciated by those of skill in the art, the practitioner can proceed directly from the step of measuring the joint defect 70 to the step of selecting a suitable device to repair the defect 90 as shown by the arrow 38. Further any, or all, of the steps of obtaining a measurement of a target joint 60, measuring a joint defect 70, identifying device suitable to repair the defect 80, selecting a device to repair the defect 90, can be repeated one or more times 61, 71, 81, 91, as desired.

Similar to the flow shown above, following the selection of a device to repair the defect 90, the steps of obtaining a measurement of a target joint 60, measuring a joint defect 70, identifying device suitable to repair the defect 80, can be repeated in series or parallel as shown by the flow 65, 66, 67.

Figure 7B:
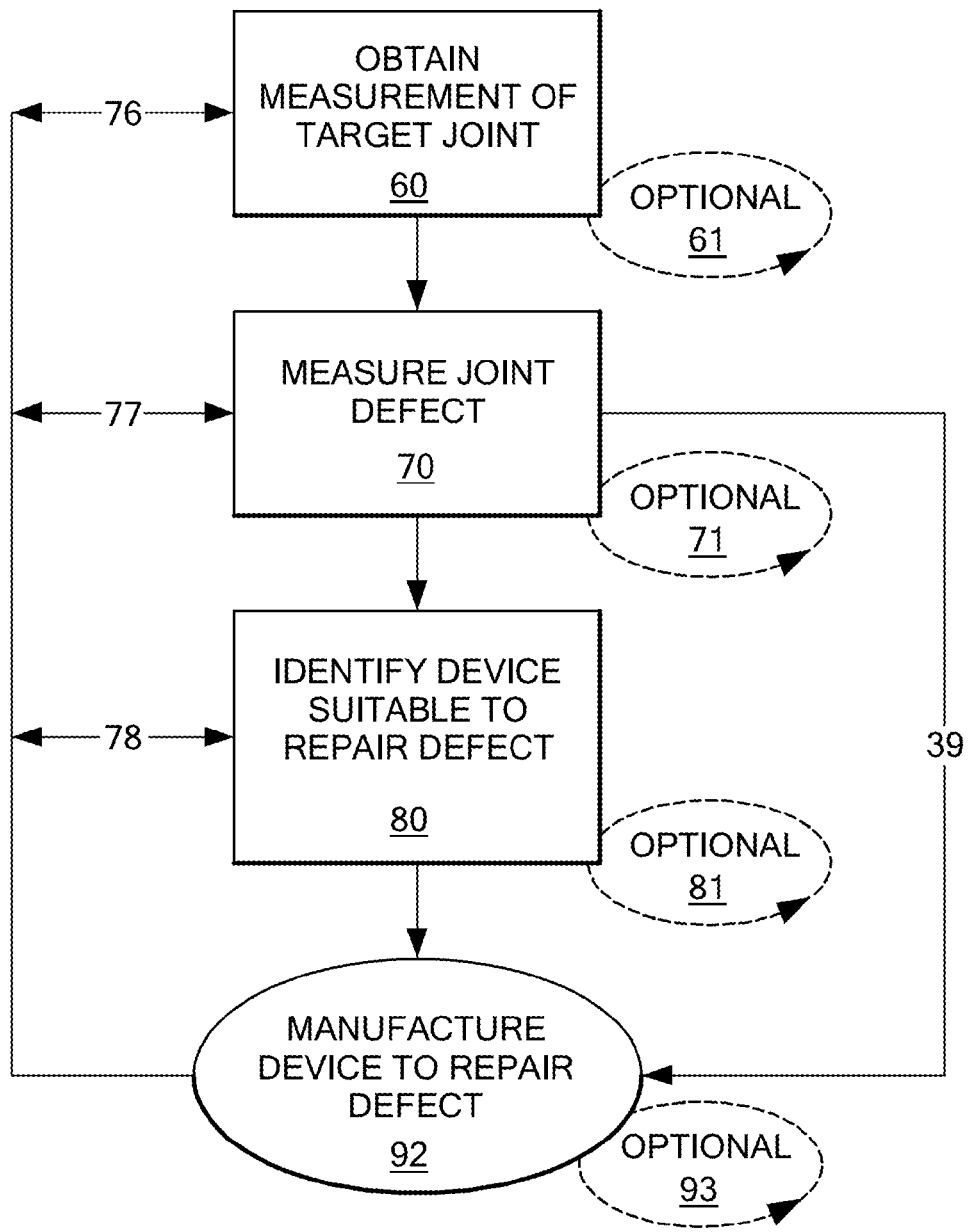

FIG. 7B shows an alternate method. A block diagram is provided showing steps for performing a single surface assessment of the joint. As with FIGS. 1A and B an image or measurement is obtained of the target joint 60. Thereafter a measurement is taken to assist in selecting an appropriate device to correct the defect 70. The measuring or imaging steps can be repeated 71 as desired to facilitate identifying the most appropriate device 80 to repair the defect. Once the measurement or measurements have been taken, a device is manufactured for correcting the defect 92.

As will be appreciated by those of skill in the art, the practitioner can proceed directly from the step of measuring the joint defect 70 to the step of manufacturing a device to repair the defect 92 as shown by the arrow 39. Further any, or all, of the steps of obtaining a measurement of a target joint 60, measuring a joint defect 70, identifying device suitable to repair the defect 80, manufacturing a device to repair the defect 92, can be repeated one or more times 61, 71, 81, 93, as desired.

Similar to the flow shown above, following the manufacture of a device to repair the defect 92, the steps of obtaining a measurement of a target joint 60, measuring a joint defect 70, identifying device suitable to repair the defect 80, can be repeated in series or parallel as shown by the flow 76, 77, 78.

Various methods are available to facilitate the modeling the joint during the single surface assessment. For example, using information on thickness and curvature of the cartilage, a model of the surfaces of the articular cartilage and/or of the underlying bone can be created for any joint. The model representation of the joint can be in one, two, or three dimensions. It can include a physical model. This physical model can be representative of a limited area within the joint or it can encompass the entire joint.

More specifically, in the knee joint, the physical model can encompass only the medial or lateral femoral condyle, both femoral condyles and the notch region, the medial tibial plateau, the lateral tibial plateau, the entire tibial plateau, the medial patella, the lateral patella, the entire patella or the entire joint. The location of a diseased area of cartilage can be determined, for example using a 3D coordinate system or a 3D Euclidian distance transform as described in WO 02/22014 to Alexander, et al. or a LaPlace transform.

In this way, the size of the defect to be repaired can be accurately determined. As will be apparent, some, but not all, defects can include less than the entire cartilage. The thickness of the normal or only mildly diseased cartilage surrounding one or more cartilage defects is measured. This thickness measurement can be obtained at a single point or a plurality of points. The more measurements that are taken, the more refined and accurate the measurement becomes. Thus, measurements can be taken at, for example, 2 points, 4-6 points, 7-10 points, more than 10 points or over the length of the entire remaining cartilage. Two-dimensional and three-dimensional measurements can be obtained. Furthermore, once the size of the defect is determined, an appropriate therapy (e.g., implant or an implant replacing an area equal to or slightly greater than the diseased cartilage covering one or more articular surfaces) can be selected such that as much as possible of the healthy, surrounding tissue is preserved.

Alternatively, the curvature of the articular surface or the underlying bone can be measured to design and/or shape the repair material. In this instance, both the thickness of the remaining cartilage and the curvature of the articular surface can be measured to design and/or shape the repair material. Alternatively, the curvature of the subchondral bone can be measured and the resultant measurement(s) can be used to design, produce, select and/or shape a cartilage replacement material.

III. Joint Devices

The present device is a prosthesis. The form of the prosthesis or device is determined by projecting the contour of the existing cartilage and/or bone to effectively mimic aspects of the natural articular structure. The device substantially restores the normal joint alignment and/or provides a congruent or substantially congruent surface to the original or natural articular surface of an opposing joint surface that it mates with. Further, it can essentially eliminate further degeneration because the conforming surfaces of the device provide an anatomic or near anatomic fit with the existing articular surfaces of the joint. Insertion of the device is done via a small (e.g., 3 cm to 5 cm) incision and no bone resection or mechanical fixation of the device is required. However, as will be appreciated by those of skill in the art, additional structures can be provided, such as a cross-bar, fins, pegs, teeth (e.g., pyramidal, triangular, spheroid, or conical protrusions), or pins, that enhance the devices' ability to seat more effectively on the joint surface. Osteophytes or other structures that interfere with the device placement are easily removed. By occupying the joint space in an anatomic or near anatomic fit, the device improves joint stability and restores normal or near normal mechanical alignment of the joint.

The precise dimensions of the devices described herein can be determined by obtaining and analyzing images of a particular subject and designing a device that substantially conforms to the subject's joint anatomy (cartilage and/or bone) while taking into account the existing articular surface anatomy as described above. Thus, the actual shape of the present device can be tailored to the individual.

A prosthetic device of the subject invention can be a device suitable for minimally invasive, surgical implantation without requiring bone resection. The device can, but need not be, affixed to the bone. For example, in the knee the device can be unicompartmental, i.e., positioned within a compartment in which a portion of the natural meniscus is ordinarily located. The natural meniscus can be maintained in position or can be wholly or partially removed, depending upon its condition. Under ordinary circumstances, pieces of the natural meniscus that have been torn away are removed, and damaged areas can be trimmed, as necessary. Alternatively, all of the remaining meniscus can be removed. This can be done via the incision used for insertion of the device. For many of the implants, this can also be done arthroscopically making an incision that is 1-15 cm in length, but more preferably 1-8 cm in length, and even more preferably 1-4 cm.

The implants described herein can have varying curvatures and radii within the same plane, e.g. anteroposterior or mediolateral or superoinferior or oblique planes, or within multiple planes. In this manner, the articular surface repair system can be shaped to achieve an anatomic or near anatomic alignment between the implant and the implant site. This design not only allows for different degrees of convexity or concavity, but also for concave portions within a predominantly convex shape or vice versa. The surface of the implant that mates with the joint being repaired can have a variable geography that can be a function of the physical damage to the joint surface being repaired. Although, persons of skill in the art will recognize that implants can be crafted based on typical damage patterns. Implants can also be crafted based on the expected normal congruity of the articular structures before the damage has occurred.

Moreover, implants can be crafted accounting for changes in shape of the opposing surfaces during joint motion. Thus, the implant can account for changes in shape of one or more articular surface during flexion, extension, abduction, adduction, rotation, translation, gliding and combinations thereof.

The devices described herein are preferably marginally translatable and self-centering. Thus, during natural articulation of a joint, the device is allowed to move slightly, or change its position as appropriate to accommodate the natural movement of the joint. The device does not, however, float freely in the joint. Further, upon translation from a first position to a second position during movement of a joint, the device tends to returns to substantially its original position as the movement of the joint is reversed and the prior position is reached. As a result, the device tends not to progressively "creep" toward one side of the compartment in which it is located. The variable geography of the surface along with the somewhat asymmetrical shape of the implant facilitates the self-centering behavior of the implant.

The device can also remain stationary over one of the articular surface. For example, in a knee joint, the device can remain centered over the tibia while the femoral condyle is moving freely on the device. The somewhat asymmetrical shape of the implant closely matched to the underlying articular surface helps to achieve this kind of stabilization over one articular surface.

The motion within the joint of the devices described herein can optionally, if desired, be limited by attachment mechanisms. These mechanisms can, for example, allow the device to rotate, but not to translate. It can also allow the device to translate in one direction, while preventing the device from translating into another direction. The mechanisms can furthermore fix the devices within the joint while allowing the device to tilt. Suitable attachment mechanisms include ridges, pegs, pins, cross-members, teeth and protrusions. The configuration of these mechanisms can be parallel to one another, or non-parallel in orientation. The mechanisms can be pyramidal, triangular, spheroid, conical, or any shape that achieves the result. One or more attachment mechanism can be provided. Where more than one mechanism is provided, the mechanisms can cover the entire surface of the device, or a portion of the surface. Additional stabilization mechanisms can be provided such as ridges, lips and thickenings along all or a portion of a peripheral surface.

The implant shape can also incorporate the shape of the joint on which it is position, such as portions of the tibial spines. Adding conformity with the tibial spines, e.g. the base of the tibial spines, can help in stabilizing the implant relative to the tibial plateau.

The implant height or profile selected can be chosen to alter the load bearing ability relative to the joint. Additionally the implant height can be adjusted to account for anatomic malalignment of bones or articular structures. Additionally, for any of the implants taught herein in the presence of ligamentous laxity, the implant height, profile or other dimension can be adjusted to allow tightening of the ligament apparatus to improve the function. This occurs preferably without substantially interfering with axis alignment of the bones. Typically, the joints of are able to withstand up to 100% of the shear force exerted on the joint in motion.

The implants of the invention typically restore joint mobility up to 99.9% of natural mobility of the joint for a particular subject. For example, in the case of the knee overall articulation typically ranges from 0 to 140°. Currently available solutions typically restore articulation in a range substantially less than 99.9%, while implants of the present invention typically restore the range of motion to between 95-99.9% of normal range of motion for the patient.

Ranges of motion for joints of the hands and arms for a healthy male obtained from National Institute of Standards and Technology (http://ovrt.nist.gov) are described in TABLE 1.

TABLE 1

RANGE OF MOVEMENT OF HAND AND ARM JOINTS

| Joint Movement | Range (degree) Average | Range (degree) S.D. |
|---|---|---|
| Wrist Flexion | 90 | 12 |
| Wrist Extension | 99 | 13 |
| Wrist Adduction | 27 | 9 |
| Wrist Abduction | 47 | 7 |
| Forearm Supination | 113 | 22 |
| Forearm Pronation | 77 | 24 |

TABLE 1-continued

RANGE OF MOVEMENT OF HAND AND ARM JOINTS

| Joint Movement | Range (degree) Average | Range (degree) S.D. |
|---|---|---|
| Elbow Flexion | 142 | 10 |
| Shoulder Flexion | 188 | 12 |
| Shoulder Extension | 61 | 14 |
| Shoulder Adduction | 48 | 9 |
| Shoulder Abduction | 134 | 17 |

Ranges of motion for joints of the foot and leg for a healthy male obtained from National Institute of Standards and Technology (http://ovrt.nist.gov) are described in TABLE 2.

TABLE 2

RANGE OF MOVEMENT OF FOOT AND LEG JOINTS

| Joint Movement | Range (degree) Average | Range (degree) S.D. |
|---|---|---|
| Ankle Flexion | 35 | 7 |
| Ankle Extension | 38 | 12 |
| Ankle Adduction | 24 | 9 |
| Ankle Abduction | 23 | 7 |
| Knee Flexion - Standing | 113 | 13 |
| Knee Flexion - Kneeling | 159 | 9 |
| Knee Flexion - Prone | 125 | 10 |
| Knee Rotation - Medial | 35 | 12 |
| Knee Rotation - Lateral | 43 | 12 |
| Hip Flexion | 113 | 13 |
| Hip Adduction | 31 | 12 |
| Hip Abduction | 53 | 12 |
| Hip Rotation - Sitting (medial) | 31 | 9 |
| Hip Rotation - Sitting (lateral) | 30 | 9 |
| Hip Rotation - Prone (medial) | 39 | 10 |
| Hip Rotation - Prone (lateral) | 34 | 10 |

Implants of the present invention should typically restore the range of motion for one or more of the measurements in Tables 1 and 2 for any joint to between 60-99.9% of normal range of motion for the patient and more preferably between 95-99.9% of normal range of motion for the patient.

As discussed in more detail below, any of the devices taught herein can be manufactured in a variety of ways such that the device is, for example, expands after insertion. Expansion can either be automatic, semi-automatic or upon adjustment by the user.

Turning now to illustrative examples of joint implants according to the scope and teachings of the invention.

A. The Knee

FIG. 8A shows a perspective view of a joint implant 100 of the invention suitable for implantation at the tibial plateau of the knee joint. As shown in FIG. 8A, the implant is generated using a dual surface assessment, as described above with respect to FIGS. 1A and B.

The implant 100 has an upper surface 102 and a lower surface 104 and a peripheral edge 106. The upper surface 102 is formed so that it forms a mating surface for receiving the opposing joint surface; in this instance partially concave to receive the femur. The concave surface can be variably concave such that it presents a surface to the opposing joint surface that approximates the mating surface of the joint it corrects. The lower surface 104 has a convex surface matches, or nearly matches, the tibial plateau of the joint such that it creates an anatomic or near anatomic fit with the tibial plateau. Depending on the shape of the tibial plateau, the lower surface can be partially convex. Thus, the lower surface 104 presents a surface to the tibial plateau that fits within the existing surface. As will be appreciated by those of skill in the art, the convex surface of the lower surface 104 need not be perfectly convex. Rather, the lower surface 104 is more likely consist of convex and concave elements to fit within the existing surface of the tibial plateau. Thus the surface is essentially variably convex and concave.

FIG. 8B shows a top view of the joint implant of FIG. 8A. As shown in FIG. 8B the exterior shape 108 of the implant can be elongated. The elongated form can take a variety of shapes including elliptical, quasi-elliptical, race-track, etc. However, as will be appreciated the exterior dimension is typically irregular thus not forming a true geometric ellipse. As will be appreciated by those of skill in the art, the actual exterior shape of an implant can vary depending on the nature of the joint defect to be corrected. Thus the ratio of the length L to the width W can vary from, for example, between 0.5 to 1.5, and more specifically from 0.25 to 2.0. As further shown in FIG. 8B, the length across an axis of the implant 100 varies when taken at points along the width of the implant. For example, as shown in FIG. 8B, $L_1 \neq L_2 \neq L_3$.

Turning now to FIGS. 8C-E, a cross-section of the implant shown in FIG. 8B is depicted along the lines of C-C, D-D, and E-E is shown. The implant has a thickness t1, t2 and t3 respectively. As illustrated by the cross-sections, the thickness of the implant varies along its length L. The actual thickness at a particular location of the implant 100 is a function of the thickness of the cartilage and/or bone to be replaced and the joint mating surface to be replicated. Further, the profile of the implant 100 at any location along its length or width is a function of the cartilage and/or bone to be replaced.

FIG. 8F is a lateral view of the implant 100 of FIG. 8A. In this instance the height of the implant 100 at a first end $h_1$ is different than the height of the implant at a second end $h_2$. Further the upper edge 108 can have an overall slope in a downward direction. However, as illustrated the actual slope of the upper edge 108 varies along its length and can, in some instances, be a positive slope. Further the lower edge 110 can have an overall slope in a downward direction. However, as illustrated the actual slope of the lower edge 110 varies along its length and can, in some instances, be a positive slope.

FIG. 8G is a cross-section taken along a sagittal plane in a body showing the implant 100 implanted within a knee joint 120 such that the implant 100 lies on the tibial plateau 122 and the femur 124 rests on the upper surface 102 of the implant 100. FIG. 8H is a cross-section taken along a coronal plane in a body showing the implant 100 implanted within a knee joint 120. As is apparent from this view, the implant 100 is positioned so that it fits within a superior articular surface 124. As will be appreciated by those of skill in the art, the articular surface could be the medial or lateral facet, as needed.

FIG. 8I is a cross-section along an axial plane of the body showing the implant 100 implanted within a knee joint 120 showing the view taken from an aerial, or upper, view. FIG. 8J is a cross-section of an alternate embodiment where the implant is a bit larger such that it extends closer to the bone medially, i.e. towards the edge of the tibial plateau, as well as extending anteriorly and posteriorly.

FIG. 8K is a cross-section of an implant 100 of the invention according to an alternate embodiment. In this embodiment, the lower surface 104 further includes a joint anchor 112. As illustrated in this embodiment, the joint anchor 112 forms a protrusion, keel or vertical member that extends from the lower surface 104 of the implant 100 and projects into, for example, the bone of the joint. Additionally, as shown in FIG. 8L the joint anchor 112 can have a cross-member 114 so that from a bottom perspective, the joint anchor 112 has the appearance of a cross or an "x." As will be appreciated by those of skill in the art, the joint anchor 112 could take on a variety of other forms while still accomplishing the same objective of providing increased stability of the implant 100 in the joint. These forms include, but are not limited to, pins, bulbs, teeth, balls, etc. Additionally, one or more joint anchors 112 can be provided as desired.

Figure 8M:
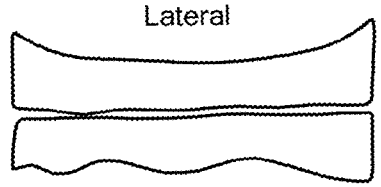
Figure 8M:
Figure 8N:
Figure 8N:

The device can have two or more components, one essentially mating with the tibial surface and the other substantially articulating with the femoral component. The two components can have a flat opposing surface. Alternatively, the opposing surface can be curved. The curvature can be a reflection of the tibial shape, the femoral shape including during joint motion, and the meniscal shape and combinations thereof. FIGS. 8M and N illustrate cross-sections of alternate embodiments of a dual component implant from a side view and a front view.

Turning now to FIGS. 9A-F an implant suitable for providing an opposing joint surface to the implant of FIG. 8A is shown. This implant corrects a defect on an inferior surface of the femur (i.e., the portion of the femur that mates with, e.g., the tibial plateau) and can be used alone, i.e., on the femur, or in combination with another joint repair device. FIG. 9A shows a perspective view of the implant 150 having a curved mating surface 152 and convex joint abutting surface 154. The joint abutting surface 154 need not form an anatomic or near anatomic fit with the femur in view of the anchors 156 provided to facilitate connection of the implant to the bone. In this instance, the anchors 156 are shown as pegs having notched heads. The notches facilitate the anchoring process within the bone. However, pegs without notches can be used as well as pegs with other configurations that facilitate the anchoring process. Pegs and other portions of the implant can be porous coated. The implant can be inserted without bone cement or with use of bone cement. The implant can be designed to abut the subchondral bone, i.e. it can substantially follow the contour of the subchondral bone. This has the advantage that no bone needs to be removed other than for the placement of the peg holes thereby significantly preserving bone stock. As will be appreciated by those of skill in the art, the multi-component solution illustrated in FIG. 9 for repairing the hip can be applied to other joints within the body as well.

Figure 9C:
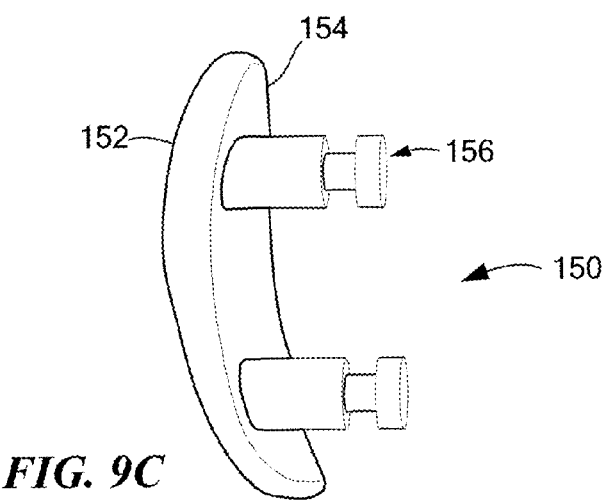
Figure 9D:
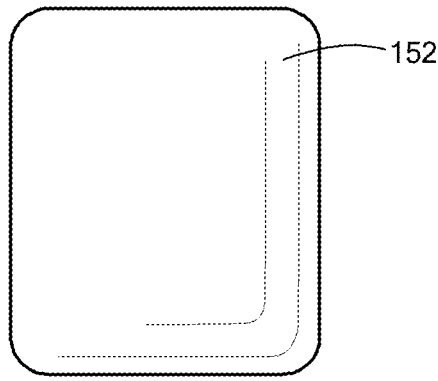
Figure 9E:
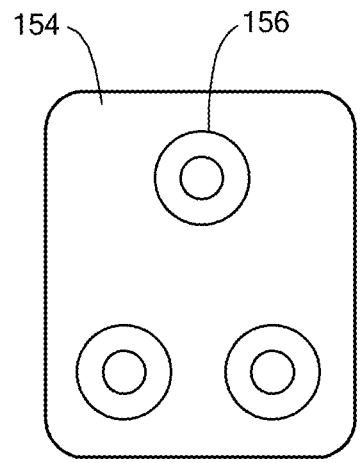
Figure 9F:
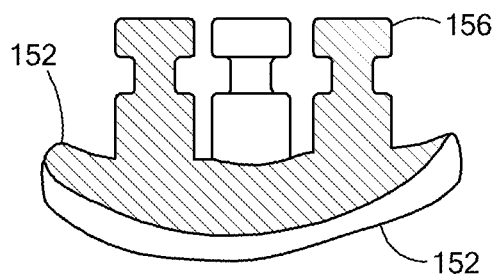
Figure 9G:
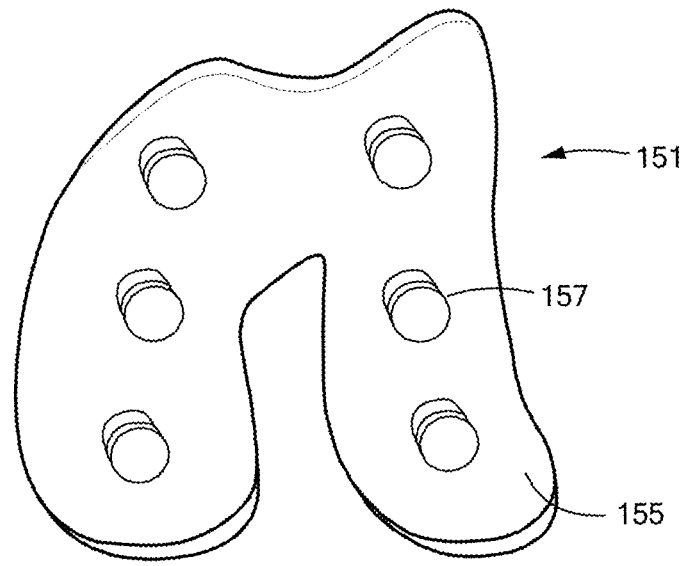
Figure 9H:
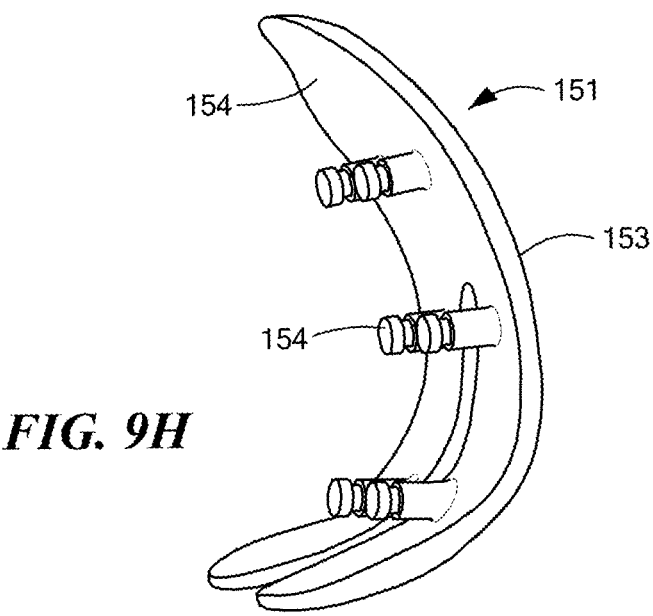

FIGS. 9G and 9H illustrate an implant 151 suitable for providing an opposing surface to the implant of FIG. 8A, wherein the implant is intended to cover both femoral condyles and can optionally oppose one or more of the implants of FIG. 8A.

The arthroplasty system can be designed to reflect aspects of the tibial shape and/or femoral shape. Tibial shape and femoral shape can include cartilage and bone or either. Moreover, the shape of the implant can also include portions or all components of other articular structures such as the menisci. The menisci are compressible, in particular during gait or loading. For this reason, the implant can be designed to incorporate aspects of the meniscal shape accounting for compression of the menisci during loading or physical activities. For example, the undersurface of the implant can be designed to match the shape of the tibial plateau including cartilage or bone or both. The superior surface of the implant can be a composite of the articular surface of the tibia (in particular in areas that are not covered by menisci) and the meniscus. Thus, the outer aspects of the device can be a reflection of meniscal height. Accounting for compression, this can be, for example, 20%, 40%, 60% or 80% of uncompressed meniscal height.

In some embodiments, the outer aspect of the device reflecting the meniscal shape can be made of another, preferably compressible material. If a compressible material is selected it is preferably designed to substantially match the compressibility and biomechanical behavior of the meniscus. The entire device can be made of such a material or non-metallic materials in general.

The height and shape of the menisci can be measured directly on an imaging test. If portions, or all, of the meniscus are torn, the meniscal height and shape can be derived from measurements of a contralateral joint or using measurements of other articular structures that can provide an estimate on meniscal dimensions.

In another embodiment, the superior face of the implant can be shaped according to the femur. The shape can preferably derived from the movement patterns of the femur relative to the tibial plateau thereby accounting for variations in femoral shape and tibiofemoral contact area as the femoral condyle flexes, extends, rotates, translates and glides on the tibia and menisci.

The movement patterns can be measured using any current or future test know in the art such as fluoroscopy, MRI, gait analysis and combinations thereof.

B. The Hip

Figure 10A:
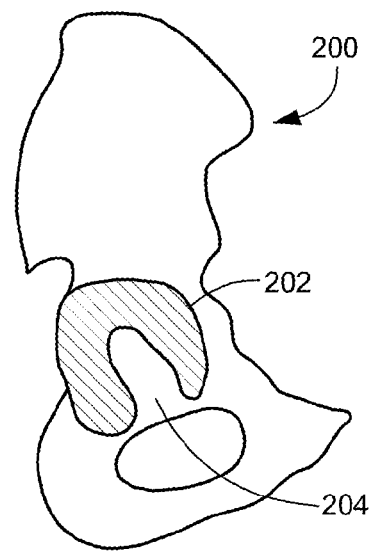
FIG. 10A is a side view of the acetabulum.
Figure 10B:
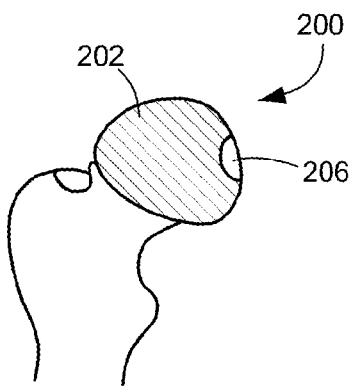
FIG. 10B is a rotated view of the proximal femur.

FIG. 10A is a side view of the acetabulum 200 of the hip. The cartilage covered area 202 has an inverted U-shape. The triradiate cartilage area or acetabular fossa 204 is located within the cartilage covered area. FIG. 10B is a rotated view of the proximal femur 210. The cartilage covered area 202 and the fovea capitis 206 are also shown.

Figure 10C:
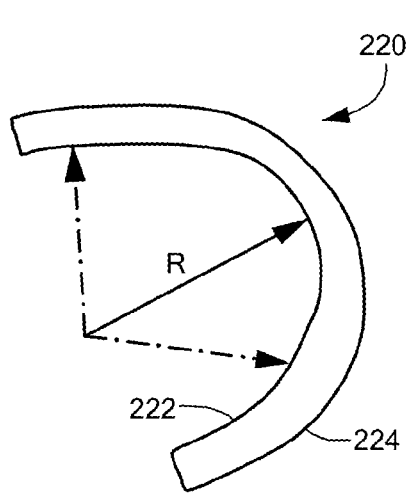
FIG. 10C is a cross-sectional view of an implant for a hip joint showing a substantially constant radius.

Turning now to implants suitable for the hip joint, FIG. 10C is a cross-section of an implant for a hip joint 220. The radius r of this implant is substantially constant when taken at any point along its length. The radius of the implant can be selected to approximate the radius of the femoral head that the implant is intended to correct and can be measured to an interior surface of the implant 220 that engages the femoral head. Alternatively, the radius of the implant can be selected to approximate the radius of the acetabulum or a combination thereof. The radius of the interior surface 222 of the implant faces the femur and can also match the radius of the femur or be similar to the radius of the acetabulum; the radius of the implant surface facing the acetabulum can also match that of the acetabulum 224 or be similar to that of the femur.

A person of skill in the art will appreciate that the natural geometry of the acetabulum typically is aspherical, varying slightly from a true spherical shape. The radius of the implant adjusts, as necessary, to the changing radius of the acetabulum to provide a better fit. Thus, implants can be spherical or aspherical in radius on either or both of the superior and/or inferior surface.

Figure 10D:
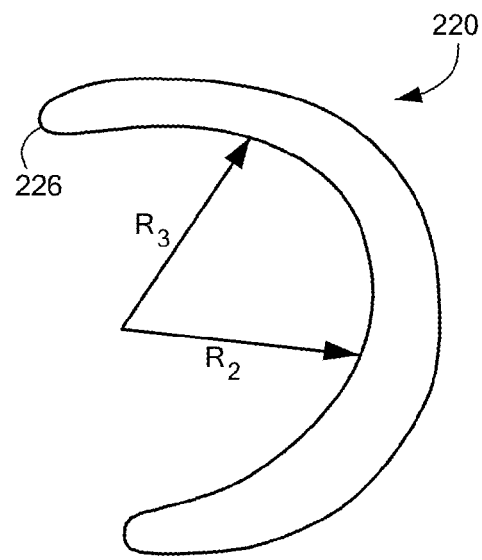
FIG. 10D is a cross-sectional view of an implant similar to that seen in FIG. 10C with a round margin and an asymmetric radius.

FIG. 10D is a cross-section of an implant suitable for the hip similar to that seen in FIG. 10C, featuring a rounded margin 226. A round margin 226 can be advantageous because it tends to avoid locking of the implant when in use as well as minimizing any pain that might be associated with the implant.

Figure 11A:
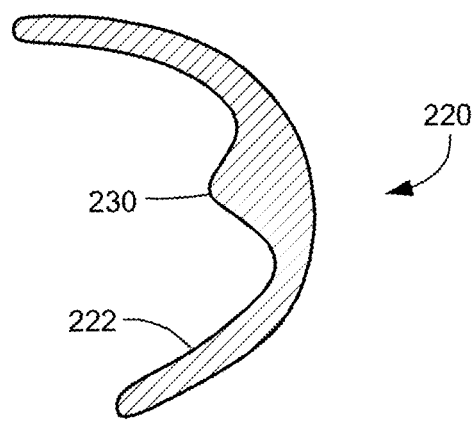
FIG. 11A is a cross-sectional view of an implant with a member extending into the fovea capitis of the femoral head. Additional and alternative plan views are shown of FIG. 11B showing the implant as a hemisphere, a partial hemisphere FIG. 11C and a rail FIG. 11D.
Figure 11B:
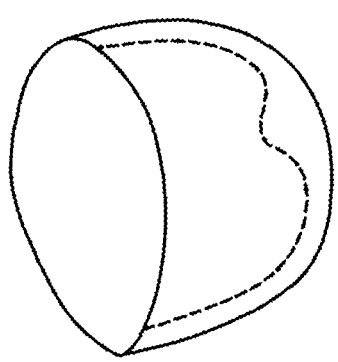
FIG. 11E is a view of an alternative embodiment of an implant with a spoke arrangement.
Figure 11C:
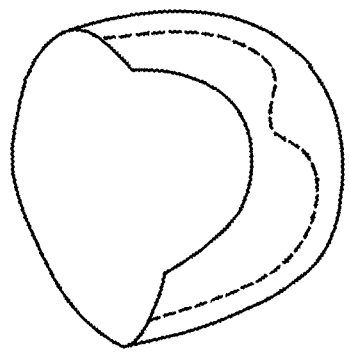
Figure 11D:
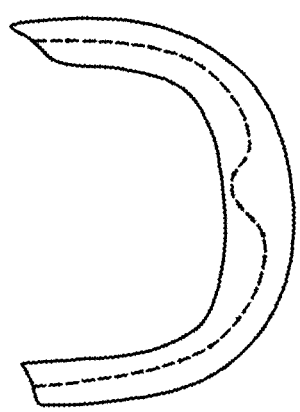
Figure 11E:
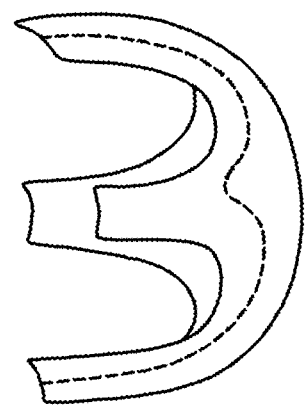

FIG. 11A is a cross-section of an implant 220 suitable for the hip similar to that shown in FIG. 10C with a nub 230 is provided that extends into the fovea capitis of the femoral head 240 on its interior surface 222. The member 230 can be made of the same material as the implant 220, or a material different from the remainder of the implant. The advantage of an implant having a nub 230 for engaging the fovea capitis is that the nub 230 can function to constrain movement of the implant 220 relative to the femoral head (shown in FIG. 10B). As will be appreciated by those of skill in the art, the nub 230 can take a variety of configurations while still accomplishing the same effect when engaging the fovea capitis upon implantation. A variety of plan views are shown that provide for an implant that is hemispherical, partially hemispherical, or in the form of a rail. Additional shapes will be apparent to those of skill in the art. Additionally, the edges of the implant can be rounded, beveled or whatever dimension that facilitates the operation of the implant. FIGS. 11B-E illustrate alternative embodiments of the implant shown in FIG. 11A, wherein the implant is hemispherical, partially hemispherical, rail and spoke.

FIG. 12A is a cross-section of an implant 220 suitable for the hip with a ledge 232 that extends into the acetabular fossa 204 on its exterior surface 224. The ledge 232 can be made of the same or a different material as the remainder of the implant 220. The ledge 232 can be used to constrain movement of the implant relative to the acetabular fossa. As will be appreciated by those of skill in the art, the ledge 232 can take a variety of configurations while still accomplishing the same effect when engaging the acetabular fossa. A variety of plan views are shown that provide for an implant that is hemispherical, partially hemispherical, or in the form of a rail or four-prong cap. Additional shapes will be apparent to those of skill in the art. Additionally, the edges of the implant can be rounded, beveled or whatever dimension that facilitates the operation of the implant. FIGS. 12B-E illustrate alternative embodiments of the implant shown in FIG. 12A, wherein the implant is hemispherical, partially hemispherical, rail and spoke.

Figure 13G:
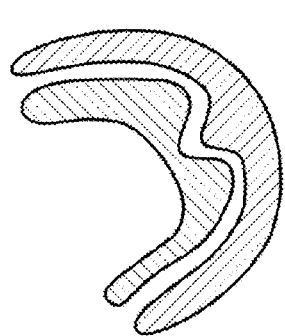
Figure 13H:
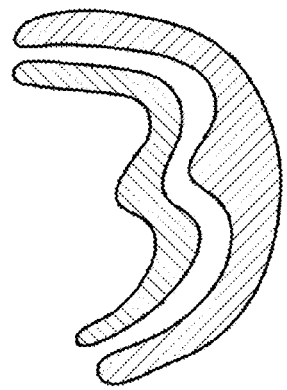
Figure 13I:
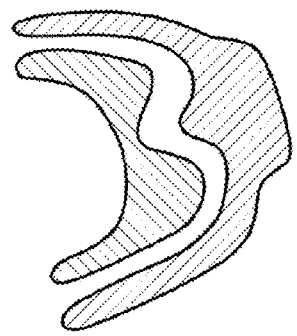
Figure 13J:
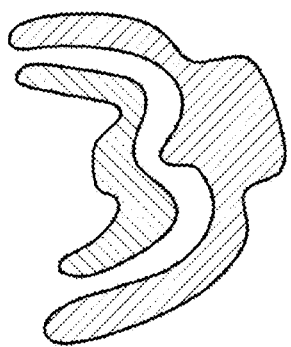

FIG. 13A is a cross-section of a dual component "mobile bearing" implant 221 with a variety of plan views. The implant has a first component 230 and a second component 231. The first component fits within the second component and has two smooth surfaces. The second component engages the outer surface of the first component and also has two smooth surfaces. A variety of configurations in plan is possible without departing from the scope of the invention. For example, each component can be hemispherical. One component can be hemispherical while the other one takes on a shape that is a part-hemisphere, a shorter hemisphere, a rail, or a four-prong dome. FIGS. 13B-F illustrate a variety of alternative embodiments of the implant shown in FIG. 13A, wherein the implant has at least one component that is hemispherical, partially hemispherical, rail and spoke.

FIGS. 13G-J are cross-sectional views of a dual component "mobile bearing" implant. The implant has a first component and a second component. The first component fits within the second component. The second component engages the outer surface of the first component. As shown herein a nub is provided on the second component that fits within an indentation on the first component. As will be appreciated by those of skill in the art, although not shown, the nub could be on the first component and fit within a well on the second component without departing from the scope of the invention. Additional anchoring mechanisms either on the first component, second component, or both are also possible, as shown. A variety of configurations in plan is possible, although not shown, without departing from the scope of the invention. For example, each component can be hemispherical. One component can be hemispherical while the other one takes on a shape that is a part-hemisphere, a shorter hemisphere, a rail, or a four-prong dome.

Figure 14A:
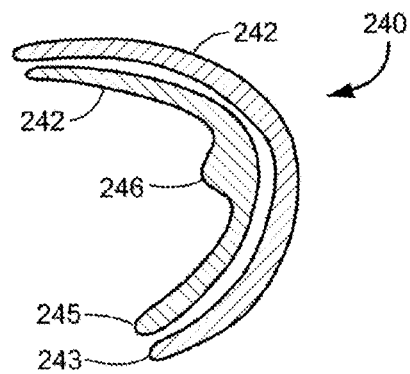
FIG. 14A is an alternative embodiment of an implant with a member extending into the fovea capitis of the femoral head.
Figure 14B:
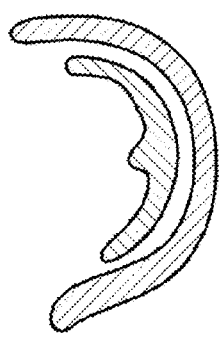
FIG. 14B and FIG. 14C show cross-sectional embodiments, where one of the components forms a hemisphere while the second component does not.
Figure 14C:
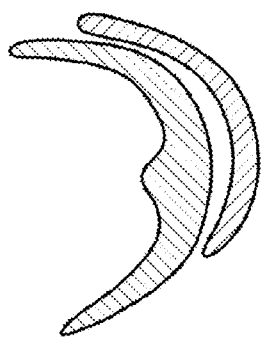
Figure 15A:
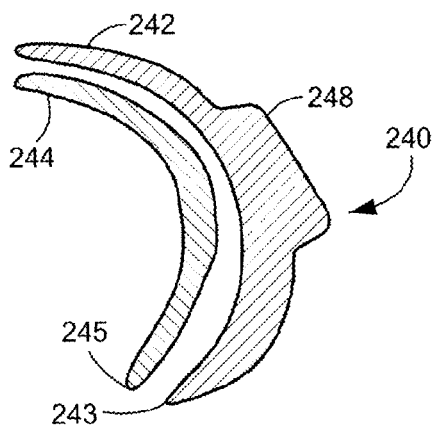
FIG. 15A is a cross-sectional view of a dual component "mobile bearing" implant with a member extending into the acetabular fossa.
Figure 15B:
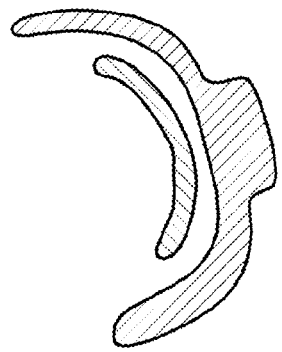
FIG. 15B and FIG. 15C show cross-sectional embodiments, where one of the components forms a hemisphere while the second component does not.
Figure 15C:
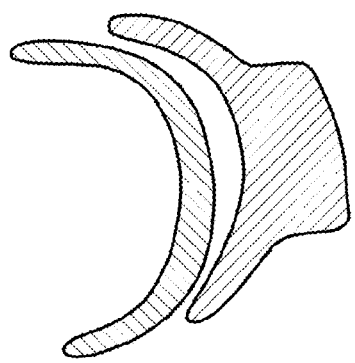

FIG. 14A is a cross-section of another dual component "mobile bearing" implant 240 with a nub 246 for extending into the fovea capitis 206 of the femoral head. The dual component implant 240 has a first component 242 and a second component 244. A nub 246 is provided on the second component 244. As described above with respect to FIG. 11C, the nub 246 can be used to constrain movement of the second component 244 of the implant 240 relative to the femoral head. The first component 242 facing the acetabulum can move freely relative to the second component 244 facing the femoral head. As will be appreciated by those of skill in the art, the dual component implant can be configured such that the surface of the first component 243 that engages the surface of the second component 245 have the same length, or substantially the same length. Thus creating mating components that fit substantially within one another. Alternatively, the components can be configured such that one component is shorter than another component as shown in FIG. 14B and FIG. 14C. FIG. 15A is a cross-section of another dual component "mobile bearing" implant 240 with a ledge 248 extending into the acetabular fossa. The dual component implant 240 has a first component 242 and a second component 244. A ledge 248 is provided on the first component 242. The ledge 248 can be used to constrain movement of the first component 242 of the implant 240 relative to the acetabulum. The second component 244 facing the femoral head can move freely relative to the first component 242 facing the acetabulum. As described above with respect to FIG. 13A, the implant shown in FIG. 15A can also be configured such that one component is shorter than another component as shown in FIGS. 15B and 15C.

Figure 16A:
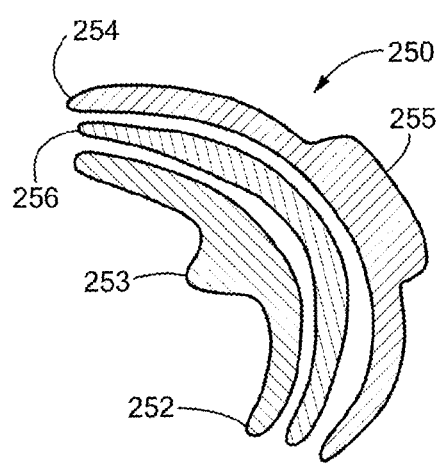
FIG. 16A is a cross-sectional view of a triple component "mobile bearing" implant.
Figure 16B:
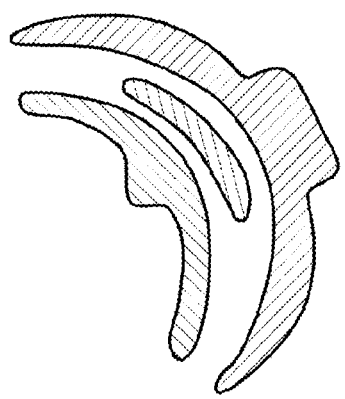

FIG. 16A is a cross-section of a triple component "mobile bearing" implant 250. The first component 252 facing the acetabulum has a nub 253 extending into the acetabular fossa 204. As discussed above, the nub 253 can be used to constrain movement of the implant 250 relative to the acetabulum. The second component 254 facing the femoral head has a ledge 255 extending into the fovea capitis 206. As discussed above with respect to the single and dual member implants, the ledge 255 can be used to constrain movement of the second component 254 of the implant 250 relative to the femoral head. The third component 256 is interposed between the two other components and can move freely between them. As will be appreciated by those of skill in the art, the third component 256 can be interposed between the first 252 and second 254 components such that its length is shorter than either the first 252 or second 254 components (as shown in FIG. 16B) or longer than either of the first 252 or second 254 components (as shown in FIGS. 16C and 16D). Similarly, it would be possible for the length of the third component to be longer than either of the first 252 or second 254 components.

FIG. 17A is a cross-section of another dual component "mobile bearing" implant 240 similar to those shown above. In this embodiment, anchors are provided to anchor the first component 242 to the acetabular fossa 204. The anchors shown are in the form of one or more pins 262. The component facing the acetabulum is fixed to the acetabulum using two substantially parallel pegs. The second component 244 facing the femoral head can move freely on the first component 242 facing the acetabulum. As with the previous embodiments, the length of the first component 242 relative to the second component 244 can vary. FIGS. 17B and 17C show alternate cross-sectional views where a first component is larger that a second component, and vice versa. As with the previous embodiments, a variety of configurations in plan is possible without departing from the scope of the invention. For example, each component can be hemispherical. One component can be hemispherical while the other one takes on a shape that is a part-hemisphere, a shorter hemisphere, a rail, or a four-prong dome.

FIG. 18A is a cross-section of another dual component "mobile bearing" implant 240 with an anchor extending into the acetabular fossa 204. The anchor facing the acetabulum is in the form of a protrusion having one or more fins 264. The second component 244 facing the femoral head can move freely on the first component 242 facing the acetabulum. FIG. 18B is a view of the implant of FIG. 18A from the top showing four fins (264, 264', 264'', 264''') on top of the member extending into the acetabular fossa on top of the acetabular component. The fins can be sharp or substantially sharp as shown or can have rounded edges.

FIG. 19A is a cross-section of another dual component "mobile bearing" implant 240 with an anchor 266 capable of extending into the fovea capitis 206 of the femoral head. In the embodiment shown, the second component 244 facing the femoral head is fixed to the femoral head using one or more substantially parallel pegs (shown as 268, 268'b. The first component 242 faces the acetabulum, as shown in previous embodiments, and can move freely on the component facing the femoral head.

FIG. 19B is a cross-section of another dual component implant 240. In this embodiment, the dual component 240 is fixed. As illustrated herein, the femoral component is attached to the femoral head using 3 pegs 266 or other attachment mechanisms. The number of pegs can be greater or less than 3, as desired. Preferably, the subchondral bone remains intact with this design except for the entry point of the pegs. The acetabular component is attached to the acetabulum using fins 264 or similar attachment means such as pegs (shown in FIG. 17A). The attachment mechanism can be molded to the acetabularfossa with members extending into the bone. The subchondral bone preferably also remains intact except for the entry area for the attachment means.

Figure 20A:
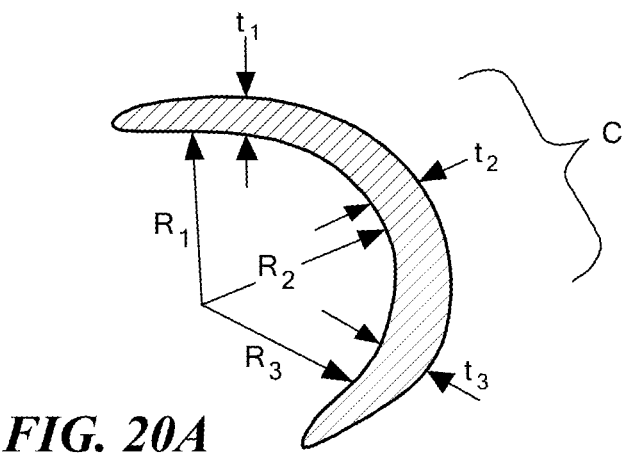
FIG. 20A is a cross-sectional view of an implant with varying radii and thickness for a hip joint.

FIG. 20A is a cross-section of an implant 470 with varying radii ($r_1$, $r_2$, $r_3$) and thickness ($t_1$, $t_2$, $t_3$) for a hip joint; where $r_1 \neq r_2 \neq r_3$ and thickness $t_1 \neq t_2 \neq t_3$. As will be appreciated by those of skill in the art, three measurements of radii and thickness have been taken to illustrate the point, but more or less measurements can be used without departing from the scope of the invention. Additionally, other combinations of radii and thicknesses can be employed such that, for example, $r_1 = r_2 \neq r_3$, $r_1 \neq r_2 = r_3$, $t_1 = t_2 \neq t_3$ and $t_1 \neq t_2 = t_3$. Other combinations will be apparent to those of skill in the art. As illustrated in FIG. 20A, the central portion c that has a thickness t that is thicker relative to one or both peripheral portions $p_1$, $p_2$.

Figure 20B:
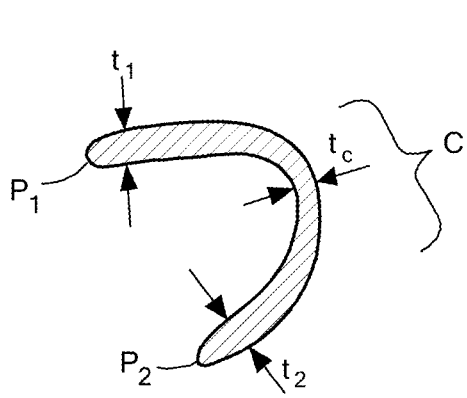
FIG. 20B is a cross-sectional view of an implant with varying radii and thickness for a hip joint.

FIG. 20B is a cross-section of an alternate implant 470 with varying radii and thickness for a hip joint. In this embodiment, the central portion c has a thickness $t_c$ that is thinner relative to one or more thicknesses $t_1$, $t_2$ of the peripheral portions ($p_1$, $p_2$).

Figure 20C:
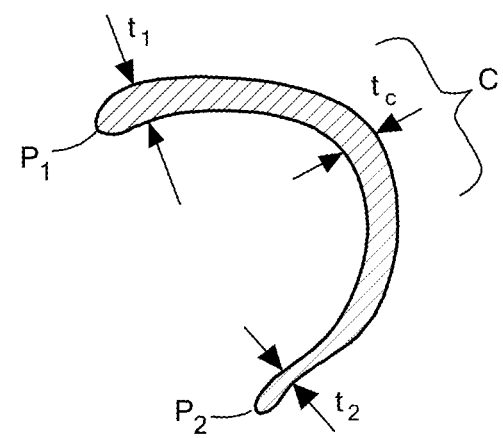
FIG. 20C is a cross-sectional view of an implant with varying radii and thickness for a hip joint.

FIG. 20C is a cross-section of an alternate implant 470 with varying radii and thickness for a hip joint. In this embodiment, the central portion c has a thickness $t_c$ that is thinner relative to the thickness $t_1$ of a first peripheral end $p_1$, and thicker relative to the thickness $t_2$ of a second peripheral end $p_2$ of the peripheral portions.

Figure 20D:
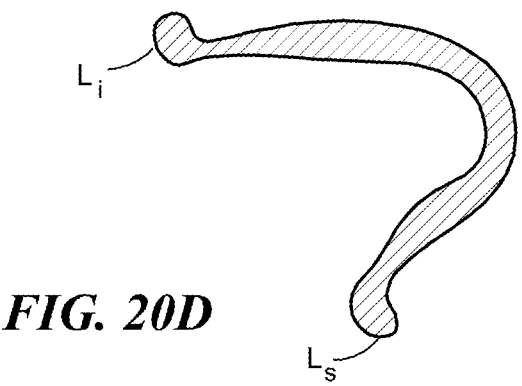
FIG. 20D is a cross-sectional view of an implant for a hip joint with a lip extending inferiorly and superiorly.

FIG. 20D is a cross-section of an alternate implant 470 for a hip joint with one or more lips or anchoring extensions extend inferiorly $I_i$ and/or superiorly $I_s$. The lips are designed to extend beyond the articular surface, e.g. into non-cartilaginous areas. It can substantially conform to the surrounding, periarticular anatomy. The lips can provide additional stabilization. This design can be combined with dual and triple component and "mobile-bearing" designs.

As will be appreciated by those of skill in the art, the three-dimensional shape of the implants shown in FIGS. 10-20 can be semicircular (i.e., 180°) in one or more dimension, but need not be. Where the implant is semicircular in all dimensions, the implant forms a hemisphere (i.e., half of a sphere obtained by cutting it by a plane passing through its center). Where the implant is semicircular in some, but not all dimension, its shape will not be hemispherical. The shape can be aspherical on either or both of the superior and inferior surfaces to accommodate the acetabulum. Further, where there is more than one component, a combination of three dimensional shapes can be employed. For example, a first component can be hemispherical, while a second component is not, and so on.

Additionally, while these implants have been shown having from one to three components, it will be appreciated, that each component can be further modified into a plurality of components that engage with one another without departing from the scope of the invention.

It will further be appreciated by those of skill in the art that the design considerations taught in FIGS. 10-20 can be employed in designing implants for other joints, such as the knee, ankle, shoulder, elbow, and wrist. To avoid obscuring the invention, all possible configurations of the implants taught herein have not been shown.

C. The Shoulder

FIG. 21A is a frontal view of the osseous structures in the shoulder joint 300 such as the clavicle 302, scapula 304, glenoid fossa 306, acromion 308, coracoid process 310 and humerus 312. The cartilage covered areas 314, 316 are indicated by the oblique lines.

FIG. 21B is a view of an arthroplasty device 320 placed between the humeral head 313 and the glenoid fossa 306. The arthroplasty device 320 can have similar design features as the ones shown in FIGS. 4A-4R, e.g. a plurality of components, mobile bearing designs, attached and unattached designs, designs with varying thickness and curvatures, designs conforming to the humeral head 313 or glenoid fossa 306 or both, designs conforming to the articular cartilage and/or subchondral bone, designs with lips or members for stabilization purposes.

FIG. 21C is an oblique frontal cross-sectional view of an arthroplasty device 320 with a humeral contacting surface 322 that conforms at least partially to the shape of the humeral head 313 and a glenoid contacting surface 324 that conforms at least partially to the shape of the glenoid fossa 306.

FIG. 21D is an axial cross-sectional view of an arthroplasty device 520 with a humeral contacting surface 322 that conforms to the shape of the humeral head and a glenoid contacting surface 324 that conforms to the shape of the glenoid fossa 306.

FIG. 21E is an oblique frontal view of the shoulder joint illustrating the articular cartilage 316 and the superior and inferior glenoid labrum 306', 306'', respectively. FIG. 21F is an axial view of the shoulder joint illustrating the articular cartilage 316 and the anterior and posterior glenoid labrum 307', 307'', respectively.

FIG. 21G is an oblique frontal cross-sectional view of an arthroplasty device 320 with the humeral contacting surface 322 that conforms to the shape of the humeral head 313 and a glenoid contacting surface 324 that conforms to the shape of the glenoid 306 and the glenoid labrum (306', 306'). FIG. 21H is an axial cross-sectional view of an arthroplasty device 320 shown in FIG. 21G. As shown above, a humeral contacting surface 322 is provided that conforms to the shape of the humeral head 313 and a glenoid contacting surface 324 is provided that conforms to the shape of the glenoid 306 and the glenoid labrum.

FIG. 21I is an oblique frontal cross-sectional view of an alternate embodiment of an arthroplasty device 340 with the humeral contacting surface 342 that conforms to the shape of the humeral head 313 and a glenoid contacting surface 344 that conforms substantially to the shape of the glenoid 306. One or more protrusions or lips 346, 346' can be provided that extend superiorly and/or inferiorly. The lips can be configured to provide stabilization over the glenoid. FIG. 21J is an axial cross-sectional view of the arthroplasty device 340 shown in FIG. 21I with the humeral contacting surface 342 that conforms to the shape of the humeral head 313 and the glenoid contacting surface 344 that conforms substantially to the shape of the glenoid 306. One or more lips 346", 346'" can be provided that extend anteriorly and/or posteriorly providing stabilization over the glenoid 306.

FIG. 21K is an oblique frontal cross-sectional view of a dual component, "mobile-bearing" arthroplasty device 350 with the humeral contacting surface 354 of a first component 351 that conforms to at least a portion of the humeral head and a glenoid contacting surface 354 of a second component 353 that conforms to at least a portion of the shape of the glenoid. As will be appreciated by those of skill in the art, the radius (radii) of the two articulating implant surfaces can be selected to match or substantially match that of the humerus or the glenoid or both. Further the implant can have a contacting surface that conforms with the humerus or glenoid either substantially, or as much as necessary to achieve the desired correction and functional effect. Moreover, the center of rotation of the two articulating implant surfaces 356, 358 can be selected to match substantially the center of rotation of the humeral head. As will be appreciated by those of skill in the art, the two articulating implant surfaces 356,358 can have any shape including a flat surface.

FIG. 21L is an axial cross-sectional view of a dual component, "mobile-bearing" arthroplasty device shown in FIG. 21K. The humeral contacting surface 352 is configured as shown in this embodiment so that it conforms substantially to the shape of the humeral head 313 and the glenoid contacting surface 354 is configured in this embodiment so that it conforms substantially to the shape of the glenoid 306. The radius (radii) of the two articulating implant surfaces can be selected to match the surfaces of the humerus, the glenoid, or both. Moreover, the center of rotation of the two articulating implant surfaces can be selected to match substantially the center of rotation of the humeral head. FIG. 21M is an alternate embodiment showing the implant with an indentation on one component and a ball on a second component. The indent and ball configuration can be reversed such that it is on the opposing surface without departing from the scope of the invention. As will be appreciate the ball and socket arrangement shown will facilitate the movement of the implant components relative to each other but can assist in preventing undesirable movement of the components in operation.

FIG. 21N is an oblique frontal cross-sectional view of an alternate embodiment of a dual component, "mobile-bearing" arthroplasty implant 360. The implant 360 has a first component 362 and a second component 364. The glenoid component 364 is configured to have two surfaces. The first surface 363 is configured to articulate relative to the first component 362. The second surface 363 is configured to mate with the glenoid 306. The second, or glenoid, component 364 is attached to the glenoid using one or more anchors 365. The anchor 365 can be in the form of pegs or fins or other suitable configurations to achieve the desired result of anchoring the glenoid component 364 to the glenoid. These pegs or fins can be cemented, porous coated, or both. Similarly, the glenoid contacting surface 363 of the component 362 can be cemented, porous coated, or both. Preferably, only the anchor 365 extends into the subchondral bone.

Figure 21Q:
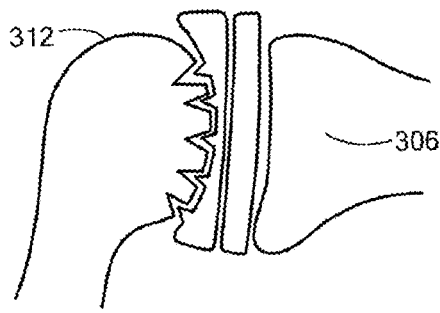

FIG. 21O is an oblique frontal cross-sectional view of an alternate embodiment of a dual component, "mobile-bearing" arthroplasty device 370. The humeral contacting component 372 is attached to the humeral head 312 using an attachment mechanism such as pegs or fins or, as illustrated in this example, spikes 373. These pegs, fins, teeth or spikes can be cemented, porous coated, or both. Similarly, the undersurface of the humeral component can be cemented or porous coated or both. Preferably, only the attachment mechanism itself (i.e., the pegs, fins or spikes) can extend through the subchondral bone. The pegs, fins, teeth or spikes can be pyramidal, conical, triangular, spherical, tubular, or protrusions of any kind and can be in a random configuration on the surface or an organized configuration (e.g., rows). As illustrated herein there is articular cartilage 374 on the glenoid side of the joint. The implant 370 can be designed to conform to the articular cartilage 374 or the subchondral bone, or both. As shown in FIGS. 21P and 21Q the fins or spikes can be alternating lengths and can be configured such they the fins are parallel to each other.

In another embodiment, the implant can be adapted to soft-tissue damage. For example, in the event of a rotator cuff tear, the implant can have an extension covering portions or all of the superior aspect of the humeral head. In this manner, superior migration of the humeral head as a result of the tear of the rotator cuff cannot lead to pathologic articulation of the humeral head with the acromioclavicular joint with resultant pain and disability. Instead, the superior aspect of the humeral head can articulate with extended member of the implant thereby avoid eburnation of the AC joint.

D. The Elbow

FIG. 22 is an oblique longitudinal view through the elbow joint 600 demonstrating the distal humerus 602, the olecranon 604 and the radial head 606. The cartilaginous surfaces are seen 603, 605, 607, respectively. An arthroplasty device 620 is illustrated interposed between the distal humerus and the articulating surfaces on the ulna 608 and radius 610. The arthroplasty device 620 can have similar design features as those illustrated with respect to the devices shown in FIGS. 10-20, e.g. single, dual, triple component; mobile bearing designs; attached and unattached designs; designs with varying thickness and curvatures; designs conforming to the humerus or ulna or radius or combinations thereof; designs conforming to the articular cartilage and/or subchondral bone, designs with lips or members for stabilization purposes. However, to avoid obscuring the invention, each possible permutation of design consideration taught in this application has not been illustrated for this joint.

E. The Wrist

FIG. 23A is a longitudinal view through the wrist joint 700 demonstrating the distal radius 702, the ulna 704 and several of the carpal bones which form a carpal row 706 (e.g. scaphoid, lunate, triquetral, capitate and hamate). An arthroplasty device 720 is illustrated interposed between the distal radius 702, the distal ulna 704 and the articulating surfaces of the proximal carpal row 706', 706", 706'". The arthroplasty device 720 conforms to the shape of the distal radius 702, the proximal carpal row 706, and, in this example, the triangular fibrocartilage (dotted lines) 708.

As will be appreciated by those of skill in the art, the arthroplasty device 720 can have design features similar to those described with relation to the devices shown in FIGS. 10-20, e.g. single, dual, triple component; mobile bearing designs; attached (e.g. to the distal radius) and unattached designs; designs with varying thickness and curvatures; designs conforming to the radius or ulna or carpals or combinations thereof; designs conforming to the articular cartilage and/or subchondral bone and also to other articular structures such as the triangular fibrocartilage; designs with lips or members for stabilization purposes.

FIG. 23B is a longitudinal view through the wrist joint 700 demonstrating the distal radius 702, the ulna 704 and several of the carpal bones 706. An arthroplasty device 720 is illustrated interposed between the distal radius 702, the distal ulna 704 and the articulating surfaces 706', 706", 706'" of the proximal carpal row 706. The arthroplasty device 720 is configured such that it conforms to at least a portion of the shape of the distal radius 702, the distal ulna 704, and the proximal carpal row 706.

FIG. 23C is a longitudinal view through the wrist joint 700 again demonstrating the distal radius 702, the ulna 704 and several of the carpal bones 706. An arthroplasty device 730 is shown interposed between the distal radius 702, the distal ulna 704 and the articulating surfaces 706', 706", 706'" of the proximal carpal row 706. The arthroplasty device 730 shown conforms substantially to the shape of the distal radius 702, the proximal carpal row 706 and the distal ulna 704 including the ulnar styloid 710. A lip 732 is seen extending along the medial aspect of the distal radius and the lateral aspect of the distal ulna 704 including the ulnar styloid 710; this can provide stabilization of the implant relative to these bones. One or more lips 732, or other suitably configured protrusions, can extend towards the dorsal or palmar aspect of any of the bones of the joint.

FIG. 23D is a longitudinal view of a dual component, "mobile-bearing" arthroplasty device 740. The device 740 has a first component 742 and a second component 744. Each component has a surface that articulates with a surface of the other component, 743, 745. The radii of the two articulating implant surfaces can be selected to match that of the radius 702 or the ulna 704 or the carpal bones 706 or combinations thereof. Moreover, the center of rotation of the two articulating implant surfaces can be selected to match or approximate the center of rotation of the joint 700. As will be appreciated by those of skill in the art, the two articulating implant surfaces 743, 745 can have any shape that facilitates the functioning of the joint, including a flat surface. Note the lips 746, 748 of the proximal component extending medially and laterally. Lips can also extend towards the dorsal or palmar aspect.

FIG. 23E is a longitudinal view of another dual component, "mobile-bearing" arthroplasty device 750, in this case without lips. The device 750 has a first component 752 and a second component 754. Each component has a surface that articulates with a surface of the other component, 753, 755. As evident from the cross-sectional view, the length of the first component's articulating surface 753 is longer than the length of the second component's articulating surface 755.

FIG. 23F is a longitudinal view of a dual component, "mobile-bearing" arthroplasty device 760. As depicted, the first component 762 facing the radius and ulna has been attached to these bones using an attachment mechanism or anchor 766. Suitable anchors 766 include pegs, as shown in this example, spikes and/or fins, to name a few. As will be appreciated by those of skill in the art, the attachment of the device 760 can be limited to attachment to one bone only (e.g. the ulna or the radius).

F. The Finger

FIG. 24 is a sagittal view through a finger 800. An arthroplasty device 820 is illustrated such that it is interposed between the metacarpal head 802 and the base of the proximal phalanx 804. The arthroplasty device 820 conforms to the shape of the metacarpal head 802 on one side 822 and the base of the proximal phalanx 804 on an opposing side 824. The arthroplasty device 820 can have similar design features as the ones seen in FIGS. 10-20, e.g. single, dual, triple component, mobile bearing designs, attached (e.g. to the metacarpal head or the base of the phalanx) and unattached designs, designs with varying thickness and curvatures, designs conforming to the proximal or the distal articular surface or combinations thereof, designs conforming to the articular cartilage and/or subchondral bone and also to other articular structures, designs with lips or members for stabilization purposes. Similar designs are applicable to the hind, mid and forefoot including the toes.

G. The Ankle

Figure 25A:
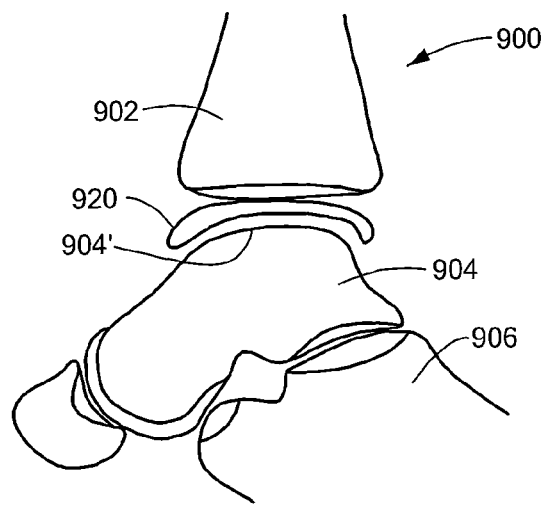

FIG. 25A is a sagittal view through the ankle joint 900 demonstrating the distal tibia 902, the talus 904 and calcaneus 906 and the other bones. The cartilaginous surfaces are also shown. An arthroplasty device 920 is illustrated interposed between the distal tibia 902 and the talar dome 904', In this example, the arthroplasty system 920 conforms to the shape of the talus 904. As will be appreciated by those of skill in the art, and discussed previously, the device can conform to the shape of the cartilage or the subchondral bone or both. The arthroplasty device 920 can have similar design features as the devices illustrated in FIGS. 10-20 and discussed above, e.g. single, dual, triple component, mobile bearing designs, attached and unattached designs, designs with varying thickness and curvatures, designs conforming to the tibia or talus or fibula or combinations thereof, designs conforming to the articular cartilage and/or subchondral bone, designs with lips or members for stabilization purposes.

Figure 25B:
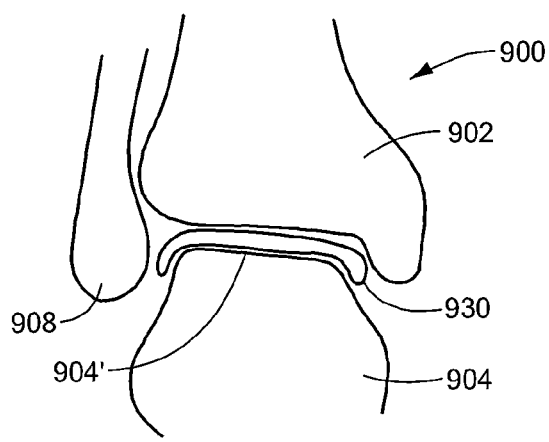

FIG. 25B is a coronal view through the ankle joint 900 illustrating the distal tibia 902, the distal fibula 908 and the talus 904. An arthroplasty device 930 is illustrated interposed between the distal tibia 902 and the talar dome 904'. In this example, the arthroplasty system 930 is shown conforming to the shape of the talus 904.

Figure 25C:
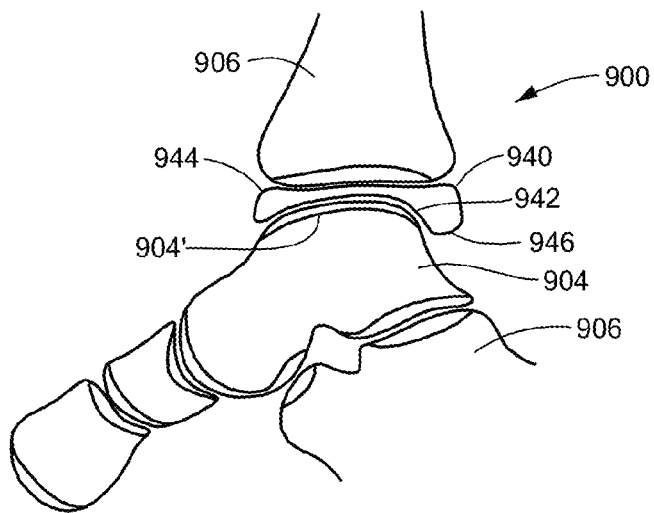

FIG. 25C is a sagittal view through the ankle joint 900 illustrating the distal tibia 902, the talus 904 and calcaneus 906 and the other bones. The cartilaginous surfaces are also shown. An arthroplasty device 940 is depicted interposed between the distal tibia 902 and the talar dome 904', In this example, the inferior surface of the arthroplasty system 942 conforms substantially to the shape of the talus 904. The superior surface 944 conforms substantially to the shape of the distal tibia 902 and fibula (908, not shown). A lip 946 is shown on the inferior surface 942 that engages the talus 904.

Figure 25D:
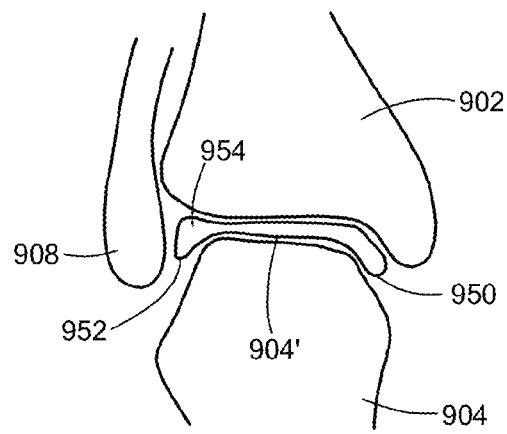

FIG. 25D is a coronal view through the ankle joint 900 illustrating the distal tibia 902, the distal fibula 908 and the talus 904. An arthroplasty device 950 is shown interposed between the distal tibia 902 and the talar dome 904', In this example, the inferior surface 952 of the arthroplasty system conforms to the shape of the talus 904. The superior surface 954 conforms to the shape of the distal tibia 902 and fibula 908.

H. The Toe

FIG. 26 is a sagittal view through a toe 1000. An arthroplasty device 1020 is illustrated interposed between the metatarsal head 1002 and the base of the proximal phalanx 1004. The arthroplasty device 1020 illustrated conforms to the shape of the metatarsal head on a first surface 1022 and the base of the proximal phalanx on a second surface 1024. As will be appreciated by those of skill in the art, the arthroplasty device can have similar design features as the ones seen in FIGS. 10-20, e.g. single, dual, triple component, mobile bearing designs, attached (e.g. to the metatarsal head or the base of the phalanx) and unattached designs, designs with varying thickness and curvatures, designs conforming to the proximal or the distal articular surface or combinations thereof, designs conforming to the articular cartilage and/or subchondral bone and also to other articular structures, designs with lips or members for stabilization purposes. Similar designs are applicable to the hind, mid and forefoot.

D. Device Manufacture, Composition and Properties

The devices described above, or any device manufactured according to the teachings of this invention, can be prepared from a variety of suitable materials known in the art A wide variety of materials find use in the practice of the present invention, including, but not limited to, plastics, metals, ceramics, biological materials (e.g., collagen or other extracellular matrix materials), hydroxyapatite, cells (e.g., stem cells, chondrocyte cells or the like), or combinations thereof. Based on the information (e.g., measurements) obtained regarding the defect and/or the articular surface and/or the subchondral bone, a suitable material can be selected. Further, using one or more of these techniques described herein, a cartilage replacement or regenerating material having a curvature that can fit into a particular cartilage defect, can follow the contour and shape of the articular surface, and can match the thickness of the surrounding cartilage can be formed. Moreover, using one or more of these techniques described herein, an articular device can be shaped that can fit into a joint space and that can follow the contour and shape of the articular surface or other articular structures. The material can include any combination of materials, and preferably includes at least one substantially non-pliable material.

Additionally, the material can have a gradient of hardness. Thus, for example, the gradient of hardness can decrease from the center of the device to an outer edge. Thus producing a device that has overall firmness, but which has a bit of give to the surface along some or all of the outside surfaces. Providing an exterior surface made of material with some give could enhance the implant's ability to mate with the joint. Alternatively, in some scenarios a device can be manufactured where the exterior surface has a Shore hardness value higher than its interior sections.

The exterior hardness of the devices will be suitable for the implant to perform within the joint. Suitable hardnesses will be obvious to those of skill in the art and can comprise a range. Typically, harnesses are discussed in terms of the Shore hardness scale and can range from that common for engineering grade plastics to hardened steel and titanium, and preferably on the portion of the Rockwell hardness scale typical of steels, hard plastics and ceramic materials. From the high hardness desired of the device, it is readily apparent that the device functions in a manner completely different from those of the prior art. The purpose of the device of the subject invention is to achieve a span-like effect to bridge the defective areas. However, in a composite variation, any single component (like a bioactive material component described below) can be softer than the supporting material.

Currently, joint repair systems, including devices, employ metal and/or polymeric materials. See, e.g., U.S. Pat. No. 6,203,576 to Afriat, et al., issued Mar. 20, 2001; U.S. Pat. No. 6,206,927 to Fell, et al., issued Mar. 27, 2001; and U.S. Pat. No. 6,322,588 to Ogle, et al.; issued Nov. 27, 2001 and references cited therein. Similarly, a wide-variety of metals can find use in the practice of the present invention, and can be selected based on any criteria, for example, based on resiliency to impart a desired degree of rigidity. Non-limiting examples of suitable metals include silver, gold, platinum, palladium, iridium, copper, tin, lead, antimony, bismuth, zinc, titanium, cobalt, stainless steel, nickel, iron alloys, cobalt alloys, such as Elgiloy™, a cobalt-chromium-nickel alloy, and MP35N, a nickel-cobalt-chromium-molybdenum alloy, and Nitinol™, a nickel-titanium alloy, aluminum, manganese, iron, tantalum, other metals that can slowly form polyvalent metal ions, for example to inhibit calcification of implanted substrates in contact with a patient's bodily fluids or tissues, and combinations thereof.

Suitable synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, polyether ketone ketone, ethylene vinyl acetates, polysulfones, nitrocelluloses, similar copolymers and mixtures thereof. Bioresorbable synthetic polymers can also be used such as dextran, hydroxyethyl starch, derivatives of gelatin, polyvinylpyrrolidone, polyvinyl alcohol, poly[N-(2-hydroxypropyl)methacrylamide], poly(hydroxy acids), poly (epsilon-caprolactone), polylactic acid, polyglycolic acid, poly(dimethyl glycolic acid), poly(hydroxy butyrate), and similar copolymers can also be used.

The polymers can be prepared by any of a variety of approaches including conventional polymer processing methods. Preferred approaches include, for example, injection molding, which is suitable for the production of polymer components with significant structural features, and rapid prototyping approaches, such as reaction injection molding and stereo-lithography. The substrate can be textured or made porous by either physical abrasion or chemical alteration to facilitate incorporation of the metal coating.

The polymer can be injected into a mold reflecting aspects of the articular surface(s) or other articular structures.

More than one metal and/or polymer can be used in combination with each other. And liquid metals can be used as well. For example, one or more metal-containing substrates can be coated with polymers in one or more regions or, alternatively, one or more polymer-containing substrate can be coated in one or more regions with one or more metals.

The device or parts thereof can be porous or porous coated. The porous surface components can be made of various materials including metals, ceramics, and polymers. These surface components can, in turn, be secured by various means to a multitude of structural cores formed of various metals. Suitable porous coatings include, but are not limited to, metal, ceramic, polymeric (e.g., biologically neutral elastomers such as silicone rubber, polyethylene terephthalate and/or combinations thereof) or combinations thereof. See, e.g., U.S. Pat. No. 3,605,123 to Hahn, issued Sep. 20, 1971; U.S. Pat. No. 3,808,606 to Tronzo, issued Apr. 23, 1974; U.S. Pat. No. 3,843,975 to Tronzo issued Oct. 29, 1974; U.S. Pat. No. 3,314,420 to Smith; U.S. Pat. No.

3,987,499 to Scharchach, issued Oct. 26, 1976; and German Offenlegungsschrift 2,306,552. There can be more than one coating layer and the layers can have the same or different porosities. See, e.g., U.S. Pat. No. 3,938,198 to Kahn, et al., issued Feb. 17, 1976.

The coating can be applied by surrounding a core with powdered polymer and heating until cured to form a coating with an internal network of interconnected pores. The tortuosity of the pores (e.g., a measure of length to diameter of the paths through the pores) can be important in evaluating the probable success of such a coating in use on a prosthetic device. See, also, U.S. Pat. No. 4,213,816 to Morris, issued Jul. 22, 1980. The porous coating can be applied in the form of a powder and the article as a whole subjected to an elevated temperature that bonds the powder to the substrate. Selection of suitable polymers and/or powder coatings can be determined in view of the teachings and references cited herein, for example based on the melt index of each.

Any of the devices described herein can also include one or more biological materials, either alone or in combination with non-biological materials. Non-limiting examples of biological materials include cells (e.g., fetal cartilage cells), biological polymers (e.g., collagen, elastin, silk, keratin, gelatin, polyamino acids, cat gut sutures, polysaccharides such as cellulose and starch), autografts, allografts, xenografts, etc. See, U.S. Pat. No. 5,478,739 to Slivka, et al., issued Dec. 26, 1995; U.S. Pat. No. 5,842,477 to Naughton, et al., issued Dec. 1, 1998; U.S. Pat. No. 6,283,980 to Vibe-Hansen, et al., issued Sep. 4, 2001; and U.S. Pat. No. 6,365,405 to Salzmann, et al. issued Feb. 4, 2002.

In certain embodiments, the device can include one or more separate (but preferably engageable) components. For example, a two-piece device can include two components, where each component includes a mating surface. The two components can be interlocking. When mated with one another the contoured faces oppose each other and form a device that fits within the defect intended to correct and provides a joint surface that mimics or replicates a natural joint surface. Any suitable interlocking mechanism can be used, including a slideable (e.g., keyway) system; an interlocking clasp; a ball and keyway interlocking system; a groove and flange system; etc. In some embodiments, the surfaces of the components that are engageable are curved. The curvature can be a reflection of one or more articular structures.

In other embodiments, the configuration of the devices changes upon deployment into the joint. Thus, the devices can be designed in an initial configuration. Upon deployment, the devices can assume a subsequent configuration that is different from the initial configuration. For example, the devices can be multiple-component devices that, in a first configuration, has a small profile or small three-dimensional shape. Upon deployment the surgeon allows (or causes) the device to assume a second configuration, which can have a greater profile or overall three-dimensional shape. The device can be self-forming into its secondary configuration or, alternatively, can be manipulated, for example by mechanical means (e.g., unfolding the device or sliding the components of the device relative to each other so that they assume the larger second configuration). One advantage of such embodiments is that smaller incisions are required. The device can, for example, be deployed arthroscopically in this manner. Thus, assuming the subsequent configuration can be automatic, semi-automatic, or manual.

The methods and compositions described herein can be used to replace only a portion of the articular surface, for example, an area of diseased cartilage or lost cartilage on the articular surface. In these systems, the articular surface repair system can be designed to replace only the area of diseased or lost cartilage or it can extend beyond the area of diseased or lost cartilage, e.g., 3 or 5 mm into normal adjacent cartilage. In certain embodiments, the prosthesis replaces less than about 70% to 80% (or any value therebetween) of the articular surface (e.g., any given articular surface such as a single femoral condyle, etc.), preferably, less than about 50% to 70% (or any value therebetween), more preferably, less than about 30% to 50% (or any value therebetween), more preferably less than about 20% to 30% (or any value therebetween), even more preferably less than about 20% of the articular surface.

E. Alternate Attachment Mechanisms

As will be appreciated by those of skill in the art, a variety of attachment mechanisms can be provided to attach the implants within a target joint. For example an attachment mechanism can be ridges, pegs, pins, cross-members, and other protrusions that engage the implant mating surface. These protrusions or mechanisms can have a variety of shapes and cross-sections including, pyramidal, triangular, conical, spherical, cylindrical, circular, etc. A single attachment mechanism can be used or a plurality of mechanisms, as desired. Combinations of shapes can be used to achieve better placement. Where a plurality of mechanisms is used, the mechanisms can be formed in an organized pattern (e.g., rows, circles, etc.) or a disorganized (random) pattern, is a cone shaped portion provided on the undersurface of the implant. Further, where more than one attachment mechanism is used the orientation relative to one another can be parallel or non-parallel.

In one example a cone is positioned on the undersurface of the device such that it is placed at the bottom of, for example, the concave part of the tibial cartilage. The cone can, like the sphere, also be separated from the undersurface of the implant by, for example, a cylindrical element. Other geometries suitable for attachment will be apparent to those of skill in the art.

In another example, one or more cylindrical, or substantially cylindrical, pins are provided on a surface of an implant. The pins are oriented such that each pin is parallel to at least one other pin.

Yet another example for a semi-fixed attachment mechanism is a magnet which is placed underneath the subchondral bone layer, for example in the tibia. Another magnet or magnetic material is embedded into or attached to the undersurface of the device, which is then held in place by the first magnet. As will be appreciated by a person of skill in the art, a plurality of magnets associated with each surface can be used. Further, a combination of magnets can be used such that each surface has one or more magnets having a first pole and one or more magnets having a second pole that engage with a magnet with an opposite pole magnet on, or associated with, the opposing surface. Such an arrangement might be useful where there is a desire to prevent rotation of the device within the joint while ensuring communication between the two surfaces.

Yet another example for such attachment mechanisms is a screw or anchor that can be inserted into the subchondral bone of the tibia at the bottom of the concave portion of the tibial cartilage. The device can be fixed to the screw or anchor or can have a semi-fixed design, for example by incorporating a slot which slides over the screw or anchor.

The implant height can be adjusted to correct articular malalignment or axis deviation(s). For example, in a knee joint, the articular height can be adjusted to correct for varus or valgus deformity. Such correction can be determined using measurements of the axis or axes of the joint as well as neighboring joints. For example, a CT or MRI scan or a weight-bearing radiograph of the extremity can be used for this purpose.

Implant thickness can also be selected or adjusted to correct the presence of ligamentous laxity. In a knee joint, for example, a slightly thicker implant can be selected to account for laxity or tear of one or more cruciate or collateral ligaments. The increase in implant thickness can be uniform or non-uniform, e.g. predominantly at the peripheral margin. The surgeon can use one or more trial prosthesis or actual implants intraoperatively to test which implant thickness yields the most preferred result with regard to articular and implant laxity.

V. Implantation

The devices described herein are typically implanted into the area of a joint defect. Implantation can be performed with the cartilage replacement or regenerating material still attached to the base material or removed from the base material. Any suitable methods and devices can be used for implantation, for example, devices as described in U.S. Pat. No. 6,375,658 to Hangody, et al. issued Apr. 23, 2002; U.S. Pat. No. 6,358,253 to Torrie, et al. issued Mar. 19, 2002; U.S. Pat. No. 6,328,765 to Hardwick, et al., issued Dec. 11, 2001; and International Publication WO 01/19254 to Cummings, et al., published Mar. 22, 2001.

The implants can be inserted using arthroscopic assistance. The device does not require the 15 to 30 cm incision utilized in certain unicompartmental and total knee arthroplasties. The procedure is performed under regional anesthesia, typically epidural anesthesia. A tourniquet can be applied to a more proximal portion of the extremity. The region of the body containing the joint to be repaired is prepped and draped using a sterile technique. In the case of the knee, for example, a stylette is used to create two small 2 mm ports at the anteromedial and the anterolateral aspect of the joint using classical arthroscopic technique. The arthroscope is inserted via the lateral port. The arthroscopic instruments are inserted via the medial port. A cartilage defect can be visualized using the arthroscope. A cartilage defect locator device can be placed inside the diseased cartilage. The probe can have a U-shape, with the first arm touching the center of the area of diseased cartilage inside the joint and the second arm of the U remaining outside the joint. The second arm of the U indicates the position of the cartilage relative to the skin. The surgeon marks the position of the cartilage defect on the skin. A 3 cm incision is created over the defect. Tissue retractors are inserted and the defect is visualized.

The implant is then inserted into the joint. Anterior and posterior positions of the implant can be color-coded. For example, the anterior peg can be marked with a red color and a small letter "A", while the posterior peg can be green color and a marked with a small letter "P". Similarly, the medial aspect of the implant can be color-coded yellow and marked with a small letter "M" while the lateral aspect of the implant can be marked with a small letter "L".

Areas of cartilage can be imaged as described herein to detect areas of cartilage loss and/or diseased cartilage. The margins and shape of the cartilage and subchondral bone adjacent to the diseased areas can be determined. The thickness of the cartilage can be determined. The shape of the menisci or other articular structures can be determined. The size and shape of the device is determined based on one or more of the above measurements. In particular, the repair system is either selected (based on best fit) from a catalogue of existing, pre-made implants with a range of different sizes and curvatures or custom-designed or patient specific using CAD/CAM technology. The custom designed implant can be generated using one or more patient dependent parameters. The patient dependent parameters can be obtained using one or more measurements of the patient's joint to be repaired. Further, the library of existing shapes can be on the order of about 30 sizes. As will be appreciated by those of skill in the art, the library can contain more than 30 shapes or less than 30 shapes, if desired, without departing from the scope of the invention.

More specifically, to implant a device within the hip joint, the surgeon would make a small incision as described above. Tissue retractors as well as other surgical instruments as are commonly used for hip surgery can be used in order to expose the hip joint. The capsule can be opened subsequently. A second surgeon can pull on the femur or tibia in order to open up the space between the femoral head and the acetabulum. The primary surgeon performing the procedure can then insert the arthroplasty device into the joint. If necessary, the surgeon can cut the ligamentum capitis femoris and debride portions of the articular surface, for example in order to remove torn labral tissue or cartilage flaps. The surgeon also has the option to remove the fat located in the area of the pulvinar.

Alternatively, where the arthroplasty system is composed of a self-expandable material, e.g. Nitinol, the surgeon can obtain entry to the hip via a standard or a modified arthroscopic approach. The implant can then be delivered via the same or a second portal or, alternatively, via a small incision. Once inside the joint, the implant can expand and take its final shape. In order to facilitate placement of the expandable implant, a guide or mold can be used. The guide or mold can be adapted to the 3D contour of the femoral or acetabular articular surface and can be placed in the intended position for the implant. The implant can then be advanced along the guide or, for example, within a hollow chamber inside the guide or mold. Once the implant has reached its intended position, the guide or mold can be removed with the implant remaining in place.

VI. Device Molds

In another embodiment of the invention, a container or well can be formed to the selected specifications, for example to match the material needed for a particular subject or to create a stock of repair and/or materials in a variety of sizes. The size and shape of the container can be designed using the thickness and curvature information obtained from the joint and from the cartilage defect. More specifically, the inside of the container can be shaped to follow any selected measurements, for example as obtained from the cartilage defect(s) of a particular subject. The container (mold) can be filled with a replacement material to form the device that will be implanted.

Molds can be generated using any suitable technique, for example computer devices and automation, e.g. computer assisted design (CAD) and, for example, computer assisted modeling (CAM). Because the resulting material generally follows the contour of the inside of the container it can better fit the defect itself and facilitate integration.

VII. Implantation Guides and Surgical Tools

The molds described above can also be used to design surgical implantation guides and tools having at least one outer surface that matches or nearly matches the contour of the underlying articular surface (bone and/or cartilage). In certain embodiments, two or more outer surfaces match the corresponding articular surfaces. The tool as a whole can be round, circular, oval, ellipsoid, curved or irregular in shape. The shape can be selected or adjusted to match or enclose an area of diseased cartilage or an area slightly larger than the area of diseased cartilage. Alternatively, the tool can be designed to be larger than the area of diseased cartilage. The tool can be designed to include the majority of or the entire articular surface. Two or more tools can be combined, for example for two or more articular surfaces.

One or more electronic images can be obtained providing object coordinates that define the articular and/or bone surface and shape. The biomechanical axes of the joint can also be defined, for example using an imaging test such as a CT or MRI scan or a standing, weight-bearing radiograph. For example, if surgery is contemplated for a knee joint, a CT scan or a spiral CT scan can be obtained through the knee joint. The CT scan can be limited to the knee joint region and the distal femur and proximal tibia. Alternatively, the scan can include images through the hip joint and, optionally, also the ankle joint. In this manner, the anatomic axes can be defined and the preferred planes for surgical placement of a knee implant can be selected. The scan can be contiguous.

Alternatively, selected scan planes can be obtained through the hip and ankle region in order to define the anatomic axes. The CT scan can be combined with intra-articular contrast administration in order to visualize the articular cartilage. In another example, a non-contrast CT scan can be used. If no contrast is used, the residual cartilage thickness can be estimated, for example, using a reference database of age, sex, race, height and weight matched individuals. In advanced arthritis, a reduction in normal cartilage thickness can be assumed. For example, in a knee joint, cartilage thickness can be assumed to be zero or near zero in the weight-bearing region in patients with advanced arthritis, while in the posterior non-weight-bearing regions a value of 2 mm or less can be selected. These estimated cartilage thickness can then be added to the curvature of the subchondral bone to provide an estimate of the shape of the articular surface. If an MRI is used, a high resolution scan can be obtained through the knee in which the surgeon is contemplating the surgery. This scan is advantageous for defining the articular geometry. The high resolution scan can be supplemented with a scan using lower resolution through adjacent joints and bones in order to define the anatomic axes.

If a total knee arthroplasty is contemplated, the high resolution scan can be acquired in the knee joint, while lower resolution scans can be acquired in the hip joint and, optionally, the ankle joint. Such lower resolution scans can be obtained with the body coil or a torso phased array coil.

Imaging tests can also be combined. For example, a knee MRI scan can be used to define the 3D articular geometry of the knee joint including subchondral bone and cartilage. The knee MRI scan can be combined with a standing, weight-bearing x-ray of the extremity that describes the anatomic axes. In this manner, object coordinates and anatomic axes can be derived that can be used to define the preferred planes for surgical intervention.

Object coordinates can be utilized to either shape the device to adapt to the patient's anatomy, e.g. using a CAD/CAM technique or, alternatively, to select a pre-made device that has a good fit with a patient's articular anatomy. As noted above, the tool can have a surface and shape that can match all or portions of the articular or bone surface and shape, e.g. similar to a "mirror image" of the device to be implanted. The tool can include apertures, slots and/or holes to accommodate surgical instruments such as drills and saws and the like. The tool can be used for partial articular replacement as well as total joint replacement. For example, in total knee arthroplasty, the tool can be used for accurate placement of the cut planes needed for implant insertion. In this manner, a more reproducible implant position can be achieved with the potential to improve clinical outcomes and long-term implant survival.

The tool can have one, two or more components. One part of the tool can be made of metal while other can be made of plastic. For example, the surface that is touching the articular surface during the surgery can be made of plastic. In this manner, it is easy and cheap to manufacture, for example using rapid prototyping techniques. The plastic component can be made individually for each patient or pre-selected from a range of existing size. The portion(s) of the plastic component that points away from the articular surface can have the same surface geometry, e.g. block-like, in all patients. In this manner, a pre-fabricated metal component can be applied to the plastic component. The metal component can include the surgical guides, e.g. openings for saws or drills. The plastic component will typically have openings through which the surgical instruments can be advanced to the bone or cartilage without having to damage the plastic.

The plastic component determines the position of the metal component and surgical guides in relation to the articular surface. Spacers can be introduced between both components, for example in order to adjust the depth of bone cuts. Thus, in a knee joint, the surgeon can test for flexion and extension gap and, using the spacers, adjust the gaps and select the most appropriate cut planes. Moreover, if two or more components are used, rotational adjustment can be allowed between the components. In this manner, the surgeon can, for example, balance the medial and lateral compartments in a knee joint. After any optional rotational adjustments have been made, the components can be fixed relative to each other or relative to the bone or cartilage before the surgeon places any cuts or makes any other manipulations.

The component(s) and tools can be designed to be compatible with existing surgical instrument sets used for arthroplasty, e.g. total knee arthroplasty. Notably, the tool(s) can help reduce the number of surgical instruments used for arthroplasty. Finally, this embodiment can help improve postoperative alignment of the implant(s) relative to the desired location or anatomic axes thereby decreasing prosthetic loosening, implant wear, stresses on bone and thereby improving long-term outcomes.

Typically, a position is chosen that can result in an anatomically desirable cut plane or drill hole orientation for subsequent placement of an implant. Moreover, the guide device can be designed so that the depth of the drill or saw can be controlled, e.g., the drill or saw cannot go any deeper into the tissue than defined by the thickness of the device, and the size of the hole in block can be designed to essentially match the size of the implant. Information about other joints or axis and alignment information of a joint or extremity can be included when selecting the position of these slots or holes. The guides can be prepared for any of the implants of the invention.

Turning now to specific examples of implantation guides shown in FIGS. 28 and 17, these examples are provided for illustration purposes. FIG. 28 illustrates a plan view of an implantation guide 1100 suitable for use with the implant shown in FIG. 8L. A joint conforming body is provided 1110. The joint conforming body is configured to have at least one exterior surface configuration that matches an exterior surface configuration of the implant 100 to be used. A handle 1112 is provided to enable the user to place the guide in the joint where the implant 100 will be placed. Additionally, an anchor guide 1114 is provided. In this instance the anchor guide 1114 is in an opening within the body 1110 in the shape of a cross. As will be appreciated by those of skill in the art, the anchor guide 1114 can assume a variety of shapes, as appropriate, to enable the guide to perform its intended function. In this instance, the cross-shape enables the user to identify the articular surface of the joint where the anchor 112 (shown in FIG. 3L) is positioned on the joint. Once the guide 1100 is placed on the target articular surface, the anchor guide 1114 can be used to either: mark the location where the anchor can access the joint; confirm the location where the anchor can access the joint; prepare the articular surface at the location where the anchor can be located; or a combination thereof.

Turning now to the guide 1200 shown in FIGS. 25A-B, plan views of a guide suitable for use with the implant shown in FIGS. 9A-C are shown. A body is provided 1210. The body is configured to have at least one exterior surface that matches, or nearly matches, an exterior surface configuration of an implant 150 to be implanted. A handle 1212 is provided to enable the user to place the guide on a joint surface where the implant 150 can be placed. Additionally, one or more anchor guides 1214 are provided. In this instance the anchor guides 1214 (1214', 1214", 1214''') are circular, or substantially circular, openings within the body 1210 that are large enough in diameter to accept the drill bits for drilling the holes inside the bone in which the pins of the anchors 156 of the implant 150 will be placed. As will be appreciated by those of skill in the art, the anchor guide 1214 can assume a variety of shapes, as appropriate, to enable the guide to perform its intended function. Additional guides 1216 can be provided. The additional guides can perform the same function as the primary guides 1214 or can perform a secondary function. In this instance, the anchor guides 1214 can be used to identify the articular surface of the joint where the anchors 156 (shown in FIGS. 9B-C) can be positioned on the joint. Once the guide 1200 is placed on the target articular surface, the anchor guide 1214 can be used to either; mark the location where the anchor can be access the joint; confirm the location where the anchor can access the joint; prepare the articular surface at the location where the anchor can be located; or a combination thereof. Additionally, guides 1216 can be used to mark the location where the anchor can access the joint; confirm the location where the anchor can access the joint; prepare the articular surface at the location where the anchor can be located; or a combination thereof.

In another embodiment, a frame can be applied to the bone or the cartilage in areas other than the diseased bone or cartilage. The frame can include holders and guides for surgical instruments. The frame can be attached to one or preferably more previously defined anatomic reference points. Alternatively, the position of the frame can be cross-registered relative to one, preferably more anatomic landmarks, using an imaging test, for example one or more fluoroscopic images acquired intraoperatively. One or more electronic images can be obtained providing object coordinates that define the articular and/or bone surface and shape. These objects coordinates can be entered or transferred into the device, for example manually or electronic, ally, and the information can be used to move one or more of the holders or guides for surgical instruments. Typically, a position is chosen that can result in a surgically or anatomically desirable cut plane or drill hole orientation for subsequent placement of an or other implant including hemi-, unicompartmental or total arthroplasty. Information about other joints or axis and alignment information of a joint or extremity can be included when selecting the position of these slots or holes.

Because of its anatomic alignment with the chosen underlying articular surface, the preferred location and orientation of saw guides, drill holes or guides for reaming devices can be created in the appropriate tool. Intraoperatively, the surgical assistance tool is applied to the articular surface(s) with which it achieves the near or perfect anatomic fit. The surgeon can then introduce a saw (or other tool) through the guide(s) and prepare the joint (cartilage or bone) for the procedure. By cutting the cartilage and/or bone along anatomically defined planes, a more reproducible placement can be achieved which ultimately leads to improved postoperative results by optimizing biomechanical stresses.

The anatomically correct tools described herein can be constructed by a number of methods and can be made of any material, preferably a translucent material such as plastic, Lucite, silastic, SLA or the like, and typically is a block-like shape prior to molding. Furthermore, re-useable tools (e.g., molds) can be also be created and employed. Non-limiting examples of re-useable materials include putties and other deformable materials (e.g., an array of adjustable closely spaced pins that can be configured to match the topography of a joint surface). In these embodiments, the mold can be created directly from the joint during surgery or, alternatively, created from an image of the joint, for example, using one or more computer programs to determine object coordinates defining the surface contour of the joint and transferring (e.g., dialing-in) these co-ordinates to the tool. Subsequently, the tool can be aligned accurately over the joint and, accordingly, the drill and implant can be more accurately placed in and over the articular surface.

In both single-use and re-useable embodiments, the tool can be designed so that the depth of the block controls the depth of the drill or saw, i.e., the drill or saw cannot go any deeper into the tissue than the depth of block, and the size of the hole in block can be designed to essentially match aspects of the size of the implant. The tool can be used for general prosthesis implantation, including, but not limited to, the articular repair implants described herein and for reaming the marrow in the case of a hemi-, unicompartmental or total arthroplasty or other articular systems including biological repair.

These surgical tools can also be used to remove an area of diseased cartilage or an area slightly larger than the diseased cartilage.

Identification and preparation of the implant site and insertion of the implant can be supported by an image-guided surgery system (surgical navigation system). In such a system, the position or orientation of a surgical instrument with respect to the patient's anatomy can be tracked in real-time in one or more 2D or 3D images. These 2D or 3D images can be calculated from images that were acquired preoperatively, such as MR or CT images. The position and orientation of the surgical instrument is determined from markers attached to the instrument. These markers can be located by a detector using, for example, optical, acoustical or electromagnetic signals. Surgical navigation systems can also be used without image guidance, for example, by identifying anatomic axes with use of motion studies of an extremity.

In still other embodiments, the surgical tools described herein can include one or more materials that harden to form a mold of the articular surface. A wide-variety of materials that harden in situ have been described including polymers that can be triggered to undergo a phase change, for example polymers that are liquid or semi-liquid and harden to solids or gels upon exposure to air, application of ultraviolet light, visible light, exposure to blood, water or other ionic changes. (See, also, U.S. Pat. No. 6,443,988 and documents cited therein). Non-limiting examples of suitable curable and hardening materials include polyurethane materials (e.g., U.S. Pat. No. 6,443,988 to Felt, et al., issued Sep. 3, 2002; U.S. Pat. No. 5,288,797 to Khalil, et al., issued Feb. 22, 1994; U.S. Pat. No. 4,098,626 to Graham, et al., issued Jul. 4, 1978, and U.S. Pat. No. 4,594,380 to Chapin, et al., issued Jun. 10, 1986; and Lu et al. (2000) BioMaterials 21(15):1595-1605 describing porous poly(L-lactide acid foams); hydrophilic polymers as disclosed, for example, in U.S. Pat. No. 5,162,430 to Rhee, et al., issued Nov. 10, 1992 hydrogel materials such as those described in Wake et al. (1995) Cell Transplantation 4(3):275-279, Wiese et al. (2001) J. Biomedical Materials Research 54(2):179-188 and Marler et al. (2000) Plastic Reconstruct. Surgery 105(6): 2049-2058; hyaluronic acid materials (e.g., Duranti et al. (1998) Dermatologic Surgery 24(12):1317-1325); expanding beads such as chitin beads (e.g., Yusof et al. (2001) J. Biomedical Materials Research 54(1):59-68); and/or materials used in dental applications (See, e.g., Brauer and Antonucci, "Dental Applications" pp. 257-258 in "Concise Encyclopedia of Polymer Science and Engineering" and U.S. Pat. No. 4,368,040 to Weissman, issued Jan. 11, 1983). Any biocompatible material that is sufficiently flowable to permit it to be delivered to the joint and there undergo complete cure in situ under physiologically acceptable conditions can be used. The material can also be biodegradable.

The curable materials can be used in conjunction with a surgical tool as described herein. For example, the surgical tool can include one or more apertures therein adapted to receive injections and the curable materials can be injected through the apertures. Prior to solidifying in situ the materials can conform to the articular surface facing the surgical tool and, accordingly, can form an impression of the surface upon hardening thereby recreating a normal or near normal articular surface. In addition, curable materials or surgical tools can also be used in conjunction with any of the imaging tests and analysis described herein, for example by molding these materials or surgical tools based on an image of a joint.

Turning now to FIGS. 27A-D, the steps of the method of implanting the devices taught in this invention are shown. First, the user makes an incision to access the target joint 2610. Thereafter the joint surface is prepared using the implant guide 2620. Preparation of the joint surface can include, for example, identifying where the implant can reside in the joint, marking where the implant can attach, and/or preparing the articular surface to receive the implant. This preparation process can be repeated as necessary. As those of skill in the art will understand, in preparing the joint surface, the user can first identify where the implant will reside and then prepare the surface by marking the articular surface or removing bone or cartilage. Once the surface of the joint has been prepared, the implant is installed 2640. Installing the implant can be by either placing the implant on the surface or by adhering the implant to the surface using the techniques described herein. After the implant has been installed within the joint, the wound is closed 2650.

Figure 27A:
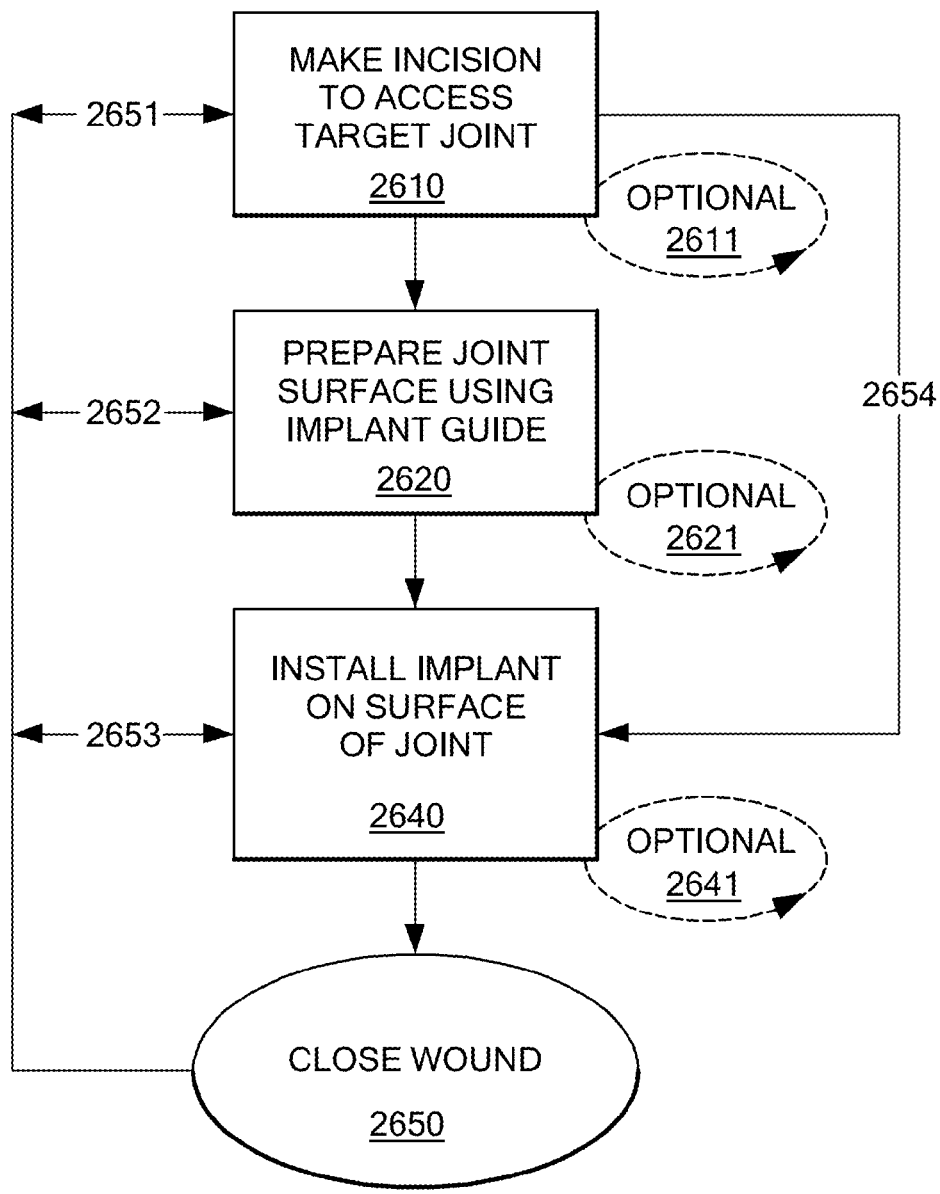
Figure 27B:
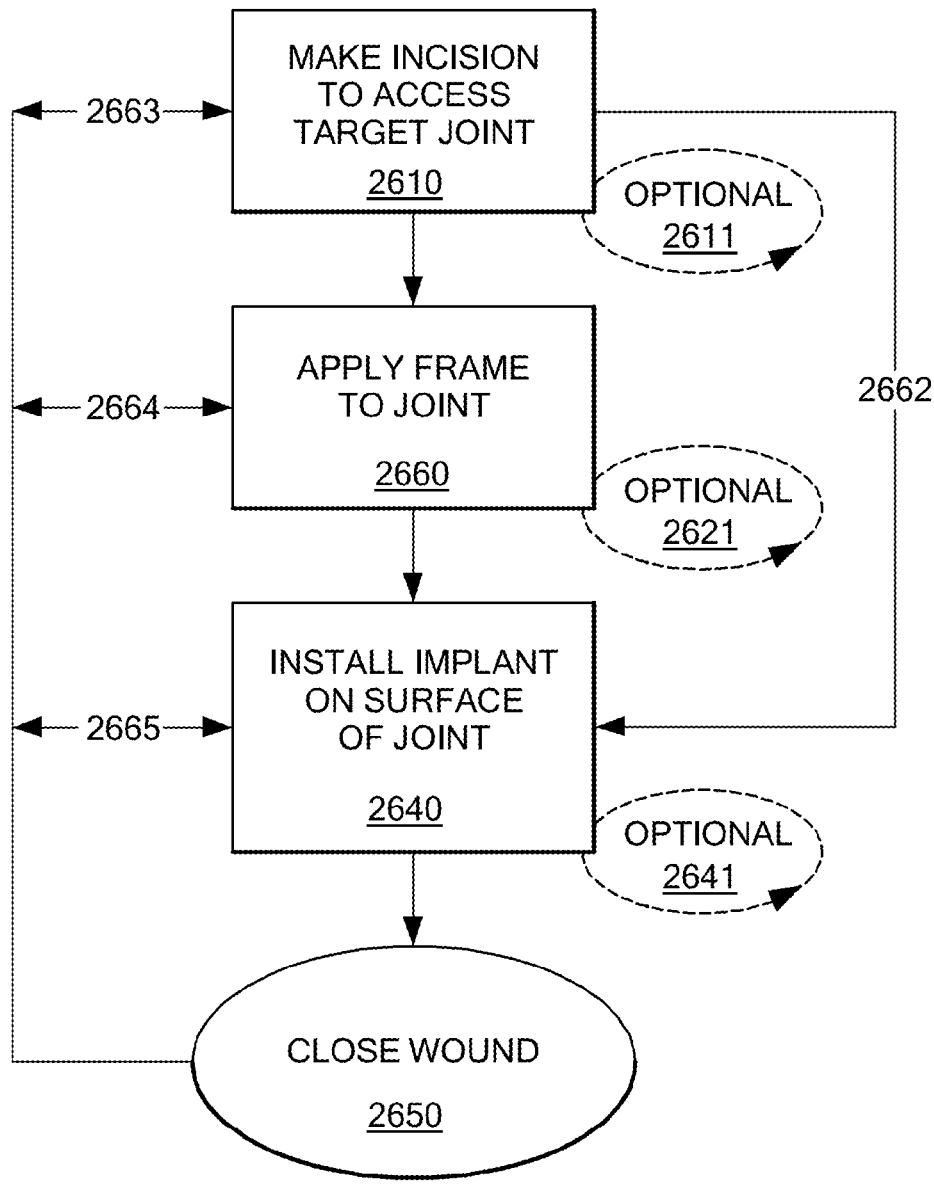

Turning now to the steps shown in FIG. 27B, the user makes an incision to access the target joint 2610. Thereafter a frame is attached to the joint 2660. Although not shown in this flow chart, the steps of preparing the joint shown in FIG. 27A can be performed. The implant is then installed 2665 onto the frame. After the implant has been installed within the joint, the wound is closed 2650.

Figure 27C:
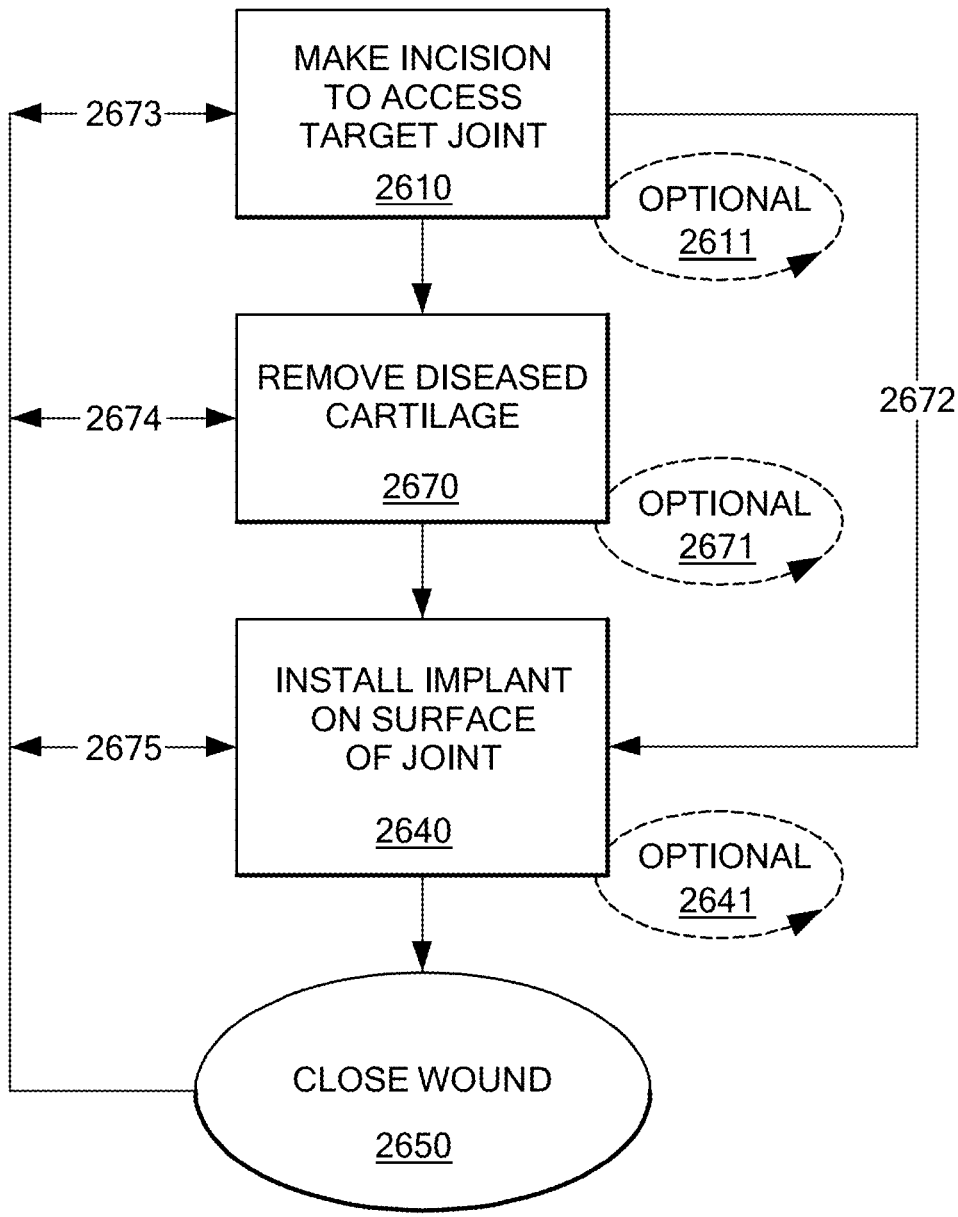

Turning now to the steps shown in FIG. 27C, the user makes an incision to access the target joint 2610. Thereafter diseased cartilage is removed from the joint 2670. Although not shown in this flow chart, the additional steps of preparing the joint shown in FIG. 27A can also be performed without departing from the scope of the invention. The implant is then installed 2675. After the implant has been installed within the joint, the wound is closed 2650.

Figure 27D:
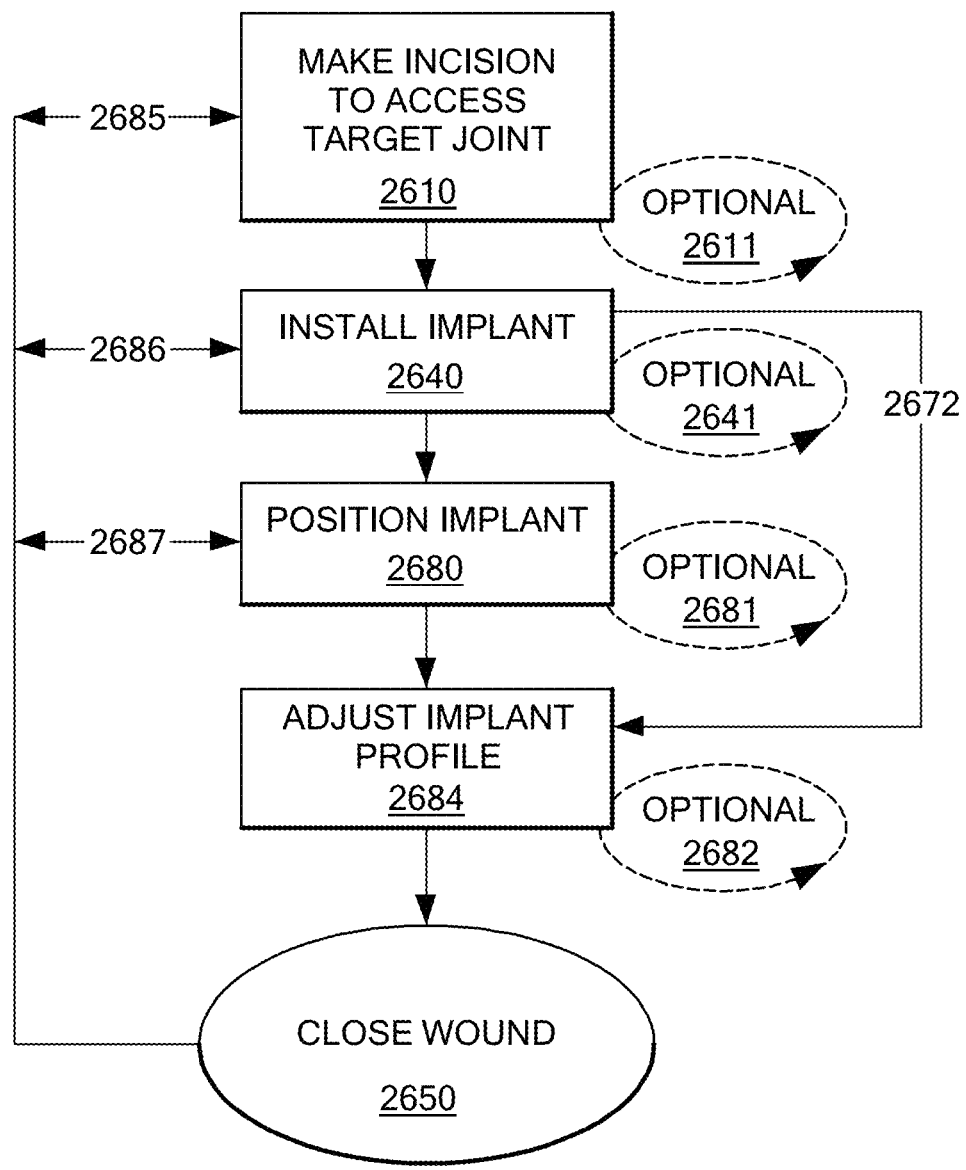

Turning now to the steps shown in FIG. 27D, the user makes an incision to access the target joint 2610. Although not shown in this flow chart, the additional steps of preparing the joint shown in FIG. 27A can also be performed without departing from the scope of the invention. Thereafter the implant is inserted 2680. The position of the implant is then optionally adjusted 2682. After the implant has been inserted and positioned, the profile of the implant is adjusted 2684. After the implant has been installed within the joint and adjusted, the wound is closed 2650. The implant height or profile selected can be chosen to alter the load bearing ability relative to the joint. Additionally the implant height can be adjusted to account for anatomic malalignment of bones or articular structures.

VII. Kits

Also described herein are kits comprising one or more of the methods, systems and/or compositions described herein. In particular, a kit can include one or more of the following: instructions (methods) of obtaining electronic images; systems or instructions for evaluating electronic images; one or more computer means capable of analyzing or processing the electronic images; and/or one or more surgical tools for implanting an implant. The kits can include other materials, for example, instructions, reagents, containers and/or imaging aids (e.g., films, holders, digitizers, etc.).

The following examples are included to more fully illustrate the present invention. Additionally, these examples provide preferred embodiments of the invention and are not meant to limit the scope thereof.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and its equivalence.

What is claimed is:

1. A tibial implant for implantation in a knee joint of a patient, comprising:
   a weight bearing surface configured to articulate with an opposing surface along an articulating region in a generally sagittal direction when the tibial implant is implanted in the knee joint of the patient, and a bone-facing surface configured to abut a surface of a tibia of the patient when the tibial implant is implanted in the knee joint of the patient, wherein the weight bearing surface includes at least a convex weight bearing surface portion in a generally anteroposterior direction and a concave weight bearing surface portion in a generally anteroposterior direction.

2. The knee implant system of claim 1, wherein the concave weight bearing surface portion is positioned posteriorly relative to the convex weight bearing surface portion.

3. The knee implant system of claim 1, wherein the concave weight bearing surface portion is positioned anteriorly relative to the convex weight bearing surface portion.

4. The knee implant system of claim 1, wherein the concave weight bearing surface portion substantially is positioned anteriorly relative to the convex weight bearing surface portion, and further comprising a second concave weight bearing surface portion substantially in an anteroposterior direction that is positioned posteriorly relative to the convex weight bearing surface portion.

5. The knee implant system of claim 1, wherein the weight bearing surface is curved in a mediolateral direction.

6. The knee implant system of claim 1, wherein the concave weight bearing surface portion is curved in a mediolateral direction.

7. The knee implant system of claim 1, wherein the convex weight bearing surface portion is curved in a mediolateral direction.

8. The knee implant system of claim 1, wherein the weight bearing surface is concave substantially in a coronal plane.

9. The knee implant system of claim 1, wherein the concave weight bearing surface portion is concave substantially in a coronal plane.

10. The knee implant system of claim 1, wherein the convex weight bearing surface portion is concave substantially in a coronal plane.

11. A knee implant for implantation in a knee joint of a patient, comprising:
a femoral component, and
a tibial component configured to be implanted in a lateral compartment of a knee joint and having a weight bearing surface configured to articulate with an opposing surface of the femoral component and extending in a generally sagittal direction when the tibial implant is implanted in the knee joint of the patient, and a bone-facing surface configured to abut a surface of a tibia of the patient when the tibial implant is implanted in the knee joint of the patient, wherein the weight bearing surface includes at least one convex weight bearing surface portion in a generally anteroposterior direction, wherein the weight bearing surface includes a concave weight bearing surface portion substantially in an anteroposterior direction.

12. The knee implant of claim 11, wherein the weight bearing surface includes a concave weight bearing surface portion substantially in an anteroposterior direction that is positioned posteriorly relative to the convex weight bearing surface portion.

13. The knee implant of claim 11, wherein the weight bearing surface includes a concave weight bearing surface portion substantially in an anteroposterior direction that is positioned anteriorly relative to the convex weight bearing surface portion.

14. The knee implant of claim 11, wherein the weight bearing surface includes a first concave weight bearing surface portion substantially in an anteroposterior direction that is positioned anteriorly relative to the convex weight bearing surface portion, and a second concave weight bearing surface portion substantially in an anteroposterior direction that is positioned posteriorly relative to the convex weight bearing surface portion.

15. The tibial knee implant of claim 11, wherein the weight bearing surface is curved in a mediolateral direction.

16. The tibial knee implant of claim 11, wherein the weight bearing surface is concave substantially in a coronal plane.

17. A tibial implant for implantation on a tibia of the patient, comprising:
a weight bearing surface configured to articulate with an opposing surface along an articulating region in a generally sagittal direction when the tibial implant is implanted in the knee joint of the patient, and a bone-facing surface configured to abut a surface of a tibia of the patient when the tibial implant is implanted in the knee joint of the patient, wherein the tibial lateral weight bearing surface includes at least one convex weight bearing surface portion in a generally mediolateral direction, wherein the weight bearing surface includes a concave weight bearing surface portion substantially in an anteroposterior direction.

18. The tibial implant of claim 17, wherein the weight bearing surface includes a concave weight bearing surface portion substantially in an anteroposterior direction that is positioned posteriorly relative to the convex weight bearing surface portion.

19. The tibial implant of claim 17, wherein the weight bearing surface includes a concave weight bearing surface portion substantially in an anteroposterior direction that is positioned anteriorly relative to the convex weight bearing surface portion.

20. The tibial implant of claim 17, wherein the weight bearing surface includes a first concave weight bearing surface portion substantially in an anteroposterior direction that is positioned anteriorly relative to the convex weight bearing surface portion, and a second concave weight bearing surface portion substantially in an anteroposterior direction that is positioned posteriorly relative to the convex weight bearing surface portion.

21. The tibial implant of claim 17, wherein the weight bearing surface is curved in a mediolateral direction.

22. The tibial implant of claim 17, wherein the weight bearing surface is concave substantially in a coronal plane.

23. A tibial knee implant for implantation in a knee joint of a patient, comprising:
a tibial component configured to be implanted in a lateral compartment of a knee joint and having a weight bearing surface configured to articulate with an opposing surface and extending in a generally sagittal direction when the tibial implant is implanted in the knee joint of the patient, and a bone-facing surface configured to abut a surface of a tibia of the patient when the tibial implant is implanted in the knee joint of the patient, wherein the weight bearing surface includes a variable slope having a at least one portion forming a negative slope relative to the bone facing surface and at least one portion forming a positive slope relative to the bone facing surface, wherein the negative slope and the positive slope are on a substantially the same sagittal plane, wherein the variable slope of the weight bearing surface forms a convex weight bearing surface portion substantially in an anteroposterior direction and a concave weight bearing surface portion substantially in an anteroposterior direction.

24. The tibial knee implant of claim 23, wherein the variable slope of the weight bearing surface forms a convex weight bearing surface portion substantially in an anteroposterior direction and a concave weight bearing surface portion substantially in an anteroposterior direction that is positioned posteriorly relative to the convex weight bearing surface portion.

25. The tibial knee implant of claim 23, wherein the variable slope of the weight bearing surface forms a convex weight bearing surface portion substantially in an anteroposterior direction and a concave weight bearing surface portion substantially in an anteroposterior direction that is positioned anteriorly relative to the convex weight bearing surface portion.

26. The tibial knee implant of claim 23, wherein the variable slope of the weight bearing surface forms a convex weight bearing surface portion substantially in an anteroposterior direction, a first concave weight bearing surface portion substantially in an anteroposterior direction that is positioned anteriorly relative to the convex weight bearing surface portion, and a second concave weight bearing surface portion substantially in an anteroposterior direction that is positioned posteriorly relative to the convex weight bearing surface portion.

* * * * *